United States Patent
Hoffmann et al.

(10) Patent No.: US 9,179,676 B2
(45) Date of Patent: Nov. 10, 2015

(54) SUBSTITUTED PICOLINIC ACIDS AND PYRIMIDINE-4-CARBOXYLIC ACIDS, METHOD FOR THE PRODUCTION THEREOF AND USE THEREOF AS HERBICIDES AND PLANT GROWTH REGULATORS

(75) Inventors: Michael Gerhard Hoffmann, Flöersheim (DE); Marco Brüenjes, Hofheim (DE); Uwe Döller, Rodgau (DE); Hans-Jörg Dietrich, Liederbach am Taunus (DE); Isolde Häeuser-Hahn, Leverkusen (DE); Christopher Hugh Rosinger, Hofheim (DE); Elmar Gatzweiler, Bad Nauheim (DE); Ines Heinemann, Hofheim (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/233,038

(22) PCT Filed: Jul. 24, 2012

(86) PCT No.: PCT/EP2012/064519
§ 371 (c)(1),
(2), (4) Date: Mar. 27, 2014

(87) PCT Pub. No.: WO2013/014165
PCT Pub. Date: Jan. 31, 2013

(65) Prior Publication Data
US 2015/0005165 A1 Jan. 1, 2015

(30) Foreign Application Priority Data
Jul. 27, 2011 (EP) .................................. 11175511

(51) Int. Cl.
*A01N 43/40* (2006.01)
*A01N 43/52* (2006.01)
*A01N 43/54* (2006.01)
*A01N 43/56* (2006.01)
*A01N 43/647* (2006.01)
*A01N 43/76* (2006.01)
*A01N 43/78* (2006.01)
*A01N 43/80* (2006.01)
*C07D 401/04* (2006.01)
*C07D 403/04* (2006.01)
*C07D 405/04* (2006.01)
*C07D 409/04* (2006.01)
*C07D 413/04* (2006.01)
*C07D 417/04* (2006.01)
*A01N 43/58* (2006.01)
*C07D 411/04* (2006.01)

(52) U.S. Cl.
CPC ................ *A01N 43/40* (2013.01); *A01N 43/52* (2013.01); *A01N 43/54* (2013.01); *A01N 43/56* (2013.01); *A01N 43/647* (2013.01); *A01N 43/76* (2013.01); *A01N 43/78* (2013.01); *A01N 43/80* (2013.01); *C07D 401/04* (2013.01); *C07D 403/04* (2013.01); *C07D 405/04* (2013.01); *C07D 409/04* (2013.01); *C07D 413/04* (2013.01); *C07D 417/04* (2013.01); *A01N 43/58* (2013.01); *C07D 411/04* (2013.01)

(58) Field of Classification Search
CPC .... C07D 409/04; C07D 411/04; A01N 43/40; A01N 43/58
USPC ........ 514/337, 338, 256; 544/328; 546/268.4, 546/270.1, 271.1, 271.7, 272.1, 273.4, 546/275.7, 277.4, 281.1, 284.1
See application file for complete search history.

(56) References Cited

U.S. PATENT DOCUMENTS

2010/0137137 A1   6/2010  Rosinger et al.
2014/0274695 A1*  9/2014  Eckelbarger et al. ......... 504/103
(Continued)

FOREIGN PATENT DOCUMENTS

WO          03/011853       2/2003
WO          03011853 A1     2/2003
WO          WO 03011853 A1 * 2/2003
(Continued)

OTHER PUBLICATIONS

L. M. Abell et al. Target-Site Directed Herbicide Design in, Pest Control With Enhanced Environmental Safety 15-37 (ACS Symposium Series; American Chemical Society, S. Duke, et al. eds, 1993).*
S.C. Knight et al.,35 Annual Review of Phytopathology, 349-372, 357 (1997) ("Knight").*
W.T. Ruegg et al., 47 Weed Research, 271-275, 271 (2006).*
Dishington et al:"One-pot sulfide tosulfone oxidationwith m-chloroper-oxybenzoic acid and sodium per-manganate" Tetrahedron Letters, Eisevier, Amsterdam.
International Search Report for PCT/EP2012/064519 Mailed Sep. 28, 2012.

Primary Examiner — Alexander R Pagano
(74) Attorney, Agent, or Firm — Miles and Stockbridge

(57) ABSTRACT

The invention relates to a carboxylic acid derivatives of benzoheterocyclyl pyridines and benzoheterocyclyl pyrimidines of general formula (I) and to the use thereof as herbicides.

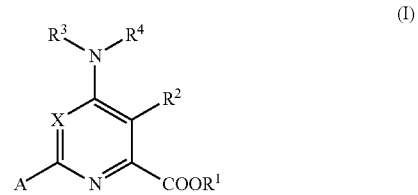

22 Claims, No Drawings

(56) References Cited

U.S. PATENT DOCUMENTS

2015/0126366 A1* 5/2015 Eckelbarger et al. ......... 504/103
2015/0126372 A1* 5/2015 Eckelbarger et al. ......... 504/242

FOREIGN PATENT DOCUMENTS

| WO | 2005063721 | A1 | 7/2005 |
| WO | 2007080382 | A1 | 7/2007 |
| WO | 2007082076 | A1 | 7/2007 |
| WO | 2007082098 | A2 | 7/2007 |
| WO | 2007120706 | A1 | 10/2007 |
| WO | 2009/007751 | | 1/2009 |
| WO | 2007092184 | A1 | 1/2009 |
| WO | 2009007751 | A2 | 1/2009 |
| WO | 2009023438 | A1 | 2/2009 |
| WO | 2009/029735 | | 3/2009 |
| WO | 2009029518 | A2 | 3/2009 |
| WO | 2009029735 | A1 | 3/2009 |
| WO | 2009046090 | A1 | 4/2009 |
| WO | 2009129291 | A1 | 10/2009 |
| WO | 2009/138712 | | 11/2009 |
| WO | 2009138712 | A2 | 11/2009 |
| WO | WO 2009138712 | A2 * | 11/2009 |
| WO | 201009339 | A1 | 1/2010 |
| WO | 2010/060581 | | 6/2010 |
| WO | 2010060581 | A2 | 6/2010 |
| WO | 2010/125332 | | 11/2010 |
| WO | 2010125332 | A1 | 11/2010 |

* cited by examiner

SUBSTITUTED PICOLINIC ACIDS AND PYRIMIDINE-4-CARBOXYLIC ACIDS, METHOD FOR THE PRODUCTION THEREOF AND USE THEREOF AS HERBICIDES AND PLANT GROWTH REGULATORS

CROSS REFERENCE TO RELATED APPLICATIONS

This application is a §371 National Stage Application of PCT/EP2012/064519, filed Jul. 24, 2012, which claims priority to European Application No. 11175511.2, filed Jul. 27, 2011.

BACKGROUND OF THE INVENTION

1. Field of the Invention

The invention relates to the technical field of herbicides, in particular that of herbicides for the selective control of broad-leaved weeds and weed grasses in crops of useful plants.

2. Description of Related Art

Various publications disclose that substituted picolinic acid derivatives and pyrimidine-4-carboxylic acid derivatives have herbicidal properties: WO 2003/011853 A1 discloses polysubstituted 6-phenylpicolinic acid derivatives having herbicidal action. WO2009/029735 A1 and WO2010/125332 A1 describe herbicidal effects for polysubstituted 2-phenyl-4-pyrimidinecarboxylic acid derivatives. Heteroaromatically substituted picoline- and pyrimidinecarboxylic acids having herbicidal properties are disclosed in WO 2009/138712 A2. WO 2007/080382 A1 and WO 2009/007751 A2 describe heteroaromatically substituted picoline- and pyrimidinecarboxylic acids having pharmacological activities.

However, the compounds described in these publications frequently have insufficient herbicidal activity and/or insufficient selectivity in crops of useful plants.

We have found substituted picolinic acids and pyrimidine-4-carboxylic acids which are particularly suitable as herbicides.

SUMMARY

The present invention provides picolinic acids and pyrimidine-4-carboxylic acids of the general formula (I), their N-oxides or their salts

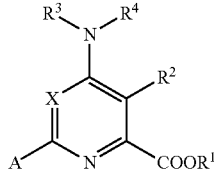

(I)

wherein
A represents a radical from the group consisting of A1 to A20,

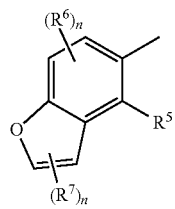

A1

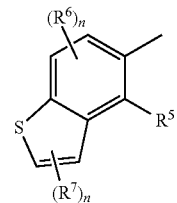

A2

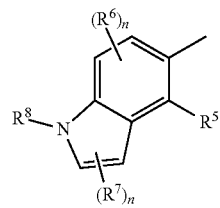

A3

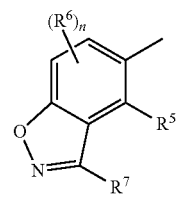

A4

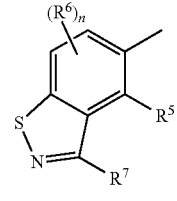

A5

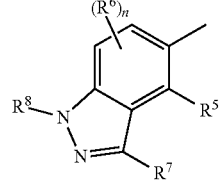

A6

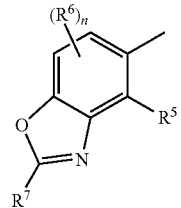

A7

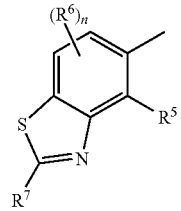

A8

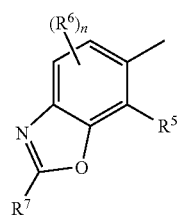 A9

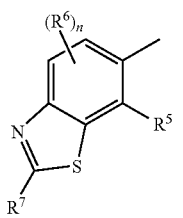 A10

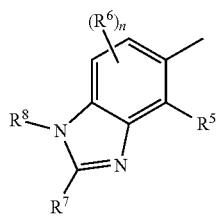 A11

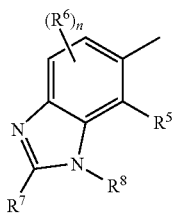 A12

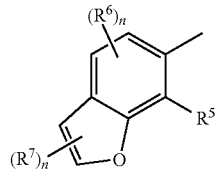 A13

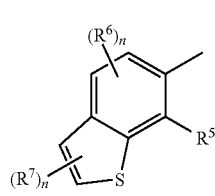 A14

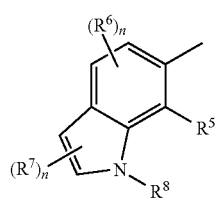 A15

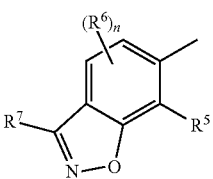 A16

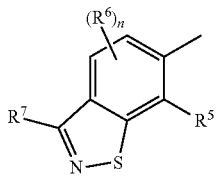 A17

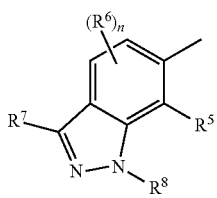 A18

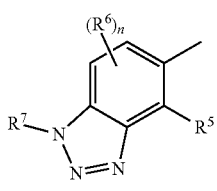 A19

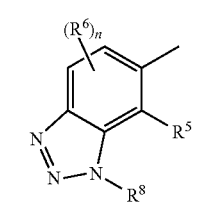 A20

$R^1$ represents hydrogen or $(C_1-C_4)$-alkyl,
$R^2$ represents chlorine,
$R^3$ represents hydrogen,
$R^4$ represents hydrogen,
$R^5$ represents hydrogen, halogen, OH, $NH_2$, CN, $(C_1-C_3)$-alkyl, $(C_1-C_3)$-alkoxy, $C_1-C_3$)-alkylamino or cyclopropyl,
$R^6$ represents hydrogen, halogen, OH, $NH_2$, CN, $(C_1-C_3)$-alkyl, $(C_1-C_3)$-alkoxy, cyclopropyl or vinyl,
$R^7$ represents hydrogen, halogen, $(C_1-C_3)$-alkyl, $(C_1-C_3)$-alkoxy, $(C_1-C_3)$-alkylthio, cyclopropyl, $(C_1-C_3)$-alkylamino or phenyl,
$R^8$ represents hydrogen, $(C_1-C_3)$-alkyl, phenyl or $(C_1-C_3)$-alkylcarbonyl,
X represents N, CH, CCl, CF or CBr,
n represents 0, 1 or 2.

DETAILED DESCRIPTION OF A PREFERRED EMBODIMENT

Alkyl means saturated, straight-chain or branched hydrocarbon radicals having 1 to 10 carbon atoms, for example $C_1-C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Haloalkyl means straight-chain or branched alkyl groups having 1 to 8 carbon atoms, where in these groups some or all of the hydrogen atoms may be replaced by halogen atoms, for example $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro, 2-difluoroethyl, 2,2-dichloro-2-fluoroethyl, 2,2,2-trichloroethyl, pentafluoroethyl and 1,1,1-trifluoroprop-2-yl.

Alkenyl means unsaturated, straight-chain or branched hydrocarbon radicals having 2 to 8 carbon atoms and a double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl means straight-chain or branched hydrocarbon radicals having 2 to 8 carbon atoms and a triple bond in any position, for example $C_2$-$C_6$-alkynyl such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Alkoxy means saturated, straight-chain or branched alkoxy radicals having 1 to 8 carbon atoms, for example $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy; haloalkoxy means straight-chain or branched alkoxy groups having 1 to 8 carbon atoms (as mentioned above), where in these groups some or all of the hydrogen atoms may be replaced by halogen atoms as mentioned above, for example $C_1$-$C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro, 2-difluoroethoxy, 2,2-dichloro-2-fluoroethoxy, 2,2,2-trichloroethoxy, pentafluoroethoxy and 1,1,1-trifluoroprop-2-oxy.

Alkylthio means saturated, straight-chain or branched alkylthio radicals having 1 to 8 carbon atoms, for example $C_1$-$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio; haloalkylthio means straight-chain or branched alkylthio groups having 1 to 8 carbon atoms (as mentioned above), where in these groups some or all of the hydrogen atoms may be replaced by halogen atoms as mentioned above, for example $C_1$-$C_2$-haloalkylthio such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro, 2-difluoroethylthio, 2,2-dichloro-2-fluoroethylthio, 2,2,2-trichloroethylthio, pentafluoroethylthio and 1,1,1-trifluoroprop-2-ylthio.

Aryl means phenyl or naphthyl.

Depending inter alia on the nature of the substituents, the compounds of the formula (I) can be present as geometrical and/or optical isomers or isomer mixtures of varying composition which, if desired, can be separated in a customary manner. The present invention provides both the pure isomers and the isomer mixtures, their preparation and use and compositions comprising them. For the sake of simplicity, however, compounds of the formula (I) are always referred to below, although both the pure compounds and also, if appropriate, mixtures having different proportions of isomeric compounds are meant.

A metal ion equivalent is a metal ion having a positive charge, such as $Na^+$, $K^+$, $(Mg^{2+})_{1/2}$, $(Ca^{2+})_{1/2}$, $MgH^+$, $CaH^+$, $(Al^{3+})_{1/3}$ $(Fe^{2+})_{1/2}$ or $(Fe^{3+})_{1/3}$.

Halogen is fluorine, chlorine, bromine or iodine.

Where a group is substituted by a plurality of radicals, this means that this group is substituted by one or more identical or different representatives of the radicals mentioned.

Depending on the nature of the substituents defined above, the compounds of the formula (I) have acidic or basic properties and can form salts, if appropriate also inner salts, or adducts with inorganic or organic acids or with bases or with metal ions. If the compounds of the formula (I) carry amino, alkylamino or other groups which induce basic properties, these compounds can be reacted with acids to give salts, or they are directly obtained as salts in the synthesis.

Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as $NaHSO_4$ and $KHSO_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulfonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminum, tin and lead, and also of the first to eighth transition group, in particular chromium, manganese, iron, cobalt, nickel, copper, zinc and others. Particular preference is given to the metal ions of the elements of the fourth period. Here, the metals can be present in the various valencies that they can assume.

If the compounds of the formula (I) carry hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having $(C_1-C_4)$-alkyl groups, mono-, di- and trialkanolamines of $(C_1-C_4)$-alkanols, choline and also chlorocholine.

Depending on the nature and the attachment of the substituents, the compounds of the general formula (I) may be present as stereoisomers. If, for example, one or more asymmetrically substituted carbon atoms or sulfoxides are present, there may be enantiomers and diastereomers. Stereoisomers may be obtained from the mixtures resulting from the preparation using customary separation methods, for example by chromatographic separation techniques. It is also possible to prepare stereoisomers selectively by using stereoselective reactions employing optically active starting materials and/or auxiliaries. The invention also relates to all stereoisomers and mixtures thereof embraced by the general formula (I) but not specifically defined.

In all of the formulae below, the substituents and symbols have the same definition as described under formula (I), unless otherwise defined.

Compounds of the formula (I) can be prepared, for example, according to the scheme below by a palladium-catalyzed coupling reaction of a halogen compound (II) with a boronic acid derivative (III). In this scheme, Het represents the heterocycles of groups A1 to A24 fused to the phenyl ring. R represents hydrogen or $(C_1-C_3)$-alkyl.

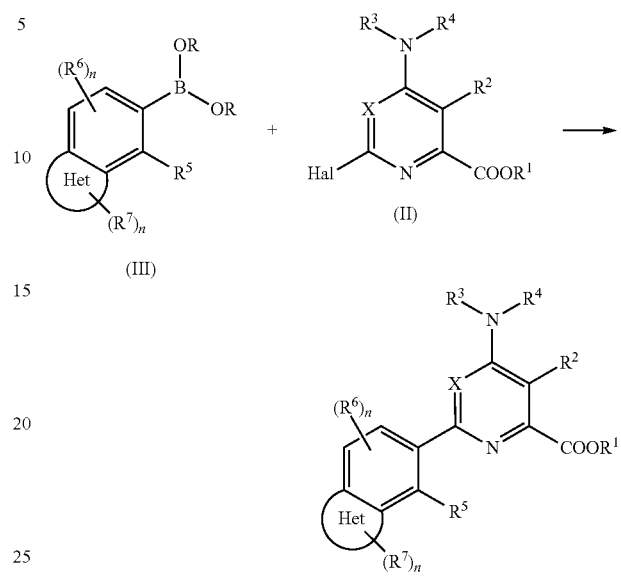

The halogen compounds of the formula (II) are known, for example, from WO2001051468 A1 and WO2007082076 A1, or they can be prepared by methods known per se to the person skilled in the art. The boronic acid derivatives of the formula (III) are commercially available or can be prepared by methods known per se to the person skilled in the art.

Preference is given to the compounds of the formula (I) listed in Tables 1 to 44, which compounds can be prepared analogously to the methods mentioned herein. The abbreviations used denote:
Et=ethyl Me=methyl Pr=propyl Ph=phenyl

TABLE 1

Compounds according to the invention of the formula (I) in which X represents CH, A represents A1, $R^3$ and $R^4$ each represent hydrogen and $R^2$ represents chlorine:

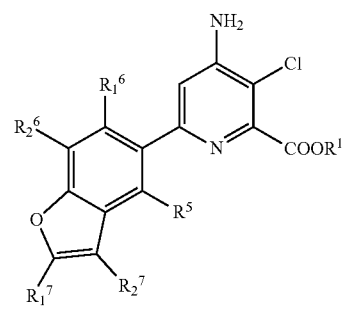

| Ex. No. | $R^1$ | $R^5$ | $R_1^6$ | $R_2^6$ | $R_1^7$ | $R_2^7$ |
|---|---|---|---|---|---|---|
| 1.001 | H | H | H | H | H | H |
| 1.002 | H | F | H | H | H | H |
| 1.003 | H | F | H | H | Cl | H |
| 1.004 | H | F | H | H | H | Cl |
| 1.005 | H | F | H | H | Cl | Cl |
| 1.006 | H | F | H | H | Ph | H |
| 1.007 | H | F | H | H | Ph | Cl |
| 1.008 | H | F | H | H | Ph | F |
| 1.009 | H | F | H | H | Me | H |
| 1.010 | H | F | H | H | Me | Cl |

TABLE 1-continued

Compounds according to the invention of the formula (I) in which X represents CH, A represents A1, $R^3$ and $R^4$ each represent hydrogen and $R^2$ represents chlorine:

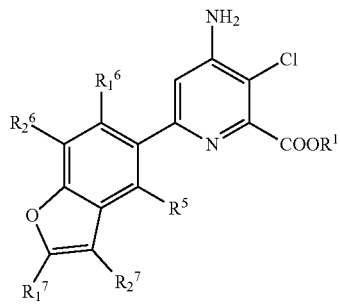

| Ex. No. | $R^1$ | $R^5$ | $R_1^6$ | $R_2^6$ | $R_1^7$ | $R_2^7$ |
|---|---|---|---|---|---|---|
| 1.011 | H | F | H | H | Me | F |
| 1.012 | Me | H | H | H | H | H |
| 1.013 | Me | F | H | H | H | H |
| 1.014 | Me | F | H | H | Cl | H |
| 1.015 | Me | F | H | H | H | Cl |
| 1.016 | Me | F | H | H | Cl | Cl |
| 1.017 | Me | F | H | H | H | F |
| 1.018 | Me | F | H | H | Ph | H |
| 1.019 | Me | F | H | H | Ph | Cl |
| 1.020 | Me | F | H | H | Ph | F |
| 1.021 | Me | F | H | H | Me | H |
| 1.022 | Me | F | H | H | Me | Cl |
| 1.023 | Me | F | H | H | Me | F |
| 1.024 | Et | H | H | H | H | H |
| 1.025 | Et | Cl | H | H | H | H |
| 1.026 | Et | Cl | H | H | Cl | H |
| 1.027 | Et | Cl | H | H | H | Cl |
| 1.028 | Et | Cl | H | H | Cl | Cl |
| 1.029 | Et | Cl | H | H | H | F |
| 1.030 | Et | Cl | H | H | Ph | H |
| 1.031 | Et | Cl | H | H | Ph | Cl |
| 1.032 | Et | Cl | H | H | Ph | F |
| 1.033 | Et | Cl | H | H | Me | H |
| 1.034 | Et | Cl | H | H | Me | Cl |
| 1.035 | Et | Cl | H | H | Me | F |
| 1.036 | H | F | F | H | H | H |
| 1.037 | H | F | H | F | H | H |
| 1.038 | Me | H | F | H | H | H |
| 1.039 | H | H | F | H | H | H |
| 1.040 | K | H | F | H | H | H |
| 1.041 | Me | H | Cl | H | H | H |
| 1.042 | H | H | Cl | H | H | H |
| 1.043 | K | H | Cl | H | H | H |
| 1.044 | Me | H | H | F | H | H |
| 1.045 | H | H | H | F | H | H |
| 1.046 | K | H | H | F | H | H |
| 1.047 | Me | H | H | Cl | H | H |
| 1.048 | H | H | H | Cl | H | H |
| 1.049 | K | H | H | Cl | H | H |
| 1.050 | K | F | H | H | H | H |
| 1.051 | Me | Cl | H | H | H | H |
| 1.052 | H | Cl | H | H | H | H |
| 1.053 | Na | Cl | H | H | H | H |

TABLE 2

Compounds according to the invention of the formula (I) in which X represents CH, A represents A2, $R^3$ and $R^4$ each represent hydrogen and $R^2$ represents chlorine:

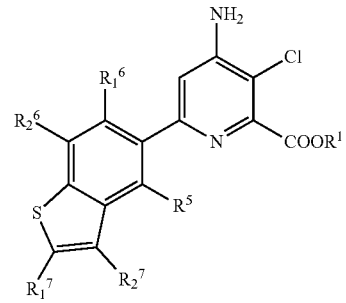

| Ex. No. | $R^1$ | $R^5$ | $R_1^6$ | $R_2^6$ | $R_1^7$ | $R_2^7$ |
|---|---|---|---|---|---|---|
| 2.001 | H | H | H | H | H | H |
| 2.002 | H | F | H | H | H | H |
| 2.003 | H | F | H | H | Cl | H |
| 2.004 | H | F | H | H | H | Cl |
| 2.005 | H | F | H | H | Cl | Cl |
| 2.006 | H | F | H | H | Ph | H |
| 2.007 | H | F | H | H | Ph | Cl |
| 2.008 | H | F | H | H | Ph | F |
| 2.009 | H | F | H | H | Me | H |
| 2.010 | H | F | H | H | Me | Cl |
| 2.011 | H | F | H | H | Me | F |
| 2.012 | Me | H | H | H | H | H |
| 2.013 | Me | F | H | H | H | H |
| 2.014 | Me | F | H | H | Cl | H |
| 2.015 | Me | F | H | H | H | Cl |
| 2.016 | Me | F | H | H | Cl | Cl |
| 2.017 | Me | F | H | H | H | F |
| 2.018 | Me | F | H | H | Ph | H |
| 2.019 | Me | F | H | H | Ph | Cl |
| 2.020 | Me | F | H | H | Ph | F |
| 2.021 | Me | F | H | H | Me | H |
| 2.022 | Me | F | H | H | Me | Cl |
| 2.023 | Me | F | H | H | Me | F |
| 2.024 | Et | H | H | H | H | H |
| 2.025 | Et | Cl | H | H | H | H |
| 2.026 | Et | Cl | H | H | Cl | H |
| 2.027 | Et | Cl | H | H | H | Cl |
| 2.028 | Et | Cl | H | H | Cl | Cl |
| 2.029 | Et | Cl | H | H | H | F |
| 2.030 | Et | Cl | H | H | Ph | H |
| 2.031 | Et | Cl | H | H | Ph | Cl |
| 2.032 | Et | Cl | H | H | Ph | F |
| 2.033 | Et | Cl | H | H | Me | H |
| 2.034 | Et | Cl | H | H | Me | Cl |
| 2.035 | Et | Cl | H | H | Me | F |
| 2.036 | H | F | F | H | H | H |
| 2.037 | H | F | H | F | H | H |
| 2.038 | Me | H | F | H | H | H |
| 2.039 | H | H | F | H | H | H |
| 2.040 | K | H | F | H | H | H |
| 2.041 | Me | H | Cl | H | H | H |
| 2.042 | H | H | Cl | H | H | H |
| 2.043 | K | H | Cl | H | H | H |
| 2.044 | Me | H | H | F | H | H |
| 2.045 | H | H | H | F | H | H |
| 2.046 | K | H | H | F | H | H |
| 2.047 | Me | H | H | Cl | H | H |
| 2.048 | H | H | H | Cl | H | H |
| 2.049 | K | H | H | Cl | H | H |
| 2.050 | K | F | H | H | H | H |
| 2.051 | Me | Cl | H | H | H | H |
| 2.052 | H | Cl | H | H | H | H |
| 2.053 | K | Cl | H | H | H | H |

TABLE 3

Compounds according to the invention of the formula (I) in which X represents CH, A represents A3, $R^3$ and $R^4$ each represent hydrogen and $R^2$ represents chlorine:

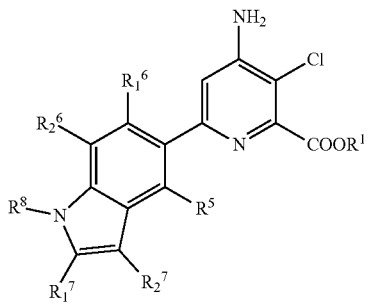

| Ex. No. | $R^1$ | $R^5$ | $R_1^6$ | $R_2^6$ | $R_1^7$ | $R_2^7$ | $R^8$ |
|---|---|---|---|---|---|---|---|
| 3.001 | H | H | H | H | H | H | H |
| 3.002 | H | F | H | H | H | H | Me |
| 3.003 | H | F | H | H | Cl | H | H |
| 3.004 | H | F | H | H | H | Cl | Me |
| 3.005 | H | F | H | H | Cl | Cl | Me |
| 3.006 | H | F | H | H | Ph | H | Me |
| 3.007 | H | F | H | H | Ph | Cl | H |
| 3.008 | H | F | H | H | Ph | F | H |
| 3.009 | H | F | H | H | Me | H | H |
| 3.010 | H | F | H | H | Me | Cl | Me |
| 3.011 | H | F | H | H | Me | F | Me |
| 3.012 | Me | H | H | H | H | H | Me |
| 3.013 | Me | F | H | H | H | H | H |
| 3.014 | Me | F | H | H | Cl | H | H |
| 3.015 | Me | F | H | H | H | Cl | Me |
| 3.016 | Me | F | H | H | Cl | Cl | Me |
| 3.017 | Me | F | H | H | H | F | Me |
| 3.018 | Me | F | H | H | Ph | H | H |
| 3.019 | Me | F | H | H | Ph | Cl | H |
| 3.020 | Me | F | H | H | Ph | F | H |
| 3.021 | Me | F | H | H | Me | H | H |
| 3.022 | Me | F | H | H | Me | Cl | Me |
| 3.023 | Me | F | H | H | Me | F | H |
| 3.024 | Et | H | H | H | H | H | Me |
| 3.025 | Et | Cl | H | H | H | H | Me |
| 3.026 | Et | Cl | H | H | Cl | H | Me |
| 3.027 | Et | Cl | H | H | H | Cl | Me |
| 3.028 | Et | Cl | H | H | Cl | Cl | Me |
| 3.029 | Et | Cl | H | H | H | F | Me |
| 3.030 | Et | Cl | H | H | Ph | H | H |
| 3.031 | Et | Cl | H | H | Ph | Cl | H |
| 3.032 | Et | Cl | H | H | Ph | F | H |
| 3.033 | Et | Cl | H | H | Me | H | H |
| 3.034 | Et | Cl | H | H | Me | Cl | H |
| 3.035 | Et | Cl | H | H | Me | F | Me |
| 3.036 | H | F | F | H | H | H | H |
| 3.037 | H | F | H | F | H | H | H |

TABLE 4

Compounds according to the invention of the formula (I) in which X represents CH, A represents A4, $R^3$ and $R^4$ each represent hydrogen and $R^2$ represents chlorine:

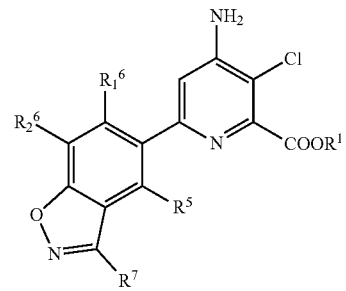

| Ex. No. | $R^1$ | $R^5$ | $R_1^6$ | $R_2^6$ | $R^7$ |
|---|---|---|---|---|---|
| 4.001 | H | H | H | H | H |
| 4.002 | H | F | H | H | H |
| 4.003 | H | F | H | H | F |
| 4.004 | H | F | H | H | Cl |
| 4.005 | H | F | H | H | Me |
| 4.006 | H | Cl | H | H | H |
| 4.007 | H | Cl | H | H | F |
| 4.008 | H | Cl | H | H | Cl |
| 4.009 | H | Cl | H | H | Me |
| 4.010 | Me | H | H | H | H |
| 4.011 | Me | F | H | H | H |
| 4.012 | Me | F | H | H | F |
| 4.013 | Me | F | H | H | Cl |
| 4.014 | Me | Cl | H | H | H |
| 4.015 | Me | Cl | H | H | F |
| 4.016 | Me | Cl | H | H | Cl |
| 4.017 | Me | Cl | H | H | Me |
| 4.018 | Et | H | H | H | H |
| 4.019 | Et | F | H | H | H |
| 4.020 | Et | Cl | H | H | H |
| 4.021 | Et | F | H | H | Me |
| 4.022 | Et | Cl | H | H | Me |
| 4.023 | H | F | F | H | H |
| 4.024 | H | F | H | F | H |

TABLE 5

Compounds according to the invention of the formula (I) in which X represents CH, A represents A5, $R^3$ and $R^4$ each represent hydrogen and $R^2$ represents chlorine:

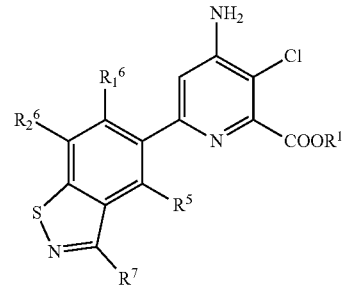

| Ex. No. | $R^1$ | $R^5$ | $R_1^6$ | $R_2^6$ | $R^7$ |
|---|---|---|---|---|---|
| 5.001 | H | H | H | H | H |
| 5.002 | H | F | H | H | H |
| 5.003 | H | F | H | H | F |
| 5.004 | H | F | H | H | Cl |
| 5.005 | H | F | H | H | F |
| 5.006 | H | Cl | H | H | H |
| 5.007 | H | Cl | H | H | F |
| 5.008 | H | Cl | H | H | Cl |
| 5.009 | H | Cl | H | H | Me |
| 5.010 | Me | H | H | H | H |

TABLE 5-continued

Compounds according to the invention of the formula (I) in which X represents CH, A represents A5, $R^3$ and $R^4$ each represent hydrogen and $R^2$ represents chlorine:

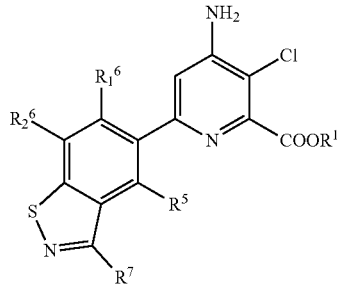

| Ex. No. | $R^1$ | $R^5$ | $R_1^6$ | $R_2^6$ | $R^7$ |
|---|---|---|---|---|---|
| 5.011 | Me | F | H | H | H |
| 5.012 | Me | F | H | H | Cl |
| 5.013 | Me | Cl | H | H | H |
| 5.014 | Me | Cl | H | H | F |
| 5.015 | Me | Cl | H | H | Cl |
| 5.016 | Me | Cl | H | H | Me |
| 5.017 | Et | H | H | H | H |
| 5.018 | Et | F | H | H | H |
| 5.019 | Et | Cl | H | H | H |
| 5.020 | Et | F | H | H | Me |
| 5.021 | Et | Cl | H | H | Me |
| 5.022 | H | F | F | H | H |
| 5.023 | H | F | H | F | H |

TABLE 6

Compounds according to the invention of the formula (I) in which X represents CH, A represents A6, $R^8$, $R^3$ and $R^4$ each represent hydrogen and $R^2$ represents chlorine:

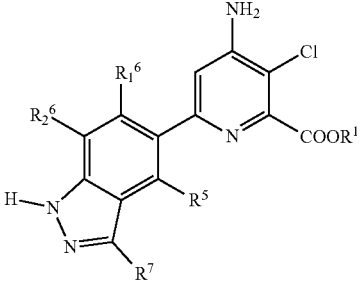

| Ex. No. | $R^1$ | $R^5$ | $R_1^6$ | $R_2^6$ | $R^7$ |
|---|---|---|---|---|---|
| 6.001 | H | H | H | H | H |
| 6.002 | H | F | H | H | H |
| 6.003 | H | F | H | H | Me |
| 6.004 | H | F | H | H | Et |
| 6.005 | H | H | H | H | Me |
| 6.006 | H | Cl | H | H | H |
| 6.007 | H | Cl | H | H | Me |
| 6.008 | H | Cl | H | H | Et |
| 6.009 | Me | H | H | H | H |
| 6.010 | Me | H | H | H | Me |
| 6.011 | Me | F | H | H | H |
| 6.012 | Me | F | H | H | Me |
| 6.013 | Me | F | H | H | Et |
| 6.014 | Me | Cl | H | H | H |
| 6.015 | Me | Cl | H | H | Me |
| 6.016 | Me | Cl | H | H | Et |
| 6.017 | Me | H | H | H | Me |
| 6.018 | Et | H | H | H | H |
| 6.019 | Et | H | H | H | Me |
| 6.020 | Et | H | H | H | Et |
| 6.021 | Et | F | H | H | H |

TABLE 6-continued

Compounds according to the invention of the formula (I) in which X represents CH, A represents A6, $R^8$, $R^3$ and $R^4$ each represent hydrogen and $R^2$ represents chlorine:

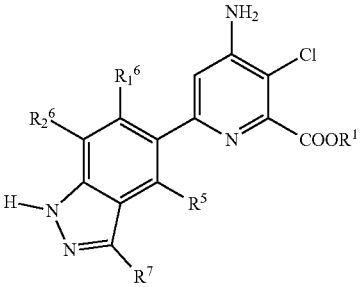

| Ex. No. | $R^1$ | $R^5$ | $R_1^6$ | $R_2^6$ | $R^7$ |
|---|---|---|---|---|---|
| 6.022 | Et | F | H | H | Me |
| 6.023 | Et | F | H | H | Et |
| 6.024 | Et | Cl | H | H | H |
| 6.025 | Et | Cl | H | H | Me |
| 6.026 | Et | Cl | H | H | Et |
| 6.027 | H | F | F | H | H |
| 6.028 | H | F | H | F | H |

TABLE 7

Compounds according to the invention of the formula (I) in which X represents CH, A represents A6, $R^3$ and $R^4$ each represent hydrogen, $R^8$ represents methyl and $R^2$ represents chlorine:

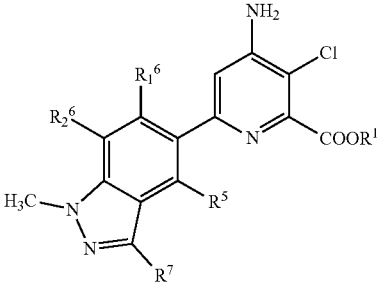

| Ex. No. | $R^1$ | $R^5$ | $R_1^6$ | $R_2^6$ | $R^7$ |
|---|---|---|---|---|---|
| 7.001 | H | H | H | H | H |
| 7.002 | H | F | H | H | H |
| 7.003 | H | F | H | H | Me |
| 7.004 | H | F | H | H | Et |
| 7.005 | H | H | H | H | Me |
| 7.006 | H | Cl | H | H | H |
| 7.007 | H | Cl | H | H | Me |
| 7.008 | H | Cl | H | H | Et |
| 7.009 | Me | H | H | H | H |
| 7.010 | Me | H | H | H | Me |
| 7.011 | Me | F | H | H | H |
| 7.012 | Me | F | H | H | Me |
| 7.013 | Me | F | H | H | Et |
| 7.014 | Me | Cl | H | H | H |
| 7.015 | Me | Cl | H | H | Me |
| 7.016 | Me | Cl | H | H | Et |
| 7.017 | Me | H | H | H | Me |
| 7.018 | Et | H | H | H | H |
| 7.019 | Et | H | H | H | Me |
| 7.020 | Et | H | H | H | Et |
| 7.021 | Et | F | H | H | H |
| 7.022 | Et | F | H | H | Me |
| 7.023 | Et | F | H | H | Et |
| 7.024 | Et | Cl | H | H | H |
| 7.025 | Et | Cl | H | H | Me |
| 7.026 | Et | Cl | H | H | Et |

TABLE 7-continued

Compounds according to the invention of the formula (I) in which X represents CH, A represents A6, $R^3$ and $R^4$ each represent hydrogen, $R^8$ represents methyl and $R^2$ represents chlorine:

| Ex. No. | $R^1$ | $R^5$ | $R_1^6$ | $R_2^6$ | $R^7$ |
|---|---|---|---|---|---|
| 7.027 | H | F | F | H | H |
| 7.028 | H | F | H | F | H |

TABLE 8

Compounds according to the invention of the formula (I) in which X represents CH, A represents A7, $R^3$ and $R^4$ each represent hydrogen and $R^2$ represents chlorine:

| Ex. No. | $R^1$ | $R^5$ | $R_1^6$ | $R_2^6$ | $R^7$ |
|---|---|---|---|---|---|
| 8.001 | H | H | H | H | H |
| 8.002 | H | H | H | H | Me |
| 8.003 | H | H | H | H | Ph |
| 8.004 | H | H | H | H | SMe |
| 8.005 | H | F | H | H | H |
| 8.006 | H | F | H | H | Me |
| 8.007 | H | F | H | H | Ph |
| 8.008 | H | F | H | H | SMe |
| 8.009 | H | Cl | H | H | H |
| 8.010 | H | Cl | H | H | Me |
| 8.011 | H | Cl | H | H | Ph |
| 8.012 | H | Cl | H | H | SMe |
| 8.013 | Me | H | H | H | H |
| 8.014 | Me | H | H | H | Me |
| 8.015 | Me | H | H | H | Ph |
| 8.016 | Me | H | H | H | SMe |
| 8.017 | Me | F | H | H | H |
| 8.018 | Me | F | H | H | Me |
| 8.019 | Me | F | H | H | Ph |
| 8.020 | Me | F | H | H | SMe |
| 8.021 | Me | Cl | H | H | H |
| 8.022 | Me | Cl | H | H | Me |
| 8.023 | Me | Cl | H | H | Ph |
| 8.024 | Me | Cl | H | H | SMe |
| 8.025 | Et | H | H | H | H |
| 8.026 | Et | H | H | H | Me |
| 8.027 | Et | H | H | H | Ph |
| 8.028 | Et | H | H | H | SMe |
| 8.029 | Et | F | H | H | H |
| 8.030 | Et | F | H | H | Me |
| 8.031 | Et | F | H | H | Ph |
| 8.032 | Et | F | H | H | SMe |
| 8.033 | Et | Cl | H | H | H |
| 8.034 | Et | Cl | H | H | Me |
| 8.035 | Et | Cl | H | H | Ph |
| 8.036 | Et | Cl | H | H | SMe |
| 8.037 | H | F | F | H | H |
| 8.038 | H | F | H | F | H |

TABLE 9

Compounds according to the invention of the formula (I) in which X represents CH, A represents A8, $R^3$ and $R^4$ each represent hydrogen and $R^2$ represents chlorine:

| Ex. No. | $R^1$ | $R^5$ | $R_1^6$ | $R_2^6$ | $R^7$ |
|---|---|---|---|---|---|
| 9.001 | H | H | H | H | H |
| 9.002 | H | H | H | H | Me |
| 9.003 | H | H | H | H | Ph |
| 9.004 | H | H | H | H | SMe |
| 9.005 | H | F | H | H | H |
| 9.006 | H | F | H | H | Me |
| 9.007 | H | F | H | H | Ph |
| 9.008 | H | F | H | H | SMe |
| 9.009 | H | Cl | H | H | H |
| 9.010 | H | Cl | H | H | Me |
| 9.011 | H | Cl | H | H | Ph |
| 9.012 | H | Cl | H | H | SMe |
| 9.013 | Me | H | H | H | H |
| 9.014 | Me | H | H | H | Me |
| 9.015 | Me | H | H | H | Ph |
| 9.016 | Me | H | H | H | SMe |
| 9.017 | Me | F | H | H | H |
| 9.018 | Me | F | H | H | Me |
| 9.019 | Me | F | H | H | Ph |
| 9.020 | Me | F | H | H | SMe |
| 9.021 | Me | Cl | H | H | H |
| 9.022 | Et | H | H | H | H |
| 9.023 | Et | H | H | H | Me |
| 9.024 | Et | H | H | H | Ph |
| 9.025 | Et | H | H | H | SMe |

TABLE 9-continued

Compounds according to the invention of the formula (I) in which X represents CH, A represents A8, $R^3$ and $R^4$ each represent hydrogen and $R^2$ represents chlorine:

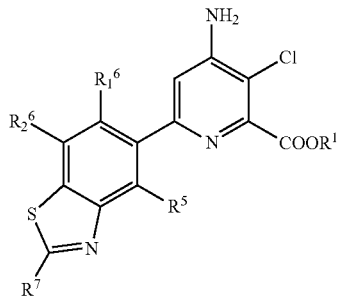

| Ex. No. | $R^1$ | $R^5$ | $R_1^6$ | $R_2^6$ | $R^7$ |
|---|---|---|---|---|---|
| 9.026 | Et | F | H | H | H |
| 9.027 | Et | F | H | H | Me |
| 9.028 | Et | F | H | H | Ph |
| 9.029 | Et | F | H | H | SMe |
| 9.030 | Et | Cl | H | H | H |
| 9.031 | Et | Cl | H | H | Me |
| 9.032 | Et | Cl | H | H | Ph |
| 9.033 | Et | Cl | H | H | SMe |
| 9.034 | H | F | F | H | H |
| 9.035 | H | F | H | F | H |

TABLE 10

Compounds according to the invention of the formula (I) in which X represents CH, A represents A9, $R^3$ and $R^4$ each represent hydrogen and $R^2$ represents chlorine:

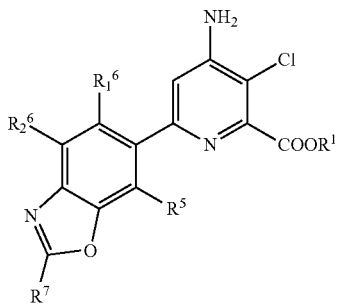

| Ex. No. | $R^1$ | $R^5$ | $R_1^6$ | $R_2^6$ | $R^7$ |
|---|---|---|---|---|---|
| 10.001 | H | H | H | H | H |
| 10.002 | H | H | H | H | Me |
| 10.003 | H | H | H | H | Ph |
| 10.004 | H | H | H | H | SMe |
| 10.005 | H | F | H | H | H |
| 10.006 | H | F | H | H | Me |
| 10.007 | H | F | H | H | Ph |
| 10.008 | H | F | H | H | SMe |
| 10.009 | H | Cl | H | H | H |
| 10.010 | H | Cl | H | H | Me |
| 10.011 | H | Cl | H | H | Ph |
| 10.012 | H | Cl | H | H | SMe |
| 10.013 | Me | H | H | H | H |
| 10.014 | Me | H | H | H | Me |
| 10.015 | Me | H | H | H | Ph |
| 10.016 | Me | H | H | H | SMe |
| 10.017 | Me | F | H | H | H |
| 10.018 | Me | F | H | H | Me |
| 10.019 | Me | F | H | H | Ph |
| 10.020 | Me | F | H | H | SMe |
| 10.021 | Me | Cl | H | H | H |
| 10.022 | Me | Cl | H | H | Me |
| 10.023 | Me | Cl | H | H | Ph |

TABLE 10-continued

Compounds according to the invention of the formula (I) in which X represents CH, A represents A9, $R^3$ and $R^4$ each represent hydrogen and $R^2$ represents chlorine:

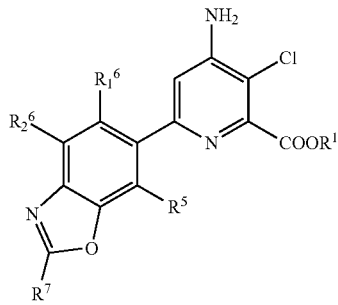

| Ex. No. | $R^1$ | $R^5$ | $R_1^6$ | $R_2^6$ | $R^7$ |
|---|---|---|---|---|---|
| 10.024 | Me | Cl | H | H | SMe |
| 10.025 | Et | H | H | H | H |
| 10.026 | Et | H | H | H | Me |
| 10.027 | Et | H | H | H | Ph |
| 10.028 | Et | H | H | H | SMe |
| 10.029 | Et | F | H | H | H |
| 10.030 | Et | F | H | H | Me |
| 10.031 | Et | F | H | H | Ph |
| 10.032 | Et | F | H | H | SMe |
| 10.033 | Et | Cl | H | H | H |
| 10.034 | Et | Cl | H | H | Me |
| 10.035 | Et | Cl | H | H | Ph |
| 10.036 | Et | Cl | H | H | SMe |
| 10.037 | H | F | F | H | H |
| 10.038 | H | F | H | F | H |

TABLE 11

Compounds according to the invention of the formula (I) in which X represents CH, A represents A10, $R^3$ and $R^4$ each represent hydrogen and $R^2$ represents chlorine:

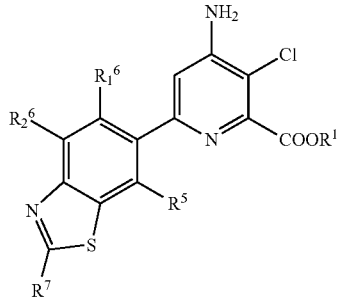

| Ex. No. | $R^1$ | $R^5$ | $R_1^6$ | $R_2^6$ | $R^7$ |
|---|---|---|---|---|---|
| 11.001 | H | H | H | H | H |
| 11.002 | H | H | H | H | Me |
| 11.003 | H | H | H | H | Ph |
| 11.004 | H | H | H | H | SMe |
| 11.005 | H | F | H | H | H |
| 11.006 | H | F | H | H | Me |
| 11.007 | H | F | H | H | Ph |
| 11.008 | H | F | H | H | SMe |
| 11.009 | H | Cl | H | H | H |
| 11.010 | H | Cl | H | H | Me |
| 11.011 | H | Cl | H | H | Ph |
| 11.012 | H | Cl | H | H | SMe |
| 11.013 | Me | H | H | H | H |
| 11.014 | Me | H | H | H | Me |
| 11.015 | Me | H | H | H | Ph |
| 11.016 | Me | H | H | H | SMe |
| 11.017 | Me | F | H | H | H |

TABLE 11-continued

Compounds according to the invention of the formula (I) in which X represents CH, A represents A10, $R^3$ and $R^4$ each represent hydrogen and $R^2$ represents chlorine:

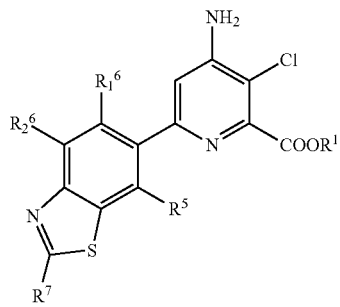

| Ex. No. | $R^1$ | $R^5$ | $R_1^6$ | $R_2^6$ | $R^7$ |
|---|---|---|---|---|---|
| 11.018 | Me | F | H | H | Me |
| 11.019 | Me | F | H | H | Ph |
| 11.020 | Me | F | H | H | SMe |
| 11.021 | Me | Cl | H | H | H |
| 11.022 | Et | H | H | H | H |
| 11.023 | Et | H | H | H | Me |
| 11.024 | Et | H | H | H | Ph |
| 11.025 | Et | H | H | H | SMe |
| 11.026 | Et | F | H | H | H |
| 11.027 | Et | F | H | H | Me |
| 11.028 | Et | F | H | H | Ph |
| 11.029 | Et | F | H | H | SMe |
| 11.030 | Et | Cl | H | H | H |
| 11.031 | Et | Cl | H | H | Me |
| 11.032 | Et | Cl | H | H | Ph |
| 11.033 | Et | Cl | H | H | SMe |
| 11.034 | H | F | F | H | H |
| 11.035 | H | F | H | F | H |

TABLE 12

Compounds according to the invention of the formula (I) in which X represents CH, A represents A11, $R^3$ and $R^4$ each represent hydrogen and $R^2$ represents chlorine:

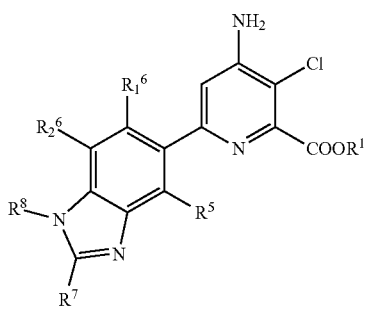

| Ex. No. | $R^1$ | $R^5$ | $R_1^6$ | $R_2^6$ | $R^7$ | $R^8$ |
|---|---|---|---|---|---|---|
| 12.001 | H | H | H | H | H | H |
| 12.002 | H | F | H | H | H | H |
| 12.003 | H | F | H | H | H | Me |
| 12.004 | H | F | H | H | Me | H |
| 12.005 | H | F | H | H | Me | Me |
| 12.006 | H | Cl | H | H | H | H |
| 12.007 | H | Cl | H | H | H | Me |
| 12.008 | H | Cl | H | H | Me | H |
| 12.009 | H | Cl | H | H | Me | Me |
| 12.010 | H | H | H | H | Ph | H |
| 12.011 | H | H | H | H | Ph | Me |
| 12.012 | H | F | H | H | Ph | H |
| 12.013 | H | F | H | H | Ph | Me |
| 12.014 | H | Cl | H | H | Ph | H |

TABLE 12-continued

Compounds according to the invention of the formula (I) in which X represents CH, A represents A11, $R^3$ and $R^4$ each represent hydrogen and $R^2$ represents chlorine:

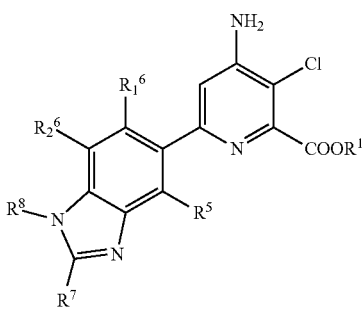

| Ex. No. | $R^1$ | $R^5$ | $R_1^6$ | $R_2^6$ | $R^7$ | $R^8$ |
|---|---|---|---|---|---|---|
| 12.015 | H | Cl | H | H | Ph | Me |
| 12.016 | H | H | H | H | Me | H |
| 12.017 | H | H | H | H | H | Me |
| 12.018 | H | H | H | H | Me | Me |
| 12.019 | Me | H | H | H | H | H |
| 12.020 | Me | F | H | H | H | H |
| 12.021 | Me | F | H | H | H | Me |
| 12.022 | Me | F | H | H | Me | H |
| 12.023 | Me | F | H | H | Me | Me |
| 12.024 | Me | Cl | H | H | H | H |
| 12.025 | Me | Cl | H | H | H | Me |
| 12.026 | Me | Cl | H | H | Me | H |
| 12.027 | Me | Cl | H | H | Me | Me |
| 12.028 | Me | H | H | H | Ph | H |
| 12.029 | Me | H | H | H | Ph | Me |
| 12.030 | Me | F | H | H | Ph | H |
| 12.031 | Me | F | H | H | Ph | Me |
| 12.032 | Me | Cl | H | H | Ph | H |
| 12.033 | Me | Cl | H | H | Ph | Me |
| 12.034 | Me | H | H | H | Me | H |
| 12.035 | Me | H | H | H | H | Me |
| 12.036 | Me | H | H | H | Me | Me |
| 12.037 | Et | H | H | H | H | H |
| 12.038 | Et | F | H | H | H | H |
| 12.039 | Et | F | H | H | H | Me |
| 12.040 | Et | F | H | H | Me | H |
| 12.041 | Et | F | H | H | Me | Me |
| 12.042 | Et | Cl | H | H | H | H |
| 12.043 | Et | Cl | H | H | H | Me |
| 12.044 | Et | Cl | H | H | Me | H |
| 12.045 | Et | H | H | H | Ph | H |
| 12.046 | Et | H | H | H | Ph | Me |
| 12.047 | Et | F | H | H | Ph | H |
| 12.048 | Et | F | H | H | Ph | Me |
| 12.049 | Et | Cl | H | H | Ph | H |
| 12.050 | Et | Cl | H | H | Ph | Me |
| 12.051 | Et | H | H | H | Me | H |
| 12.052 | Et | H | H | H | H | Me |
| 12.053 | Me | H | H | H | Me | Me |
| 12.054 | H | F | F | H | H | H |
| 12.055 | H | F | H | F | H | H |

TABLE 13

Compounds according to the invention of the formula (I) in which X represents CH, A represents A12, $R^3$ and $R^4$ each represent hydrogen and $R^2$ represents chlorine:

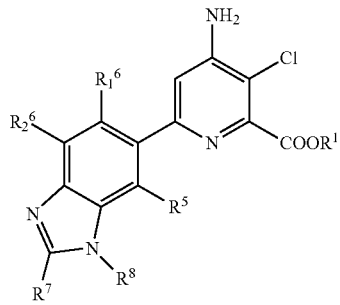

| Ex. No. | $R^1$ | $R^5$ | $R_1^6$ | $R_2^6$ | $R^7$ | $R^8$ |
|---|---|---|---|---|---|---|
| 13.001 | H | H | H | H | H | Me |
| 13.002 | H | F | H | H | H | Me |
| 13.003 | H | F | H | H | Me | Me |
| 13.004 | H | Cl | H | H | H | Me |
| 13.005 | H | Cl | H | H | Me | Me |
| 13.006 | H | H | H | H | Ph | Me |
| 13.007 | H | F | H | H | Ph | Me |
| 13.008 | H | Cl | H | H | Ph | Me |
| 13.009 | H | H | H | H | H | Me |
| 13.010 | Me | H | H | H | H | Me |
| 13.011 | Me | F | H | H | H | Me |
| 13.012 | Me | H | H | H | Me | Me |
| 13.013 | Me | F | H | H | Me | Me |
| 13.014 | Me | Cl | H | H | H | Me |
| 13.015 | Me | Cl | H | H | Me | Me |
| 13.016 | Me | H | H | H | Ph | Me |
| 13.017 | Me | F | H | H | Ph | Me |
| 13.018 | Me | Cl | H | H | Ph | Me |
| 13.019 | Et | F | H | H | H | Me |
| 13.020 | Et | F | H | H | Me | Me |
| 13.021 | Et | Cl | H | H | H | Me |
| 13.022 | Et | H | H | H | Ph | Me |
| 13.023 | Et | F | H | H | Ph | Me |
| 13.024 | Et | Cl | H | H | Ph | Me |
| 13.025 | Et | H | H | H | H | Me |
| 13.026 | Me | H | H | H | Me | Me |
| 13.027 | Et | Cl | H | H | Me | Me |
| 13.028 | H | F | F | H | H | H |
| 13.029 | H | F | H | F | H | H |

TABLE 14

Compounds according to the invention of the formula (I) in which X represents CH, A represents A13, $R^3$ and $R^4$ each represent hydrogen and $R^2$ represents chlorine:

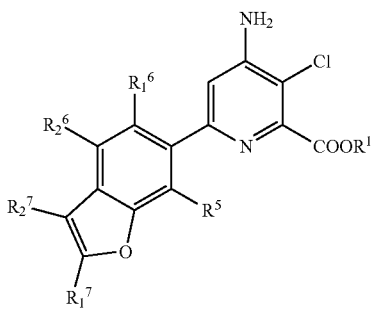

| Ex. No. | $R^1$ | $R^5$ | $R_1^6$ | $R_2^6$ | $R_1^7$ | $R_2^7$ |
|---|---|---|---|---|---|---|
| 14.001 | H | H | H | H | H | H |
| 14.002 | H | H | H | H | H | Cl |
| 14.003 | H | H | H | H | H | F |
| 14.004 | H | H | H | H | H | Me |
| 14.005 | H | H | H | H | F | H |
| 14.006 | H | H | H | H | F | Cl |
| 14.007 | H | H | H | H | F | F |
| 14.008 | H | H | H | H | F | Me |
| 14.009 | H | H | H | H | Cl | H |
| 14.010 | H | H | H | H | Cl | F |
| 14.011 | H | H | H | H | Cl | Cl |
| 14.012 | H | H | H | H | Cl | Me |
| 14.013 | H | H | H | H | Me | H |
| 14.014 | H | H | H | H | Me | Cl |
| 14.015 | H | H | H | H | Me | F |
| 14.016 | H | H | H | H | Me | Me |
| 14.017 | H | H | H | H | Ph | H |
| 14.018 | H | H | H | H | Ph | Cl |
| 14.019 | H | H | H | H | Ph | F |
| 14.020 | H | H | H | H | Ph | Me |
| 14.021 | H | F | H | H | H | H |
| 14.022 | H | F | H | H | H | Cl |
| 14.023 | H | F | H | H | H | F |
| 14.024 | H | F | H | H | H | Me |
| 14.025 | H | F | H | H | F | H |
| 14.026 | H | F | H | H | F | F |
| 14.027 | H | F | H | H | F | Cl |
| 14.028 | H | F | H | H | F | Me |
| 14.029 | H | F | H | H | Cl | H |
| 14.030 | H | F | H | H | Cl | Cl |
| 14.031 | H | F | H | H | Cl | F |
| 14.032 | H | F | H | H | Cl | Me |
| 14.033 | H | F | H | H | Me | H |
| 14.034 | H | F | H | H | Me | Cl |
| 14.035 | H | F | H | H | Me | F |
| 14.036 | H | F | H | H | Me | Me |
| 14.037 | H | F | H | H | Ph | H |
| 14.038 | H | F | H | H | Ph | Cl |
| 14.039 | H | F | H | H | Ph | F |
| 14.040 | H | F | H | H | Ph | Me |
| 14.041 | H | Cl | H | H | H | H |
| 14.042 | H | Cl | H | H | H | Cl |
| 14.043 | H | Cl | H | H | H | F |
| 14.044 | H | Cl | H | H | H | Me |
| 14.045 | H | Cl | H | H | F | H |
| 14.046 | H | Cl | H | H | F | Cl |
| 14.047 | H | Cl | H | H | F | F |
| 14.048 | H | Cl | H | H | F | Me |
| 14.049 | H | Cl | H | H | Cl | H |
| 14.050 | H | Cl | H | H | Cl | F |
| 14.051 | H | Cl | H | H | Cl | Cl |
| 14.052 | H | Cl | H | H | Cl | Me |
| 14.053 | H | Cl | H | H | Me | H |
| 14.054 | H | Cl | H | H | Me | Cl |
| 14.055 | H | Cl | H | H | Me | F |
| 14.056 | H | Cl | H | H | Me | Me |
| 14.057 | H | Cl | H | H | Ph | H |
| 14.058 | H | Cl | H | H | Ph | Cl |
| 14.059 | H | Cl | H | H | Ph | F |
| 14.060 | H | Cl | H | H | Ph | Me |
| 14.061 | Me | H | H | H | H | H |

TABLE 14-continued

Compounds according to the invention of the formula (I) in which X represents CH, A represents A13, $R^3$ and $R^4$ each represent hydrogen and $R^2$ represents chlorine:

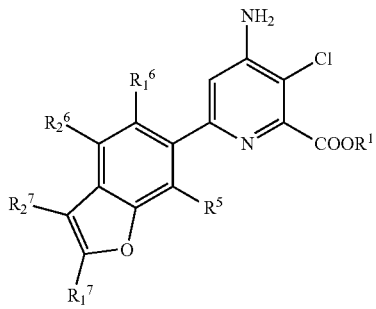

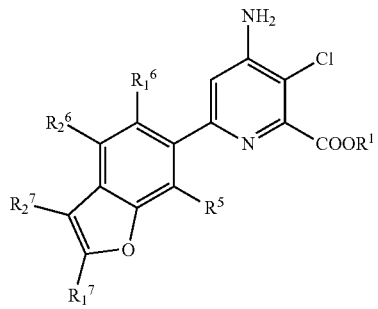

| Ex. No. | $R^1$ | $R^5$ | $R_1^6$ | $R_2^6$ | $R_1^7$ | $R_2^7$ | Ex. No. | $R^1$ | $R^5$ | $R_1^6$ | $R_2^6$ | $R_1^7$ | $R_2^7$ |
|---|---|---|---|---|---|---|---|---|---|---|---|---|---|
| 14.062 | Me | H | H | H | H | Cl | 14.120 | Me | Cl | H | H | Ph | Me |
| 14.063 | Me | H | H | H | H | F | 14.121 | Et | H | H | H | H | H |
| 14.064 | Me | H | H | H | H | Me | 14.122 | Et | H | H | H | H | Cl |
| 14.065 | Me | H | H | H | F | H | 14.123 | Et | H | H | H | H | F |
| 14.066 | Me | H | H | H | F | Cl | 14.124 | Et | H | H | H | H | Me |
| 14.067 | Me | H | H | H | F | F | 14.125 | Et | H | H | H | F | H |
| 14.068 | Me | H | H | H | F | Me | 14.126 | Et | H | H | H | F | Cl |
| 14.069 | Me | H | H | H | Cl | H | 14.127 | Et | H | H | H | F | F |
| 14.070 | Me | H | H | H | Cl | F | 14.128 | Et | H | H | H | F | Me |
| 14.071 | Me | H | H | H | Cl | Cl | 14.129 | Et | H | H | H | Cl | H |
| 14.072 | Me | H | H | H | Cl | Me | 14.130 | Et | H | H | H | Cl | F |
| 14.073 | Me | H | H | H | Me | H | 14.131 | Et | H | H | H | Cl | Cl |
| 14.074 | Me | H | H | H | Me | Cl | 14.132 | Et | H | H | H | Cl | Me |
| 14.075 | Me | H | H | H | Me | F | 14.133 | Et | H | H | H | Me | H |
| 14.076 | Me | H | H | H | Me | Me | 14.134 | Et | H | H | H | Me | Cl |
| 14.077 | Me | H | H | H | Ph | H | 14.135 | Et | H | H | H | Me | F |
| 14.078 | Me | H | H | H | Ph | Cl | 14.136 | Et | H | H | H | Me | Me |
| 14.079 | Me | H | H | H | Ph | F | 14.137 | Et | H | H | H | Ph | H |
| 14.080 | Me | H | H | H | Ph | Me | 14.138 | Et | H | H | H | Ph | Cl |
| 14.081 | Me | F | H | H | H | H | 14.139 | Et | H | H | H | Ph | F |
| 14.082 | Me | F | H | H | H | Cl | 14.140 | Et | H | H | H | Ph | Me |
| 14.083 | Me | F | H | H | H | F | 14.141 | Et | F | H | H | H | H |
| 14.084 | Me | F | H | H | H | Me | 14.142 | Et | F | H | H | H | Cl |
| 14.085 | Me | F | H | H | F | H | 14.143 | Et | F | H | H | H | F |
| 14.086 | Me | F | H | H | F | Cl | 14.144 | Et | F | H | H | H | Me |
| 14.087 | Me | F | H | H | F | F | 14.145 | Et | F | H | H | F | H |
| 14.088 | Me | F | H | H | F | Me | 14.146 | Et | F | H | H | F | Cl |
| 14.089 | Me | F | H | H | Cl | H | 14.147 | Et | F | H | H | F | F |
| 14.090 | Me | F | H | H | Cl | F | 14.148 | Et | F | H | H | F | Me |
| 14.091 | Me | F | H | H | Cl | Cl | 14.149 | Et | F | H | H | Cl | H |
| 14.092 | Me | F | H | H | Cl | Me | 14.150 | Et | F | H | H | Cl | F |
| 14.093 | Me | F | H | H | Me | H | 14.151 | Et | F | H | H | Cl | Cl |
| 14.094 | Me | F | H | H | Me | Cl | 14.152 | Et | F | H | H | Cl | Me |
| 14.095 | Me | F | H | H | Me | F | 14.153 | Et | F | H | H | Me | H |
| 14.096 | Me | F | H | H | Me | Me | 14.154 | Et | F | H | H | Me | Cl |
| 14.097 | Me | F | H | H | Ph | H | 14.155 | Et | F | H | H | Me | F |
| 14.098 | Me | F | H | H | Ph | Cl | 14.156 | Et | F | H | H | Me | Me |
| 14.099 | Me | F | H | H | Ph | F | 14.157 | Et | F | H | H | Ph | H |
| 14.100 | Me | F | H | H | Ph | Me | 14.158 | Et | F | H | H | Ph | Cl |
| 14.101 | Me | Cl | H | H | H | H | 14.159 | Et | F | H | H | Ph | F |
| 14.102 | Me | Cl | H | H | H | Cl | 14.160 | Et | F | H | H | Ph | Me |
| 14.103 | Me | Cl | H | H | H | F | 14.161 | Et | Cl | H | H | H | H |
| 14.104 | Me | Cl | H | H | H | Me | 14.162 | Et | Cl | H | H | H | Cl |
| 14.105 | Me | Cl | H | H | F | H | 14.163 | Et | Cl | H | H | H | F |
| 14.106 | Me | Cl | H | H | F | Cl | 14.164 | Et | Cl | H | H | H | Me |
| 14.107 | Me | Cl | H | H | F | F | 14.165 | Et | Cl | H | H | F | H |
| 14.108 | Me | Cl | H | H | F | Me | 14.166 | Et | Cl | H | H | F | Cl |
| 14.109 | Me | Cl | H | H | Cl | H | 14.167 | Et | Cl | H | H | F | F |
| 14.110 | Me | Cl | H | H | Cl | F | 14.168 | Et | Cl | H | H | F | Me |
| 14.111 | Me | Cl | H | H | Cl | Cl | 14.169 | Et | Cl | H | H | Cl | H |
| 14.112 | Me | Cl | H | H | Cl | Me | 14.170 | Et | Cl | H | H | Cl | F |
| 14.113 | Me | Cl | H | H | Me | H | 14.171 | Et | Cl | H | H | Cl | Cl |
| 14.114 | Me | Cl | H | H | Me | Cl | 14.172 | Et | Cl | H | H | Cl | Me |
| 14.115 | Me | Cl | H | H | Me | F | 14.173 | Et | Cl | H | H | Me | H |
| 14.116 | Me | Cl | H | H | Me | Me | 14.174 | Et | Cl | H | H | Me | Cl |
| 14.117 | Me | Cl | H | H | Ph | H | 14.175 | Et | Cl | H | H | Me | F |
| 14.118 | Me | Cl | H | H | Ph | Cl | 14.176 | Et | Cl | H | H | Me | Me |
| 14.119 | Me | Cl | H | H | Ph | F | 14.177 | Et | Cl | H | H | Ph | H |

TABLE 14-continued

Compounds according to the invention of the formula (I) in which X represents CH, A represents A13, $R^3$ and $R^4$ each represent hydrogen and $R^2$ represents chlorine:

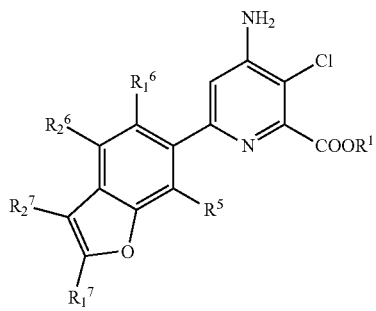

| Ex. No. | $R^1$ | $R^5$ | $R_1^6$ | $R_2^6$ | $R_1^7$ | $R_2^7$ |
|---|---|---|---|---|---|---|
| 14.178 | Et | Cl | H | H | Ph | Cl |
| 14.179 | Et | Cl | H | H | Ph | F |
| 14.180 | Et | Cl | H | H | Ph | Me |
| 14.181 | H | F | F | H | H | H |
| 14.182 | H | F | F | H | H | H |
| 14.183 | Me | H | F | H | H | H |
| 14.184 | H | H | F | H | H | H |
| 14.185 | K | H | F | H | H | H |
| 14.186 | Me | H | Cl | H | H | H |
| 14.187 | H | H | Cl | H | H | H |
| 14.188 | K | H | Cl | H | H | H |
| 14.189 | Me | H | H | F | H | H |
| 14.190 | H | H | H | F | H | H |
| 14.191 | K | H | H | F | H | H |
| 14.192 | Me | H | H | Cl | H | H |
| 14.193 | H | H | H | Cl | H | H |
| 14.194 | K | H | H | Cl | H | H |
| 14.195 | K | F | H | H | H | H |
| 14.196 | K | Cl | H | H | H | H |

TABLE 15

Compounds according to the invention of the formula (I) in which X represents CH, A represents A14, $R^3$ and $R^4$ each represent hydrogen and $R^2$ represents chlorine:

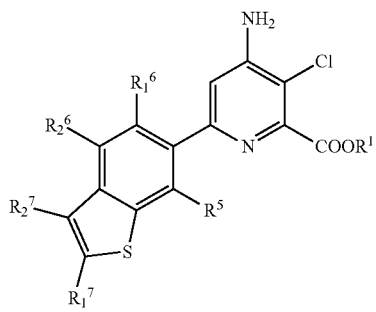

| Ex. No. | $R^1$ | $R^5$ | $R_1^6$ | $R_2^6$ | $R_1^7$ | $R_2^7$ |
|---|---|---|---|---|---|---|
| 15.001 | H | H | H | H | H | H |
| 15.002 | H | H | H | H | H | Cl |
| 15.003 | H | H | H | H | H | F |
| 15.004 | H | H | H | H | H | Me |
| 15.005 | H | H | H | H | F | H |
| 15.006 | H | H | H | H | F | Cl |
| 15.007 | H | H | H | H | F | F |
| 15.008 | H | H | H | H | F | Me |
| 15.009 | H | H | H | H | Cl | H |
| 15.010 | H | H | H | H | Cl | F |
| 15.011 | H | H | H | H | Cl | Cl |
| 15.012 | H | H | H | H | Cl | Me |
| 15.013 | H | H | H | H | Me | H |

TABLE 15-continued

Compounds according to the invention of the formula (I) in which X represents CH, A represents A14, $R^3$ and $R^4$ each represent hydrogen and $R^2$ represents chlorine:

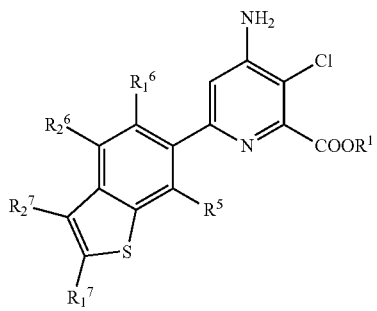

| Ex. No. | $R^1$ | $R^5$ | $R_1^6$ | $R_2^6$ | $R_1^7$ | $R_2^7$ |
|---|---|---|---|---|---|---|
| 15.014 | H | H | H | H | Me | Cl |
| 15.015 | H | H | H | H | Me | F |
| 15.016 | H | H | H | H | Me | Me |
| 15.017 | H | H | H | H | Ph | H |
| 15.018 | H | H | H | H | Ph | Cl |
| 15.019 | H | H | H | H | Ph | F |
| 15.020 | H | H | H | H | Ph | Me |
| 15.021 | H | F | H | H | H | H |
| 15.022 | H | F | H | H | H | Cl |
| 15.023 | H | F | H | H | H | F |
| 15.024 | H | F | H | H | H | Me |
| 15.025 | H | F | H | H | F | H |
| 15.026 | H | F | H | H | F | Cl |
| 15.027 | H | F | H | H | F | F |
| 15.028 | H | F | H | H | F | Me |
| 15.029 | H | F | H | H | Cl | H |
| 15.030 | H | F | H | H | Cl | F |
| 15.031 | H | F | H | H | Cl | Cl |
| 15.032 | H | F | H | H | Cl | Me |
| 15.033 | H | F | H | H | Me | H |
| 15.034 | H | F | H | H | Me | Cl |
| 15.035 | H | F | H | H | Me | F |
| 15.036 | H | F | H | H | Me | Me |
| 15.037 | H | F | H | H | Ph | H |
| 15.038 | H | F | H | H | Ph | Cl |
| 15.039 | H | F | H | H | Ph | F |
| 15.040 | H | F | H | H | Ph | Me |
| 15.041 | H | Cl | H | H | H | H |
| 15.042 | H | Cl | H | H | H | Cl |
| 15.043 | H | Cl | H | H | H | F |
| 15.044 | H | Cl | H | H | H | Me |
| 15.045 | H | Cl | H | H | F | H |
| 15.046 | H | Cl | H | H | F | Cl |
| 15.047 | H | Cl | H | H | F | F |
| 15.048 | H | Cl | H | H | F | Me |
| 15.049 | H | Cl | H | H | Cl | H |
| 15.050 | H | Cl | H | H | Cl | F |
| 15.051 | H | Cl | H | H | Cl | Cl |
| 15.052 | H | Cl | H | H | Cl | Me |
| 15.053 | H | Cl | H | H | Me | H |
| 15.054 | H | Cl | H | H | Me | Cl |
| 15.055 | H | Cl | H | H | Me | F |
| 15.056 | H | Cl | H | H | Me | Me |
| 15.057 | H | Cl | H | H | Ph | H |
| 15.058 | H | Cl | H | H | Ph | Cl |
| 15.059 | H | Cl | H | H | Ph | F |
| 15.060 | H | Cl | H | H | Ph | Me |
| 15.061 | Me | H | H | H | H | H |
| 15.062 | Me | H | H | H | H | Cl |
| 15.063 | Me | H | H | H | H | F |
| 15.064 | Me | H | H | H | H | Me |
| 15.065 | Me | H | H | H | F | H |
| 15.066 | Me | H | H | H | F | Cl |
| 15.067 | Me | H | H | H | F | F |
| 15.068 | Me | H | H | H | F | Me |
| 15.069 | Me | H | H | H | Cl | H |
| 15.070 | Me | H | H | H | Cl | F |
| 15.071 | Me | H | H | H | Cl | Cl |

TABLE 15-continued

Compounds according to the invention of the formula (I) in which X represents CH, A represents A14, $R^3$ and $R^4$ each represent hydrogen and $R^2$ represents chlorine:

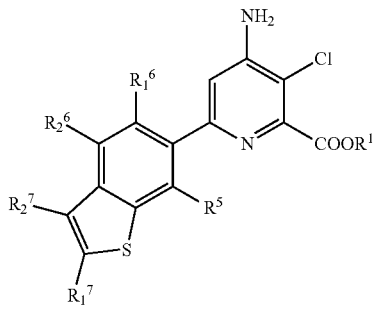

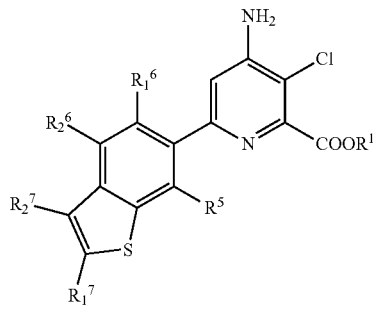

| Ex. No. | $R^1$ | $R^5$ | $R_1^6$ | $R_2^6$ | $R_1^7$ | $R_2^7$ | Ex. No. | $R^1$ | $R^5$ | $R_1^6$ | $R_2^6$ | $R_1^7$ | $R_2^7$ |
|---|---|---|---|---|---|---|---|---|---|---|---|---|---|
| 15.072 | Me | H | H | H | Cl | Me | 15.130 | Et | H | H | H | Cl | F |
| 15.073 | Me | H | H | H | Me | H | 15.131 | Et | H | H | H | Cl | Cl |
| 15.074 | Me | H | H | H | Me | Cl | 15.132 | Et | H | H | H | Cl | Me |
| 15.075 | Me | H | H | H | Me | F | 15.133 | Et | H | H | H | Me | H |
| 15.076 | Me | H | H | H | Me | Me | 15.134 | Et | H | H | H | Me | Cl |
| 15.077 | Me | H | H | H | Ph | H | 15.135 | Et | H | H | H | Me | F |
| 15.078 | Me | H | H | H | Ph | Cl | 15.136 | Et | H | H | H | Me | Me |
| 15.079 | Me | H | H | H | Ph | F | 15.137 | Et | H | H | H | Ph | H |
| 15.080 | Me | H | H | H | Ph | Me | 15.138 | Et | H | H | H | Ph | Cl |
| 15.081 | Me | F | H | H | H | H | 15.139 | Et | H | H | H | Ph | F |
| 15.082 | Me | F | H | H | H | Cl | 15.140 | Et | H | H | H | Ph | Me |
| 15.083 | Me | F | H | H | H | F | 15.141 | Et | F | H | H | H | H |
| 15.084 | Me | F | H | H | H | Me | 15.142 | Et | F | H | H | H | Cl |
| 15.085 | Me | F | H | H | F | H | 15.143 | Et | F | H | H | H | F |
| 15.086 | Me | F | H | H | F | Cl | 15.144 | Et | F | H | H | H | Me |
| 15.087 | Me | F | H | H | F | F | 15.145 | Et | F | H | H | F | H |
| 15.088 | Me | F | H | H | F | Me | 15.146 | Et | F | H | H | F | Cl |
| 15.089 | Me | F | H | H | Cl | H | 15.147 | Et | F | H | H | F | F |
| 15.090 | Me | F | H | H | Cl | F | 15.148 | Et | F | H | H | F | Me |
| 15.091 | Me | F | H | H | Cl | Cl | 15.149 | Et | F | H | H | Cl | H |
| 15.092 | Me | F | H | H | Cl | Me | 15.150 | Et | F | H | H | Cl | F |
| 15.093 | Me | F | H | H | Me | H | 15.151 | Et | F | H | H | Cl | Cl |
| 15.094 | Me | F | H | H | Me | Cl | 15.152 | Et | F | H | H | Cl | Me |
| 15.095 | Me | F | H | H | Me | F | 15.153 | Et | F | H | H | Me | H |
| 15.096 | Me | F | H | H | Me | Me | 15.154 | Et | F | H | H | Me | Cl |
| 15.097 | Me | F | H | H | Ph | H | 15.155 | Et | F | H | H | Me | F |
| 15.098 | Me | F | H | H | Ph | Cl | 15.156 | Et | F | H | H | Me | Me |
| 15.099 | Me | F | H | H | Ph | F | 15.157 | Et | F | H | H | Ph | H |
| 15.100 | Me | F | H | H | Ph | Me | 15.158 | Et | F | H | H | Ph | Cl |
| 15.101 | Me | Cl | H | H | H | H | 15.159 | Et | F | H | H | Ph | F |
| 15.102 | Me | Cl | H | H | H | Cl | 15.160 | Et | F | H | H | Ph | Me |
| 15.103 | Me | Cl | H | H | H | F | 15.161 | Et | Cl | H | H | H | H |
| 15.104 | Me | Cl | H | H | H | Me | 15.162 | Et | Cl | H | H | H | Cl |
| 15.105 | Me | Cl | H | H | F | H | 15.163 | Et | Cl | H | H | H | F |
| 15.106 | Me | Cl | H | H | F | Cl | 15.164 | Et | Cl | H | H | H | Me |
| 15.107 | Me | Cl | H | H | F | F | 15.165 | Et | Cl | H | H | F | H |
| 15.108 | Me | Cl | H | H | F | Me | 15.166 | Et | Cl | H | H | F | Cl |
| 15.109 | Me | Cl | H | H | Cl | H | 15.167 | Et | Cl | H | H | F | F |
| 15.110 | Me | Cl | H | H | Cl | F | 15.168 | Et | Cl | H | H | F | Me |
| 15.111 | Me | Cl | H | H | Cl | Cl | 15.169 | Et | Cl | H | H | Cl | H |
| 15.112 | Me | Cl | H | H | Cl | Me | 15.170 | Et | Cl | H | H | Cl | F |
| 15.113 | Me | Cl | H | H | Me | H | 15.171 | Et | Cl | H | H | Cl | Cl |
| 15.114 | Me | Cl | H | H | Me | Cl | 15.172 | Et | Cl | H | H | Cl | Me |
| 15.115 | Me | Cl | H | H | Me | F | 15.173 | Et | Cl | H | H | Me | H |
| 15.116 | Me | Cl | H | H | Me | Me | 15.174 | Et | Cl | H | H | Me | Cl |
| 15.117 | Me | Cl | H | H | Ph | H | 15.175 | Et | Cl | H | H | Me | F |
| 15.118 | Me | Cl | H | H | Ph | Cl | 15.176 | Et | Cl | H | H | Me | Me |
| 15.119 | Me | Cl | H | H | Ph | F | 15.177 | Et | Cl | H | H | Ph | H |
| 15.120 | Me | Cl | H | H | Ph | Me | 15.178 | Et | Cl | H | H | Ph | Cl |
| 15.121 | Et | H | H | H | H | H | 15.179 | Et | Cl | H | H | Ph | F |
| 15.122 | Et | H | H | H | H | Cl | 15.180 | Et | Cl | H | H | Ph | Me |
| 15.123 | Et | H | H | H | H | F | 15.181 | H | F | F | H | H | H |
| 15.124 | Et | H | H | H | H | Me | 15.182 | H | F | H | F | H | H |
| 15.125 | Et | H | H | H | F | H | 15.183 | Me | H | F | H | H | H |
| 15.126 | Et | H | H | H | F | Cl | 15.184 | H | H | F | H | H | H |
| 15.127 | Et | H | H | H | F | F | 15.185 | K | H | F | H | H | H |
| 15.128 | Et | H | H | H | F | Me | 15.186 | Me | H | Cl | H | H | H |
| 15.129 | Et | H | H | H | Cl | H | 15.187 | H | H | Cl | H | H | H |

TABLE 15-continued

Compounds according to the invention of the formula (I) in which X represents CH, A represents A14, $R^3$ and $R^4$ each represent hydrogen and $R^2$ represents chlorine:

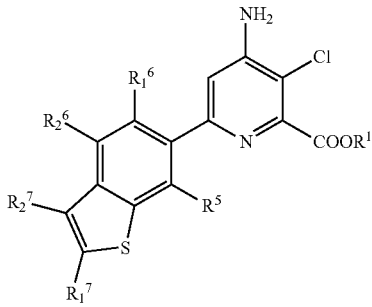

| Ex. No. | $R^1$ | $R^5$ | $R_1^6$ | $R_2^6$ | $R_1^7$ | $R_2^7$ |
|---|---|---|---|---|---|---|
| 15.188 | K | H | Cl | H | H | H |
| 15.189 | Me | H | H | F | H | H |
| 15.190 | H | H | H | F | H | H |
| 15.191 | K | H | H | F | H | H |
| 15.192 | Me | H | H | Cl | H | H |
| 15.193 | H | H | H | Cl | H | H |
| 15.194 | K | H | H | Cl | H | H |
| 15.195 | K | F | H | H | H | H |
| 15.196 | K | Cl | H | H | H | H |

TABLE 16

Compounds according to the invention of the formula (I) in which X represents CH, A represents A15, $R^8$, $R^3$ and $R^4$ each represent hydrogen and $R^2$ represents chlorine:

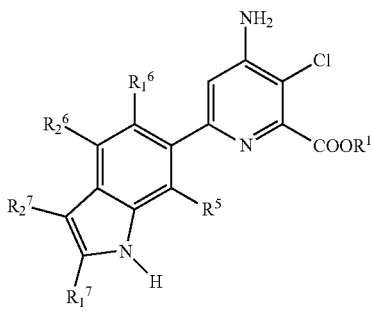

| Ex. No. | $R^1$ | $R^5$ | $R_1^6$ | $R_2^6$ | $R_1^7$ | $R_2^7$ |
|---|---|---|---|---|---|---|
| 16.001 | H | H | H | H | H | H |
| 16.002 | H | H | H | H | H | Cl |
| 16.003 | H | H | H | H | H | F |
| 16.004 | H | H | H | H | H | Me |
| 16.005 | H | H | H | H | F | H |
| 16.006 | H | H | H | H | F | Cl |
| 16.007 | H | H | H | H | F | F |
| 16.008 | H | H | H | H | F | Me |
| 16.009 | H | H | H | H | Cl | H |
| 16.010 | H | H | H | H | Cl | F |
| 16.011 | H | H | H | H | Cl | Cl |
| 16.012 | H | H | H | H | Cl | Me |
| 16.013 | H | H | H | H | Me | H |
| 16.014 | H | H | H | H | Me | Cl |
| 16.015 | H | H | H | H | Me | F |
| 16.016 | H | H | H | H | Me | Me |
| 16.017 | H | H | H | H | Ph | H |
| 16.018 | H | H | H | H | Ph | Cl |
| 16.019 | H | H | H | H | Ph | F |
| 16.020 | H | H | H | H | Ph | Me |
| 16.021 | H | F | H | H | H | H |
| 16.022 | H | F | H | H | H | Cl |
| 16.023 | H | F | H | H | H | F |
| 16.024 | H | F | H | H | H | Me |
| 16.025 | H | F | H | H | F | H |
| 16.026 | H | F | H | H | F | Cl |
| 16.027 | H | F | H | H | F | F |
| 16.028 | H | F | H | H | F | Me |
| 16.029 | H | F | H | H | Cl | H |
| 16.030 | H | F | H | H | Cl | F |
| 16.031 | H | F | H | H | Cl | Cl |
| 16.032 | H | F | H | H | Cl | Me |
| 16.033 | H | F | H | H | Me | H |
| 16.034 | H | F | H | H | Me | Cl |
| 16.035 | H | F | H | H | Me | F |
| 16.036 | H | F | H | H | Me | Me |
| 16.037 | H | F | H | H | Ph | H |
| 16.038 | H | F | H | H | Ph | Cl |
| 16.039 | H | F | H | H | Ph | F |
| 16.040 | H | F | H | H | Ph | Me |
| 16.041 | H | Cl | H | H | H | H |
| 16.042 | H | Cl | H | H | H | Cl |
| 16.043 | H | Cl | H | H | H | F |
| 16.044 | H | Cl | H | H | H | Me |
| 16.045 | H | Cl | H | H | F | H |
| 16.046 | H | Cl | H | H | F | Cl |
| 16.047 | H | Cl | H | H | F | F |
| 16.048 | H | Cl | H | H | F | Me |
| 16.049 | H | Cl | H | H | Cl | H |
| 16.050 | H | Cl | H | H | Cl | F |
| 16.051 | H | Cl | H | H | Cl | Cl |
| 16.052 | H | Cl | H | H | Cl | Me |
| 16.053 | H | Cl | H | H | Me | H |
| 16.054 | H | Cl | H | H | Me | Cl |
| 16.055 | H | Cl | H | H | Me | F |
| 16.056 | H | Cl | H | H | Me | Me |
| 16.057 | H | Cl | H | H | Ph | H |
| 16.058 | H | Cl | H | H | Ph | Cl |
| 16.059 | H | Cl | H | H | Ph | F |
| 16.060 | H | Cl | H | H | Ph | Me |
| 16.061 | Me | H | H | H | H | H |
| 16.062 | Me | H | H | H | H | Cl |
| 16.063 | Me | H | H | H | H | F |
| 16.064 | Me | H | H | H | H | Me |
| 16.065 | Me | H | H | H | F | H |
| 16.066 | Me | H | H | H | F | Cl |
| 16.067 | Me | H | H | H | F | F |
| 16.068 | Me | H | H | H | F | Me |
| 16.069 | Me | H | H | H | Cl | H |
| 16.070 | Me | H | H | H | Cl | F |
| 16.071 | Me | H | H | H | Cl | Cl |
| 16.072 | Me | H | H | H | Cl | Me |
| 16.073 | Me | H | H | H | Me | H |
| 16.074 | Me | H | H | H | Me | Cl |
| 16.075 | Me | H | H | H | Me | F |
| 16.076 | Me | H | H | H | Me | Me |
| 16.077 | Me | H | H | H | Ph | H |
| 16.078 | Me | H | H | H | Ph | Cl |
| 16.079 | Me | H | H | H | Ph | F |
| 16.080 | Me | H | H | H | Ph | Me |
| 16.081 | Me | F | H | H | H | H |

TABLE 16-continued

Compounds according to the invention of the formula (I) in which X represents CH, A represents A15, $R^8$, $R^3$ and $R^4$ each represent hydrogen and $R^2$ represents chlorine:

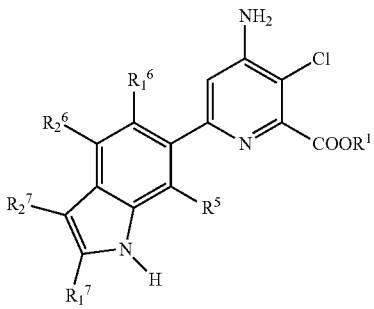

| Ex. No. | $R^1$ | $R^5$ | $R_1^6$ | $R_2^6$ | $R_1^7$ | $R_2^7$ |
|---|---|---|---|---|---|---|
| 16.082 | Me | F | H | H | H | Cl |
| 16.083 | Me | F | H | H | H | F |
| 16.084 | Me | F | H | H | H | Me |
| 16.085 | Me | F | H | H | F | H |
| 16.086 | Me | F | H | H | F | Cl |
| 16.087 | Me | F | H | H | F | F |
| 16.088 | Me | F | H | H | F | Me |
| 16.089 | Me | F | H | H | Cl | H |
| 16.090 | Me | F | H | H | Cl | F |
| 16.091 | Me | F | H | H | Cl | Cl |
| 16.092 | Me | F | H | H | Cl | Me |
| 16.093 | Me | F | H | H | Me | H |
| 16.094 | Me | F | H | H | Me | Cl |
| 16.095 | Me | F | H | H | Me | F |
| 16.096 | Me | F | H | H | Me | Me |
| 16.097 | Me | F | H | H | Ph | H |
| 16.098 | Me | F | H | H | Ph | Cl |
| 16.099 | Me | F | H | H | Ph | F |
| 16.100 | Me | F | H | H | Ph | Me |
| 16.101 | Me | Cl | H | H | H | H |
| 16.102 | Me | Cl | H | H | H | Cl |
| 16.103 | Me | Cl | H | H | H | F |
| 16.104 | Me | Cl | H | H | H | Me |
| 16.105 | Me | Cl | H | H | F | H |
| 16.106 | Me | Cl | H | H | F | Cl |
| 16.107 | Me | Cl | H | H | F | F |
| 16.108 | Me | Cl | H | H | F | Me |
| 16.109 | Me | Cl | H | H | Cl | H |
| 16.110 | Me | Cl | H | H | Cl | F |
| 16.111 | Me | Cl | H | H | Cl | Cl |
| 16.112 | Me | Cl | H | H | Cl | Me |
| 16.113 | Me | Cl | H | H | Me | H |
| 16.114 | Me | Cl | H | H | Me | Cl |
| 16.115 | Me | Cl | H | H | Me | F |
| 16.116 | Me | Cl | H | H | Me | Me |
| 16.117 | Me | Cl | H | H | Ph | H |
| 16.118 | Me | Cl | H | H | Ph | Cl |
| 16.119 | Me | Cl | H | H | Ph | F |
| 16.120 | Me | Cl | H | H | Ph | Me |
| 16.121 | Et | H | H | H | H | H |
| 16.122 | Et | H | H | H | H | Cl |
| 16.123 | Et | H | H | H | H | F |
| 16.124 | Et | H | H | H | H | Me |
| 16.125 | Et | H | H | H | F | H |
| 16.126 | Et | H | H | H | F | Cl |
| 16.127 | Et | H | H | H | F | F |
| 16.128 | Et | H | H | H | F | Me |
| 16.129 | Et | H | H | H | Cl | H |
| 16.130 | Et | H | H | H | Cl | F |
| 16.131 | Et | H | H | H | Cl | Cl |
| 16.132 | Et | H | H | H | Cl | Me |
| 16.133 | Et | H | H | H | Me | H |
| 16.134 | Et | H | H | H | Me | Cl |
| 16.135 | Et | H | H | H | Me | F |
| 16.136 | Et | H | H | H | Me | Me |
| 16.137 | Et | H | H | H | Ph | H |
| 16.138 | Et | H | H | H | Ph | Cl |
| 16.139 | Et | H | H | H | Ph | F |
| 16.140 | Et | H | H | H | Ph | Me |
| 16.141 | Et | F | H | H | H | H |
| 16.142 | Et | F | H | H | H | Cl |
| 16.143 | Et | F | H | H | H | F |
| 16.144 | Et | F | H | H | H | Me |
| 16.145 | Et | F | H | H | F | H |
| 16.146 | Et | F | H | H | F | Cl |
| 16.147 | Et | F | H | H | F | F |
| 16.148 | Et | F | H | H | F | Me |
| 16.149 | Et | F | H | H | Cl | H |
| 16.150 | Et | F | H | H | Cl | F |
| 16.151 | Et | F | H | H | Cl | Cl |
| 16.152 | Et | F | H | H | Cl | Me |
| 16.153 | Et | F | H | H | Me | H |
| 16.154 | Et | F | H | H | Me | Cl |
| 16.155 | Et | F | H | H | Me | F |
| 16.156 | Et | F | H | H | Me | Me |
| 16.157 | Et | F | H | H | Ph | H |
| 16.158 | Et | F | H | H | Ph | Cl |
| 16.159 | Et | F | H | H | Ph | F |
| 16.160 | Et | F | H | H | Ph | Me |
| 16.161 | Et | Cl | H | H | H | H |
| 16.162 | Et | Cl | H | H | H | Cl |
| 16.163 | Et | Cl | H | H | H | F |
| 16.164 | Et | Cl | H | H | H | Me |
| 16.165 | Et | Cl | H | H | F | H |
| 16.166 | Et | Cl | H | H | F | Cl |
| 16.167 | Et | Cl | H | H | F | F |
| 16.168 | Et | Cl | H | H | F | Me |
| 16.169 | Et | Cl | H | H | Cl | H |
| 16.170 | Et | Cl | H | H | Cl | F |
| 16.171 | Et | Cl | H | H | Cl | Cl |
| 16.172 | Et | Cl | H | H | Cl | Me |
| 16.173 | Et | Cl | H | H | Me | H |
| 16.174 | Et | Cl | H | H | Me | Cl |
| 16.175 | Et | Cl | H | H | Me | F |
| 16.176 | Et | Cl | H | H | Me | Me |
| 16.177 | Et | Cl | H | H | Ph | H |
| 16.178 | Et | Cl | H | H | Ph | Cl |
| 16.179 | Et | Cl | H | H | Ph | F |
| 16.180 | Et | Cl | H | H | Ph | Me |
| 16.181 | H | F | F | H | H | H |
| 16.182 | H | F | H | F | H | H |

TABLE 17

Compounds according to the invention of the formula (I) in which X represents CH, A represents A15, $R^8$ represents methyl, $R^3$ and $R^4$ each represent hydrogen and $R^2$ represents chlorine:

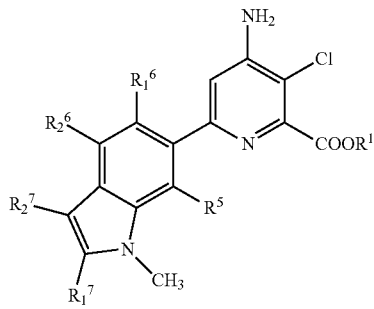

| Ex. No. | $R^1$ | $R^5$ | $R_1^6$ | $R_2^6$ | $R_1^7$ | $R_2^7$ |
|---|---|---|---|---|---|---|
| 17.001 | H | H | H | H | H | H |
| 17.002 | H | H | H | H | H | Cl |
| 17.003 | H | H | H | H | H | F |
| 17.004 | H | H | H | H | H | Me |
| 17.005 | H | H | H | H | F | H |
| 17.006 | H | H | H | H | F | Cl |
| 17.007 | H | H | H | H | F | F |
| 17.008 | H | H | H | H | F | Me |
| 17.009 | H | H | H | H | Cl | H |
| 17.010 | H | H | H | H | Cl | F |
| 17.011 | H | H | H | H | Cl | Cl |
| 17.012 | H | H | H | H | Cl | Me |
| 17.013 | H | H | H | H | Me | H |
| 17.014 | H | H | H | H | Me | Cl |
| 17.015 | H | H | H | H | Me | F |
| 17.016 | H | H | H | H | Me | Me |
| 17.017 | H | H | H | H | Ph | H |
| 17.018 | H | H | H | H | Ph | Cl |
| 17.019 | H | H | H | H | Ph | F |
| 17.020 | H | H | H | H | Ph | Me |
| 17.021 | H | F | H | H | H | H |
| 17.022 | H | F | H | H | H | Cl |
| 17.023 | H | F | H | H | H | F |
| 17.024 | H | F | H | H | H | Me |
| 17.025 | H | F | H | H | F | H |
| 17.026 | H | F | H | H | F | Cl |
| 17.027 | H | F | H | H | F | F |
| 17.028 | H | F | H | H | F | Me |
| 17.029 | H | F | H | H | Cl | H |
| 17.030 | H | F | H | H | Cl | F |
| 17.031 | H | F | H | H | Cl | Cl |
| 17.032 | H | F | H | H | Cl | Me |
| 17.033 | H | F | H | H | Me | H |
| 17.034 | H | F | H | H | Me | Cl |
| 17.035 | H | F | H | H | Me | F |
| 17.036 | H | F | H | H | Me | Me |
| 17.037 | H | F | H | H | Ph | H |
| 17.038 | H | F | H | H | Ph | Cl |
| 17.039 | H | F | H | H | Ph | F |
| 17.040 | H | F | H | H | Ph | Me |
| 17.041 | H | Cl | H | H | H | H |
| 17.042 | H | Cl | H | H | H | Cl |
| 17.043 | H | Cl | H | H | H | F |
| 17.044 | H | Cl | H | H | H | Me |
| 17.045 | H | Cl | H | H | F | H |
| 17.046 | H | Cl | H | H | F | Cl |
| 17.047 | H | Cl | H | H | F | F |
| 17.048 | H | Cl | H | H | F | Me |
| 17.049 | H | Cl | H | H | Cl | H |
| 17.050 | H | Cl | H | H | Cl | F |
| 17.051 | H | Cl | H | H | Cl | Cl |
| 17.052 | H | Cl | H | H | Cl | Me |
| 17.053 | H | Cl | H | H | Me | H |
| 17.054 | H | Cl | H | H | Me | Cl |
| 17.055 | H | Cl | H | H | Me | F |
| 17.056 | H | Cl | H | H | Me | Me |
| 17.057 | H | Cl | H | H | Ph | H |
| 17.058 | H | Cl | H | H | Ph | Cl |
| 17.059 | H | Cl | H | H | Ph | F |
| 17.060 | H | Cl | H | H | Ph | Me |
| 17.061 | Me | H | H | H | H | H |
| 17.062 | Me | H | H | H | H | Cl |
| 17.063 | Me | H | H | H | H | F |
| 17.064 | Me | H | H | H | H | Me |
| 17.065 | Me | H | H | H | F | H |
| 17.066 | Me | H | H | H | F | Cl |
| 17.067 | Me | H | H | H | F | F |
| 17.068 | Me | H | H | H | F | Me |
| 17.069 | Me | H | H | H | Cl | H |
| 17.070 | Me | H | H | H | Cl | F |
| 17.071 | Me | H | H | H | Cl | Cl |
| 17.072 | Me | H | H | H | Cl | Me |
| 17.073 | Me | H | H | H | Me | H |
| 17.074 | Me | H | H | H | Me | Cl |
| 17.075 | Me | H | H | H | Me | F |
| 17.076 | Me | H | H | H | Me | Me |
| 17.077 | Me | H | H | H | Ph | H |
| 17.078 | Me | H | H | H | Ph | Cl |
| 17.079 | Me | H | H | H | Ph | F |
| 17.080 | Me | H | H | H | Ph | Me |
| 17.081 | Me | F | H | H | H | H |
| 17.082 | Me | F | H | H | H | Cl |
| 17.083 | Me | F | H | H | H | F |
| 17.084 | Me | F | H | H | H | Me |
| 17.085 | Me | F | H | H | F | H |
| 17.086 | Me | F | H | H | F | Cl |
| 17.087 | Me | F | H | H | F | F |
| 17.088 | Me | F | H | H | F | Me |
| 17.089 | Me | F | H | H | Cl | H |
| 17.090 | Me | F | H | H | Cl | F |
| 17.091 | Me | F | H | H | Cl | Cl |
| 17.092 | Me | F | H | H | Cl | Me |
| 17.093 | Me | F | H | H | Me | H |
| 17.094 | Me | F | H | H | Me | Cl |
| 17.095 | Me | F | H | H | Me | F |
| 17.096 | Me | F | H | H | Me | Me |
| 17.097 | Me | F | H | H | Ph | H |
| 17.098 | Me | F | H | H | Ph | Cl |
| 17.099 | Me | F | H | H | Ph | F |
| 17.100 | Me | F | H | H | Ph | Me |
| 17.101 | Me | Cl | H | H | H | H |
| 17.102 | Me | Cl | H | H | H | Cl |
| 17.103 | Me | Cl | H | H | H | F |
| 17.104 | Me | Cl | H | H | H | Me |
| 17.105 | Me | Cl | H | H | F | H |
| 17.106 | Me | Cl | H | H | F | Cl |
| 17.107 | Me | Cl | H | H | F | F |
| 17.108 | Me | Cl | H | H | F | Me |
| 17.109 | Me | Cl | H | H | Cl | H |
| 17.110 | Me | Cl | H | H | Cl | F |
| 17.111 | Me | Cl | H | H | Cl | Cl |
| 17.112 | Me | Cl | H | H | Cl | Me |
| 17.113 | Me | Cl | H | H | Me | H |
| 17.114 | Me | Cl | H | H | Me | Cl |
| 17.115 | Me | Cl | H | H | Me | F |
| 17.116 | Me | Cl | H | H | Me | Me |

TABLE 17-continued

Compounds according to the invention of the formula (I) in which X represents CH, A represents A15, $R^8$ represents methyl, $R^3$ and $R^4$ each represent hydrogen and $R^2$ represents chlorine:

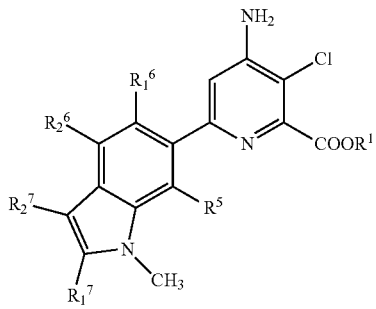

| Ex. No. | $R^1$ | $R^5$ | $R_1^6$ | $R_2^6$ | $R_1^7$ | $R_2^7$ |
|---|---|---|---|---|---|---|
| 17.117 | Me | Cl | H | H | Ph | H |
| 17.118 | Me | Cl | H | H | Ph | Cl |
| 17.119 | Me | Cl | H | H | Ph | F |
| 17.120 | Me | Cl | H | H | Ph | Me |
| 17.121 | Et | H | H | H | H | H |
| 17.122 | Et | H | H | H | H | Cl |
| 17.123 | Et | H | H | H | H | F |
| 17.124 | Et | H | H | H | H | Me |
| 17.125 | Et | H | H | H | F | H |
| 17.126 | Et | H | H | H | F | Cl |
| 17.127 | Et | H | H | H | F | F |
| 17.128 | Et | H | H | H | F | Me |
| 17.129 | Et | H | H | H | Cl | H |
| 17.130 | Et | H | H | H | Cl | F |
| 17.131 | Et | H | H | H | Cl | Cl |
| 17.132 | Et | H | H | H | Cl | Me |
| 17.133 | Et | H | H | H | Me | H |
| 17.134 | Et | H | H | H | Me | Cl |
| 17.135 | Et | H | H | H | Me | F |
| 17.136 | Et | H | H | H | Me | Me |
| 17.137 | Et | H | H | H | Ph | H |
| 17.138 | Et | H | H | H | Ph | Cl |
| 17.139 | Et | H | H | H | Ph | F |
| 17.140 | Et | H | H | H | Ph | Me |
| 17.141 | Et | F | H | H | H | H |
| 17.142 | Et | F | H | H | H | Cl |
| 17.143 | Et | F | H | H | H | F |
| 17.144 | Et | F | H | H | H | Me |
| 17.145 | Et | F | H | H | F | H |
| 17.146 | Et | F | H | H | F | Cl |
| 17.147 | Et | F | H | H | F | F |
| 17.148 | Et | F | H | H | F | Me |
| 17.149 | Et | F | H | H | Cl | H |
| 17.150 | Et | F | H | H | Cl | F |
| 17.151 | Et | F | H | H | Cl | Cl |
| 17.152 | Et | F | H | H | Cl | Me |
| 17.153 | Et | F | H | H | Me | H |
| 17.154 | Et | F | H | H | Me | Cl |
| 17.155 | Et | F | H | H | Me | F |
| 17.156 | Et | F | H | H | Me | Me |
| 17.157 | Et | F | H | H | Ph | H |
| 17.158 | Et | F | H | H | Ph | Cl |
| 17.159 | Et | F | H | H | Ph | F |
| 17.160 | Et | F | H | H | Ph | Me |
| 17.161 | Et | Cl | H | H | H | H |
| 17.162 | Et | Cl | H | H | H | Cl |
| 17.163 | Et | Cl | H | H | H | F |
| 17.164 | Et | Cl | H | H | H | Me |
| 17.165 | Et | Cl | H | H | F | H |
| 17.166 | Et | Cl | H | H | F | Cl |
| 17.167 | Et | Cl | H | H | F | F |
| 17.168 | Et | Cl | H | H | F | Me |
| 17.169 | Et | Cl | H | H | Cl | H |
| 17.170 | Et | Cl | H | H | Cl | F |
| 17.171 | Et | Cl | H | H | Cl | Cl |
| 17.172 | Et | Cl | H | H | Cl | Me |
| 17.173 | Et | Cl | H | H | Me | H |
| 17.174 | Et | Cl | H | H | Me | Cl |

TABLE 17-continued

Compounds according to the invention of the formula (I) in which X represents CH, A represents A15, $R^8$ represents methyl, $R^3$ and $R^4$ each represent hydrogen and $R^2$ represents chlorine:

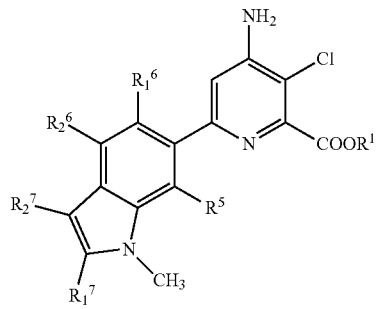

| Ex. No. | $R^1$ | $R^5$ | $R_1^6$ | $R_2^6$ | $R_1^7$ | $R_2^7$ |
|---|---|---|---|---|---|---|
| 17.175 | Et | Cl | H | H | Me | F |
| 17.176 | Et | Cl | H | H | Me | Me |
| 17.177 | Et | Cl | H | H | Ph | H |
| 17.178 | Et | Cl | H | H | Ph | Cl |
| 17.179 | Et | Cl | H | H | Ph | F |
| 17.180 | Et | Cl | H | H | Ph | Me |
| 17.181 | H | F | F | H | H | H |
| 17.182 | H | F | H | F | H | H |

TABLE 18

Compounds according to the invention of the formula (I) in which X represents CH, A represents A16, $R^3$ and $R^4$ each represent hydrogen and $R^2$ represents chlorine:

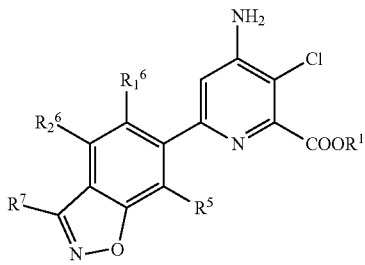

| Ex. No. | $R^1$ | $R^5$ | $R_1^6$ | $R_2^6$ | $R^7$ |
|---|---|---|---|---|---|
| 18.001 | H | H | H | H | H |
| 18.002 | H | H | H | H | Me |
| 18.003 | H | H | H | H | Ph |
| 18.004 | H | H | H | H | F |
| 18.005 | H | H | H | H | Cl |
| 18.006 | H | Cl | H | H | H |
| 18.007 | H | Cl | H | H | Me |
| 18.008 | H | Cl | H | H | Ph |
| 18.009 | H | Cl | H | H | F |
| 18.010 | H | Cl | H | H | Cl |
| 18.011 | H | F | H | H | H |
| 18.012 | H | F | H | H | Me |
| 18.013 | H | F | H | H | Ph |
| 18.014 | H | F | H | H | F |
| 18.015 | H | F | H | H | Cl |
| 18.016 | Me | H | H | H | H |
| 18.017 | Me | H | H | H | Me |
| 18.018 | Me | H | H | H | Ph |
| 18.019 | Me | H | H | H | F |
| 18.020 | Me | H | H | H | Cl |
| 18.021 | Me | Cl | H | H | H |
| 18.022 | Me | Cl | H | H | Me |
| 18.023 | Me | Cl | H | H | Ph |
| 18.024 | Me | Cl | H | H | F |
| 18.025 | Me | Cl | H | H | Cl |
| 18.026 | Et | H | H | H | H |

TABLE 18-continued

Compounds according to the invention of the formula (I) in which X represents CH, A represents A16, $R^3$ and $R^4$ each represent hydrogen and $R^2$ represents chlorine:

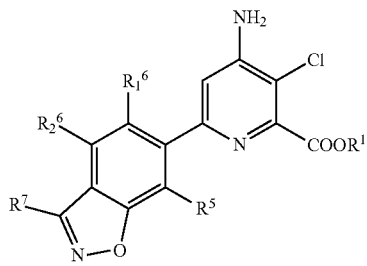

| Ex. No. | $R^1$ | $R^5$ | $R_1^6$ | $R_2^6$ | $R^7$ |
|---|---|---|---|---|---|
| 18.027 | Et | H | H | H | Me |
| 18.028 | Et | H | H | H | Ph |
| 18.029 | Et | H | H | H | F |
| 18.030 | Et | H | H | H | Cl |
| 18.031 | Et | F | H | H | H |
| 18.032 | Et | F | H | H | Me |
| 18.033 | Et | F | H | H | Ph |
| 18.034 | Et | F | H | H | F |
| 18.035 | Et | F | H | H | Cl |
| 18.036 | Et | Cl | H | H | H |
| 18.037 | Et | Cl | H | H | Me |
| 18.038 | Et | Cl | H | H | Ph |
| 18.039 | Et | Cl | H | H | F |
| 18.040 | Et | Cl | H | H | Cl |
| 18.041 | H | F | F | H | H |
| 18.042 | H | F | H | F | H |

TABLE 19

Compounds according to the invention of the formula (I) in which X represents CH, A represents A17, $R^3$ and $R^4$ each represent hydrogen and $R^2$ represents chlorine:

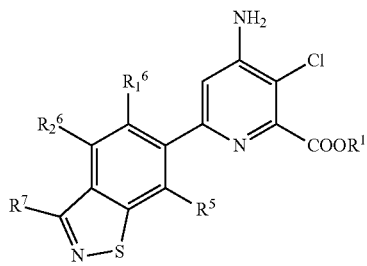

| Ex. No. | $R^1$ | $R^5$ | $R_1^6$ | $R_2^6$ | $R^7$ |
|---|---|---|---|---|---|
| 19.001 | H | H | H | H | H |
| 19.002 | H | H | H | H | Me |
| 19.003 | H | H | H | H | Ph |
| 19.004 | H | H | H | H | F |
| 19.005 | H | H | H | H | Cl |
| 19.006 | H | Cl | H | H | H |
| 19.007 | H | Cl | H | H | Me |
| 19.008 | H | Cl | H | H | Ph |
| 19.009 | H | Cl | H | H | F |
| 19.010 | H | Cl | H | H | Cl |
| 19.011 | H | F | H | H | H |
| 19.012 | H | F | H | H | Me |
| 19.013 | H | F | H | H | Ph |
| 19.014 | H | F | H | H | F |
| 19.015 | H | F | H | H | Cl |
| 19.016 | Me | H | H | H | H |
| 19.017 | Me | H | H | H | Me |
| 19.018 | Me | H | H | H | Ph |
| 19.019 | Me | H | H | H | F |
| 19.020 | Me | H | H | H | Cl |

TABLE 19-continued

Compounds according to the invention of the formula (I) in which X represents CH, A represents A17, $R^3$ and $R^4$ each represent hydrogen and $R^2$ represents chlorine:

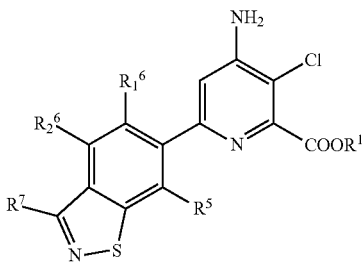

| Ex. No. | $R^1$ | $R^5$ | $R_1^6$ | $R_2^6$ | $R^7$ |
|---|---|---|---|---|---|
| 19.021 | Me | Cl | H | H | H |
| 19.022 | Me | Cl | H | H | Me |
| 19.023 | Me | Cl | H | H | Ph |
| 19.024 | Me | Cl | H | H | F |
| 19.025 | Me | Cl | H | H | Cl |
| 19.026 | Et | H | H | H | H |
| 19.027 | Et | H | H | H | Me |
| 19.028 | Et | H | H | H | Ph |
| 19.029 | Et | H | H | H | F |
| 19.030 | Et | H | H | H | Cl |
| 19.031 | Et | F | H | H | H |
| 19.032 | Et | F | H | H | Me |
| 19.033 | Et | F | H | H | Ph |
| 19.034 | Et | F | H | H | F |
| 19.035 | Et | F | H | H | Cl |
| 19.036 | Et | Cl | H | H | H |
| 19.037 | Et | Cl | H | H | Me |
| 19.038 | Et | Cl | H | H | Ph |
| 19.039 | Et | Cl | H | H | F |
| 19.040 | Et | Cl | H | H | Cl |
| 19.041 | H | F | F | H | H |
| 19.042 | H | F | H | F | H |

TABLE 20

Compounds according to the invention of the formula (I) in which X represents CH, A represents A18, $R_3$ and $R_4$ each represent hydrogen and $R^2$ represents chlorine:

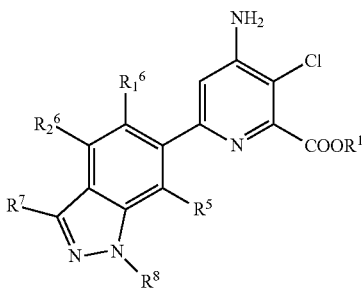

| Ex. No. | $R^1$ | $R^5$ | $R_1^6$ | $R_2^6$ | $R^7$ | $R^8$ |
|---|---|---|---|---|---|---|
| 20.001 | H | H | H | H | H | H |
| 20.002 | H | H | H | H | H | Me |
| 20.003 | H | H | H | H | H | Ph |
| 20.004 | H | H | H | H | F | Me |
| 20.005 | H | H | H | H | Cl | H |
| 20.006 | H | Cl | H | H | H | Me |
| 20.007 | H | Cl | H | H | Me | Me |
| 20.008 | H | Cl | H | H | Ph | Me |
| 20.009 | H | Cl | H | H | F | H |
| 20.010 | H | Cl | H | H | Cl | H |
| 20.011 | H | F | H | H | H | Me |
| 20.012 | H | F | H | H | Me | H |
| 20.013 | H | F | H | H | Ph | H |

TABLE 20-continued

Compounds according to the invention of the formula (I) in which X represents CH, A represents A18, $R^3$ and $R^4$ each represent hydrogen and $R^2$ represents chlorine:

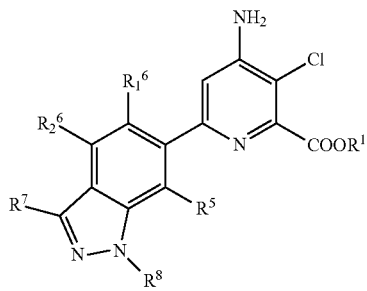

| Ex. No. | $R^1$ | $R^5$ | $R_1^6$ | $R_2^6$ | $R^7$ | $R^8$ |
|---|---|---|---|---|---|---|
| 20.014 | H | F | H | H | F | Me |
| 20.015 | H | F | H | H | Cl | Me |
| 20.016 | Me | H | H | H | H | Et |
| 20.017 | Me | H | H | H | Me | Et |
| 20.018 | Me | H | H | H | Ph | Et |
| 20.019 | Me | H | H | H | F | Et |
| 20.020 | Me | H | H | H | Cl | Et |
| 20.021 | Me | Cl | H | H | H | Me |
| 20.022 | Me | Cl | H | H | Me | H |
| 20.023 | Me | Cl | H | H | Ph | H |
| 20.024 | Me | Cl | H | H | F | H |
| 20.025 | Me | Cl | H | H | Cl | Et |
| 20.026 | Et | H | H | H | H | Me |
| 20.027 | Et | H | H | H | Me | Me |
| 20.028 | Et | H | H | H | Ph | Me |
| 20.029 | Et | H | H | H | F | H |
| 20.030 | Et | H | H | H | Cl | H |
| 20.031 | Et | F | H | H | H | Me |
| 20.032 | Et | F | H | H | Me | Me |
| 20.033 | Et | F | H | H | Ph | H |
| 20.034 | Et | F | H | H | F | Et |
| 20.035 | Et | F | H | H | Cl | Et |
| 20.036 | Et | Cl | H | H | H | H |
| 20.037 | Et | Cl | H | H | Me | H |
| 20.038 | Et | Cl | H | H | Ph | H |
| 20.039 | Et | Cl | H | H | F | Me |
| 20.040 | Et | Cl | H | H | Cl | H |
| 20.041 | H | F | F | H | H | H |
| 20.042 | H | F | H | F | H | H |

TABLE 21

Compounds according to the invention of the formula (I) in which X represents CH, A represents A19, $R^3$ and $R^4$ each represent hydrogen and $R^2$ represents chlorine:

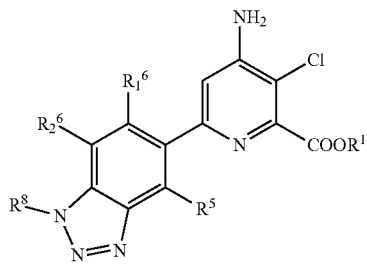

| Ex. No. | $R^1$ | $R^5$ | $R_1^6$ | $R_2^6$ | $R^8$ |
|---|---|---|---|---|---|
| 21.001 | H | H | H | H | H |
| 21.002 | H | H | H | H | Me |
| 21.003 | H | H | H | H | Et |
| 21.004 | H | F | H | H | H |
| 21.005 | H | F | H | H | Me |
| 21.006 | H | F | H | H | Et |

TABLE 21-continued

Compounds according to the invention of the formula (I) in which X represents CH, A represents A19, $R^3$ and $R^4$ each represent hydrogen and $R^2$ represents chlorine:

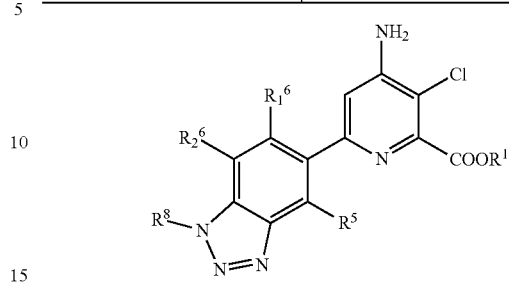

| Ex. No. | $R^1$ | $R^5$ | $R_1^6$ | $R_2^6$ | $R^8$ |
|---|---|---|---|---|---|
| 21.007 | H | Cl | H | H | H |
| 21.008 | H | Cl | H | H | Me |
| 21.009 | H | Cl | H | H | Et |
| 21.010 | Me | H | H | H | H |
| 21.011 | Me | H | H | H | Me |
| 21.012 | Me | H | H | H | Et |
| 21.013 | Me | F | H | H | H |
| 21.014 | Me | F | H | H | Me |
| 21.015 | Me | F | H | H | Et |
| 21.016 | Me | Cl | H | H | H |
| 21.017 | Me | Cl | H | H | Me |
| 21.018 | Me | Cl | H | H | Et |
| 21.019 | Et | H | H | H | H |
| 21.020 | Et | H | H | H | Me |
| 21.021 | Et | H | H | H | Et |
| 21.022 | Et | F | H | H | H |
| 21.023 | Et | F | H | H | Me |
| 21.024 | Et | F | H | H | Et |
| 21.025 | Et | Cl | H | H | H |
| 21.026 | Et | Cl | H | H | Me |
| 21.027 | Et | Cl | H | H | Et |
| 21.028 | H | F | F | H | H |
| 21.029 | H | F | H | F | H |

TABLE 22

Compounds according to the invention of the formula (I) in which X represents CH, A represents A20, $R^3$ and $R^4$ each represent hydrogen and $R^2$ represents chlorine:

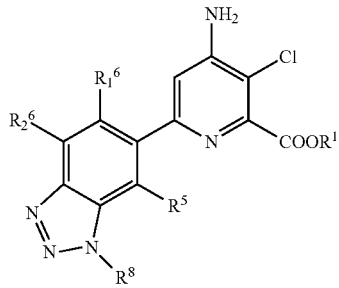

| Ex. No. | $R^1$ | $R^5$ | $R_1^6$ | $R_2^6$ | $R^8$ |
|---|---|---|---|---|---|
| 22.001 | H | H | H | H | H |
| 22.002 | H | H | H | H | Me |
| 22.003 | H | H | H | H | Et |
| 22.004 | H | F | H | H | H |
| 22.005 | H | F | H | H | Me |
| 22.006 | H | F | H | H | Et |
| 22.007 | H | Cl | H | H | H |
| 22.008 | H | Cl | H | H | Me |
| 22.009 | H | Cl | H | H | Et |
| 22.010 | Me | H | H | H | H |
| 22.011 | Me | H | H | H | Me |
| 22.012 | Me | H | H | H | Et |

TABLE 22-continued

Compounds according to the invention of the formula (I) in which X represents CH, A represents A20, $R^3$ and $R^4$ each represent hydrogen and $R^2$ represents chlorine:

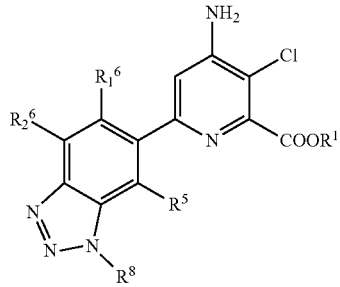

| Ex. No. | $R^1$ | $R^5$ | $R_1^6$ | $R_2^6$ | $R^8$ |
|---|---|---|---|---|---|
| 22.013 | Me | F | H | H | H |
| 22.014 | Me | F | H | H | Me |
| 22.015 | Me | F | H | H | Et |
| 22.016 | Me | Cl | H | H | H |
| 22.017 | Me | Cl | H | H | Me |
| 22.018 | Me | Cl | H | H | Et |
| 22.019 | Et | H | H | H | H |
| 22.020 | Et | H | H | H | Me |
| 22.021 | Et | H | H | H | Et |
| 22.022 | Et | F | H | H | H |
| 22.023 | Et | F | H | H | Me |
| 22.024 | Et | F | H | H | Et |
| 22.025 | Et | Cl | H | H | H |
| 22.026 | Et | Cl | H | H | Me |
| 22.027 | Et | Cl | H | H | Et |
| 22.028 | H | F | F | H | H |
| 22.029 | H | F | H | F | H |

TABLE 23

Compounds according to the invention of the formula (I) in which X represents N, A represents A1, $R^3$ and $R^4$ each represent hydrogen and $R^2$ represents chlorine:

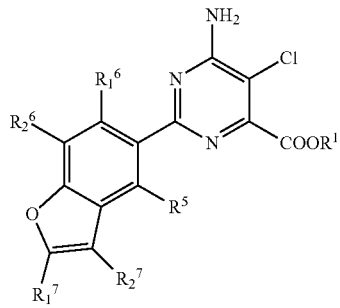

| Ex. No. | $R^1$ | $R^5$ | $R_1^6$ | $R_2^6$ | $R_1^7$ | $R_2^7$ |
|---|---|---|---|---|---|---|
| 23.001 | H | H | H | H | H | H |
| 23.002 | H | F | H | H | H | H |
| 23.003 | H | F | H | H | Cl | H |
| 23.004 | H | F | H | H | H | Cl |
| 23.005 | H | F | H | H | Cl | Cl |
| 23.006 | H | F | H | H | Ph | H |
| 23.007 | H | F | H | H | Ph | Cl |
| 23.008 | H | F | H | H | Ph | F |
| 23.009 | H | F | H | H | Me | H |
| 23.010 | H | F | H | H | Me | Cl |
| 23.011 | H | F | H | H | Me | F |
| 23.012 | Me | H | H | H | H | H |
| 23.013 | Me | F | H | H | H | H |
| 23.014 | Me | F | H | H | Cl | H |
| 23.015 | Me | F | H | H | H | Cl |
| 23.016 | Me | F | H | H | Cl | Cl |

TABLE 23-continued

Compounds according to the invention of the formula (I) in which X represents N, A represents A1, $R^3$ and $R^4$ each represent hydrogen and $R^2$ represents chlorine:

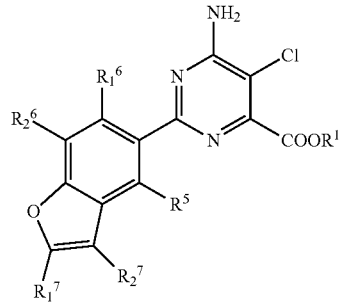

| Ex. No. | $R^1$ | $R^5$ | $R_1^6$ | $R_2^6$ | $R_1^7$ | $R_2^7$ |
|---|---|---|---|---|---|---|
| 23.017 | Me | F | H | H | H | F |
| 23.018 | Me | F | H | H | Ph | H |
| 23.019 | Me | F | H | H | Ph | Cl |
| 23.020 | Me | F | H | H | Ph | F |
| 23.021 | Me | F | H | H | Me | H |
| 23.022 | Me | F | H | H | Me | Cl |
| 23.023 | Me | F | H | H | Me | F |
| 23.024 | Et | H | H | H | H | H |
| 23.025 | Et | Cl | H | H | H | H |
| 23.026 | Et | Cl | H | H | Cl | H |
| 23.027 | Et | Cl | H | H | H | Cl |
| 23.028 | Et | Cl | H | H | Cl | Cl |
| 23.029 | Et | Cl | H | H | H | F |
| 23.030 | Et | Cl | H | H | Ph | H |
| 23.031 | Et | Cl | H | H | Ph | Cl |
| 23.032 | Et | Cl | H | H | Ph | F |
| 23.033 | Et | Cl | H | H | Me | H |
| 23.034 | Et | Cl | H | H | Me | Cl |
| 23.035 | Et | Cl | H | H | Me | F |
| 23.036 | H | F | F | H | H | H |
| 23.037 | H | F | H | F | H | H |

TABLE 24

Compounds according to the invention of the formula (I) in which X represents N, A represents A2, $R^3$ and $R^4$ each represent hydrogen and $R^2$ represents chlorine:

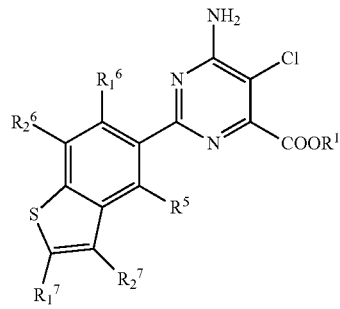

| Ex. No. | $R^1$ | $R^5$ | $R_1^6$ | $R_2^6$ | $R_1^7$ | $R_2^7$ |
|---|---|---|---|---|---|---|
| 24.001 | H | H | H | H | H | H |
| 24.002 | H | F | H | H | H | H |
| 24.003 | H | F | H | H | Cl | H |
| 24.004 | H | F | H | H | H | Cl |
| 24.005 | H | F | H | H | Cl | Cl |
| 24.006 | H | F | H | H | Ph | H |
| 24.007 | H | F | H | H | Ph | Cl |
| 24.008 | H | F | H | H | Ph | F |
| 24.009 | H | F | H | H | Me | H |
| 24.010 | H | F | H | H | Me | Cl |
| 24.011 | H | F | H | H | Me | F |

TABLE 24-continued

Compounds according to the invention of the formula (I) in which X represents N, A represents A2, $R^3$ and $R^4$ each represent hydrogen and $R^2$ represents chlorine:

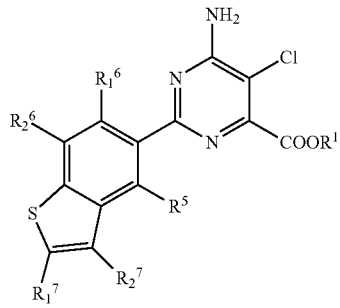

| Ex. No. | $R^1$ | $R^5$ | $R_1^6$ | $R_2^6$ | $R_1^7$ | $R_2^7$ |
|---|---|---|---|---|---|---|
| 24.012 | Me | H | H | H | H | H |
| 24.013 | Me | F | H | H | H | H |
| 24.014 | Me | F | H | H | Cl | H |
| 24.015 | Me | F | H | H | H | Cl |
| 24.016 | Me | F | H | H | Cl | Cl |
| 24.017 | Me | F | H | H | H | F |
| 24.018 | Me | F | H | H | Ph | H |
| 24.019 | Me | F | H | H | Ph | Cl |
| 24.020 | Me | F | H | H | Ph | F |
| 24.021 | Me | F | H | H | Me | H |
| 24.022 | Me | F | H | H | Me | Cl |
| 24.023 | Me | F | H | H | Me | F |
| 24.024 | Et | H | H | H | H | H |
| 24.025 | Et | Cl | H | H | H | H |
| 24.026 | Et | Cl | H | H | Cl | H |
| 24.027 | Et | Cl | H | H | H | Cl |
| 24.028 | Et | Cl | H | H | Cl | Cl |
| 24.029 | Et | Cl | H | H | H | F |
| 24.030 | Et | Cl | H | H | Ph | H |
| 24.031 | Et | Cl | H | H | Ph | Cl |
| 24.032 | Et | Cl | H | H | Ph | F |
| 24.033 | Et | Cl | H | H | Me | H |
| 24.034 | Et | Cl | H | H | Me | Cl |
| 24.035 | Et | Cl | H | H | Me | F |
| 24.036 | H | F | F | H | H | H |
| 24.037 | H | F | H | F | H | H |

TABLE 25

Compounds according to the invention of the formula (I) in which X represents N, A represents A3, $R^3$ and $R^4$ each represent hydrogen and $R^2$ represents chlorine:

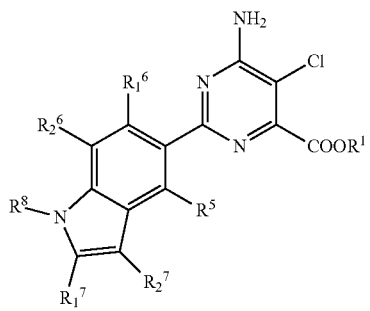

| Ex. No. | $R^1$ | $R^5$ | $R_1^6$ | $R_2^6$ | $R_1^7$ | $R_2^7$ | $R^8$ |
|---|---|---|---|---|---|---|---|
| 25.001 | H | H | H | H | H | H | H |
| 25.002 | H | F | H | H | H | H | H |
| 25.003 | H | F | H | H | Cl | H | H |
| 25.004 | H | F | H | H | H | Cl | Me |
| 25.005 | H | F | H | H | Cl | Cl | Me |
| 25.006 | H | F | H | H | Ph | H | Me |
| 25.007 | H | F | H | H | Ph | Cl | H |
| 25.008 | H | F | H | H | Ph | F | H |
| 25.009 | H | F | H | H | Me | H | H |
| 25.010 | H | F | H | H | Me | Cl | Me |
| 25.011 | H | F | H | H | Me | F | Me |
| 25.012 | Me | H | H | H | H | H | H |
| 25.013 | Me | F | H | H | H | H | H |
| 25.014 | Me | F | H | H | Cl | H | H |
| 25.015 | Me | F | H | H | H | Cl | Me |
| 25.016 | Me | F | H | H | Cl | Cl | Me |
| 25.017 | Me | F | H | H | H | F | Me |
| 25.018 | Me | F | H | H | Ph | H | H |
| 25.019 | Me | F | H | H | Ph | Cl | H |
| 25.020 | Me | F | H | H | Ph | F | H |
| 25.021 | Me | F | H | H | Me | H | H |
| 25.022 | Me | F | H | H | Me | Cl | Me |
| 25.023 | Me | F | H | H | Me | F | H |
| 25.024 | Et | H | H | H | H | H | H |
| 25.025 | Et | Cl | H | H | H | H | Me |
| 25.026 | Et | Cl | H | H | Cl | H | Me |
| 25.027 | Et | Cl | H | H | H | Cl | Me |
| 25.028 | Et | Cl | H | H | Cl | Cl | Me |
| 25.029 | Et | Cl | H | H | H | F | Me |
| 25.030 | Et | Cl | H | H | Ph | H | H |
| 25.031 | Et | Cl | H | H | Ph | Cl | H |
| 25.032 | Et | Cl | H | H | Ph | F | H |
| 25.033 | Et | Cl | H | H | Me | H | H |
| 25.034 | Et | Cl | H | H | Me | Cl | H |
| 25.035 | Et | Cl | H | H | Me | F | Me |
| 25.036 | H | F | F | H | H | H | H |
| 25.037 | H | F | H | F | H | H | H |

TABLE 25-continued

Compounds according to the invention of the formula (I) in which X represents N, A represents A3, $R^3$ and $R^4$ each represent hydrogen and $R^2$ represents chlorine:

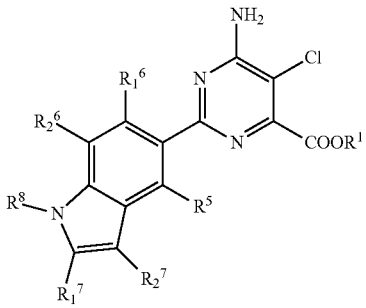

TABLE 26

Compounds according to the invention of the formula (I) in which X represents N, A represents A4, $R^3$ and $R^4$ each represent hydrogen and $R^2$ represents chlorine:

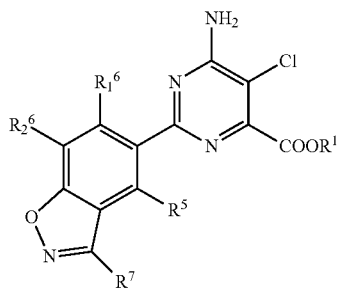

| Ex. No. | $R^1$ | $R^5$ | $R_1^6$ | $R_2^6$ | $R^7$ |
|---|---|---|---|---|---|
| 26.001 | H | H | H | H | H |
| 26.002 | H | F | H | H | H |

TABLE 26-continued

Compounds according to the invention of the formula (I) in which X represents N, A represents A4, $R^3$ and $R^4$ each represent hydrogen and $R^2$ represents chlorine:

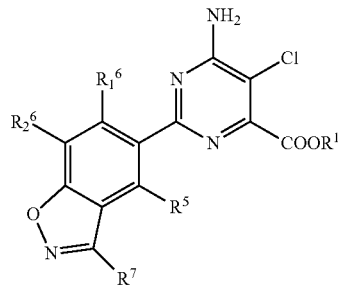

| Ex. No. | $R^1$ | $R^5$ | $R_1^6$ | $R_2^6$ | $R^7$ |
|---|---|---|---|---|---|
| 26.003 | H | F | H | H | F |
| 26.004 | H | F | H | H | Cl |
| 26.005 | H | F | H | H | Me |
| 26.006 | H | Cl | H | H | H |
| 26.007 | H | Cl | H | H | F |
| 26.008 | H | Cl | H | H | Cl |
| 26.009 | H | Cl | H | H | Me |
| 26.010 | Me | H | H | H | H |
| 26.011 | Me | F | H | H | H |
| 26.012 | Me | F | H | H | F |
| 26.013 | Me | F | H | H | Cl |
| 26.014 | Me | Cl | H | H | H |
| 26.015 | Me | Cl | H | H | F |
| 26.016 | Me | Cl | H | H | Cl |
| 26.017 | Me | Cl | H | H | Me |
| 26.018 | Et | H | H | H | H |
| 26.019 | Et | F | H | H | H |
| 26.020 | Et | Cl | H | H | H |
| 26.021 | Et | F | H | H | Me |
| 26.022 | Et | Cl | H | H | Me |
| 26.023 | H | F | F | H | H |
| 26.024 | H | F | H | F | H |

TABLE 27

Compounds according to the invention of the formula (I) in which X represents N, A represents A5, $R^3$ and $R^4$ each represent hydrogen and $R^2$ represents chlorine:

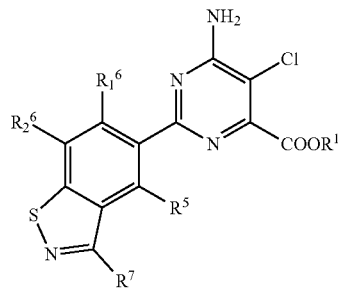

| Ex. No. | $R^1$ | $R^5$ | $R_1^6$ | $R_2^6$ | $R^7$ |
|---|---|---|---|---|---|
| 27.001 | H | H | H | H | H |
| 27.002 | H | F | H | H | H |
| 27.003 | H | F | H | H | F |
| 27.004 | H | F | H | H | Cl |
| 27.005 | H | F | H | H | F |
| 27.006 | H | Cl | H | H | H |
| 27.007 | H | Cl | H | H | F |
| 27.008 | H | Cl | H | H | Cl |
| 27.009 | H | Cl | H | H | Me |
| 27.010 | Me | H | H | H | H |
| 27.011 | Me | F | H | H | H |
| 27.012 | Me | F | H | H | Cl |

TABLE 27-continued

Compounds according to the invention of the formula (I) in which X represents N, A represents A5, $R^3$ and $R^4$ each represent hydrogen and $R^2$ represents chlorine:

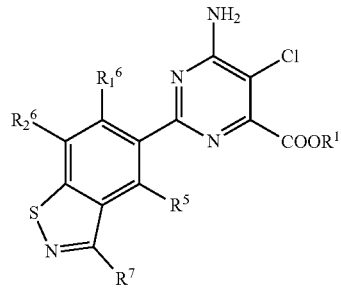

| Ex. No. | $R^1$ | $R^5$ | $R_1^6$ | $R_2^6$ | $R^7$ |
|---|---|---|---|---|---|
| 27.013 | Me | Cl | H | H | H |
| 27.014 | Me | Cl | H | H | F |
| 27.015 | Me | Cl | H | H | Cl |
| 27.016 | Me | Cl | H | H | Me |
| 27.017 | Et | H | H | H | H |
| 27.018 | Et | F | H | H | H |
| 27.019 | Et | Cl | H | H | H |
| 27.020 | Et | F | H | H | Me |
| 27.021 | Et | Cl | H | H | Me |
| 27.022 | H | F | F | H | H |
| 27.023 | H | F | H | F | H |

TABLE 28

Compounds according to the invention of the formula (I) in which X represents N, A represents A6, $R^8$, $R^3$ and $R^4$ each represent hydrogen and $R^2$ represents chlorine:

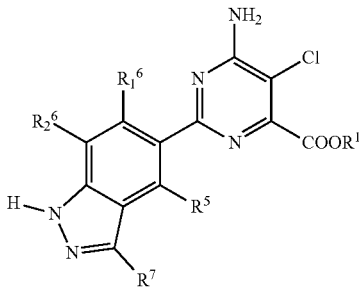

| Ex. No. | $R^1$ | $R^5$ | $R_1^6$ | $R_2^6$ | $R^7$ |
|---|---|---|---|---|---|
| 28.001 | H | H | H | H | H |
| 28.002 | H | F | H | H | H |
| 28.003 | H | F | H | H | Me |
| 28.004 | H | F | H | H | Et |
| 28.005 | H | H | H | H | Me |
| 28.006 | H | Cl | H | H | H |
| 28.007 | H | Cl | H | H | Me |
| 28.008 | H | Cl | H | H | Et |
| 28.009 | Me | H | H | H | H |
| 28.010 | Me | H | H | H | Me |
| 28.011 | Me | F | H | H | H |
| 28.012 | Me | F | H | H | Me |
| 28.013 | Me | F | H | H | Et |
| 28.014 | Me | Cl | H | H | H |
| 28.015 | Me | Cl | H | H | Me |
| 28.016 | Me | Cl | H | H | Et |
| 28.017 | Me | H | H | H | Me |
| 28.018 | Et | H | H | H | H |
| 28.019 | Et | H | H | H | Me |
| 28.020 | Et | H | H | H | Et |
| 28.021 | Et | F | H | H | H |
| 28.022 | Et | F | H | H | Me |
| 28.023 | Et | F | H | H | Et |

TABLE 28-continued

Compounds according to the invention of the formula (I) in which X represents N, A represents A6, $R^8$, $R^3$ and $R^4$ each represent hydrogen and $R^2$ represents chlorine:

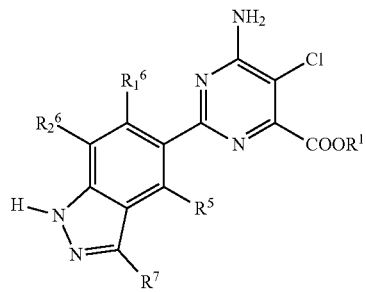

| Ex. No. | $R^1$ | $R^5$ | $R_1^6$ | $R_2^6$ | $R^7$ |
|---|---|---|---|---|---|
| 28.024 | Et | Cl | H | H | H |
| 28.025 | Et | Cl | H | H | Me |
| 28.026 | Et | Cl | H | H | Et |
| 28.027 | H | F | F | H | H |
| 28.028 | H | F | H | F | H |

TABLE 29

Compounds according to the invention of the formula (I) in which X represents N, A represents A6, $R^3$ and $R^4$ each represent hydrogen, and $R^8$ represents methyl and $R^2$ represents chlorine:

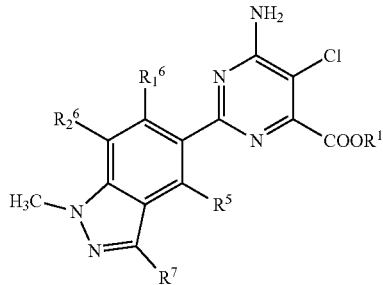

| Ex. No. | $R^1$ | $R^5$ | $R_1^6$ | $R_2^6$ | $R^7$ |
|---|---|---|---|---|---|
| 29.001 | H | H | H | H | H |
| 29.002 | H | F | H | H | H |
| 29.003 | H | F | H | H | Me |
| 29.004 | H | F | H | H | Et |
| 29.005 | H | H | H | H | Me |
| 29.006 | H | Cl | H | H | H |
| 29.007 | H | Cl | H | H | Me |
| 29.008 | H | Cl | H | H | Et |
| 29.009 | Me | H | H | H | H |
| 29.010 | Me | H | H | H | Me |
| 29.011 | Me | F | H | H | H |
| 29.012 | Me | F | H | H | Me |
| 29.013 | Me | F | H | H | Et |
| 29.014 | Me | Cl | H | H | H |
| 29.015 | Me | Cl | H | H | Me |
| 29.016 | Me | Cl | H | H | Et |
| 29.017 | Me | H | H | H | Me |
| 29.018 | Et | H | H | H | H |
| 29.019 | Et | H | H | H | Me |
| 29.020 | Et | H | H | H | Et |
| 29.021 | Et | F | H | H | H |
| 29.022 | Et | F | H | H | Me |
| 29.023 | Et | F | H | H | Et |
| 29.024 | Et | Cl | H | H | H |
| 29.025 | Et | Cl | H | H | Me |
| 29.026 | Et | Cl | H | H | Et |
| 29.027 | H | F | F | H | H |
| 29.028 | H | F | H | F | H |

TABLE 30

Compounds according to the invention of the formula (I) in which X represents N, A represents A7, $R^3$ and $R^4$ each represent hydrogen and $R^2$ represents chlorine:

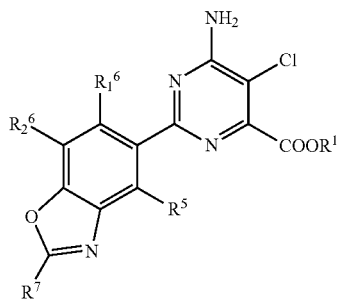

| Ex. No. | $R^1$ | $R^5$ | $R_1^6$ | $R_2^6$ | $R^7$ |
|---|---|---|---|---|---|
| 30.001 | H | H | H | H | H |
| 30.002 | H | H | H | H | Me |
| 30.003 | H | H | H | H | Ph |
| 30.004 | H | H | H | H | SMe |
| 30.005 | H | F | H | H | H |
| 30.006 | H | F | H | H | Me |
| 30.007 | H | F | H | H | Ph |
| 30.008 | H | F | H | H | SMe |
| 30.009 | H | Cl | H | H | H |
| 30.010 | H | Cl | H | H | Me |
| 30.011 | H | Cl | H | H | Ph |
| 30.012 | H | Cl | H | H | SMe |
| 30.013 | Me | H | H | H | H |
| 30.014 | Me | H | H | H | Me |
| 30.015 | Me | H | H | H | Ph |
| 30.016 | Me | H | H | H | SMe |
| 30.017 | Me | F | H | H | H |
| 30.018 | Me | F | H | H | Me |
| 30.019 | Me | F | H | H | Ph |
| 30.020 | Me | F | H | H | SMe |
| 30.021 | Me | Cl | H | H | H |
| 30.022 | Me | Cl | H | H | Me |
| 30.023 | Me | Cl | H | H | Ph |
| 30.024 | Me | Cl | H | H | SMe |
| 30.025 | Et | H | H | H | H |
| 30.026 | Et | H | H | H | Me |
| 30.027 | Et | H | H | H | Ph |
| 30.028 | Et | H | H | H | SMe |
| 30.029 | Et | F | H | H | H |
| 30.030 | Et | F | H | H | Me |
| 30.031 | Et | F | H | H | Ph |
| 30.032 | Et | F | H | H | SMe |
| 30.033 | Et | Cl | H | H | H |
| 30.034 | Et | Cl | H | H | Me |
| 30.035 | Et | Cl | H | H | Ph |
| 30.036 | Et | Cl | H | H | SMe |
| 30.037 | H | F | F | H | H |
| 30.038 | H | F | H | F | H |

TABLE 31

Compounds according to the invention of the formula (I) in which X represents N, A represents A8, $R^3$ and $R^4$ each represent hydrogen and $R^2$ represents chlorine:

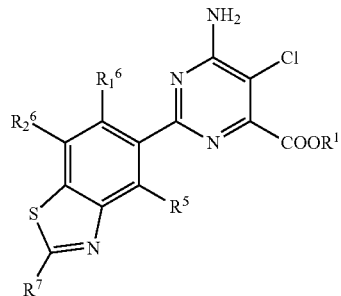

| Ex. No. | $R^1$ | $R^5$ | $R_1^6$ | $R_2^6$ | $R^7$ |
|---|---|---|---|---|---|
| 31.001 | H | H | H | H | H |
| 31.002 | H | H | H | H | Me |
| 31.003 | H | H | H | H | Ph |
| 31.004 | H | H | H | H | SMe |
| 31.005 | H | F | H | H | H |
| 31.006 | H | F | H | H | Me |
| 31.007 | H | F | H | H | Ph |
| 31.008 | H | F | H | H | SMe |
| 31.009 | H | Cl | H | H | H |
| 31.010 | H | Cl | H | H | Me |
| 31.011 | H | Cl | H | H | Ph |
| 31.012 | H | Cl | H | H | SMe |
| 31.013 | Me | H | H | H | H |
| 31.014 | Me | H | H | H | Me |
| 31.015 | Me | H | H | H | Ph |
| 31.016 | Me | H | H | H | SMe |
| 31.017 | Me | F | H | H | H |
| 31.018 | Me | F | H | H | Me |
| 31.019 | Me | F | H | H | Ph |
| 31.020 | Me | F | H | H | SMe |
| 31.021 | Me | Cl | H | H | H |
| 31.022 | Et | H | H | H | H |
| 31.023 | Et | H | H | H | Me |
| 31.024 | Et | H | H | H | Ph |
| 31.025 | Et | H | H | H | SMe |
| 31.026 | Et | F | H | H | H |
| 31.027 | Et | F | H | H | Me |
| 31.028 | Et | F | H | H | Ph |
| 31.029 | Et | F | H | H | SMe |
| 31.030 | Et | Cl | H | H | H |
| 31.031 | Et | Cl | H | H | Me |
| 31.032 | Et | Cl | H | H | Ph |
| 31.033 | Et | Cl | H | H | SMe |
| 31.034 | H | F | F | H | H |
| 31.035 | H | F | H | F | H |

TABLE 32

Compounds according to the invention of the formula (I) in which X represents N, A represents A9, $R^3$ and $R^4$ each represent hydrogen and $R^2$ represents chlorine:

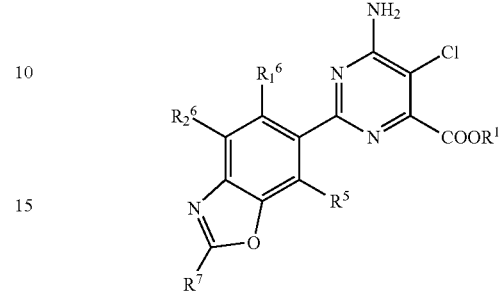

| Ex. No. | $R^1$ | $R^5$ | $R_1^6$ | $R_2^6$ | $R^7$ |
|---|---|---|---|---|---|
| 32.001 | H | H | H | H | H |
| 32.002 | H | H | H | H | Me |
| 32.003 | H | H | H | H | Ph |
| 32.004 | H | H | H | H | SMe |
| 32.005 | H | F | H | H | H |
| 32.006 | H | F | H | H | Me |
| 32.007 | H | F | H | H | Ph |
| 32.008 | H | F | H | H | SMe |
| 32.009 | H | Cl | H | H | H |
| 32.010 | H | Cl | H | H | Me |
| 32.011 | H | Cl | H | H | Ph |
| 32.012 | H | Cl | H | H | SMe |
| 32.013 | Me | H | H | H | H |
| 32.014 | Me | H | H | H | Me |
| 32.015 | Me | H | H | H | Ph |
| 32.016 | Me | H | H | H | SMe |
| 32.017 | Me | F | H | H | H |
| 32.018 | Me | F | H | H | Me |
| 32.019 | Me | F | H | H | Ph |
| 32.020 | Me | F | H | H | SMe |
| 32.021 | Me | Cl | H | H | H |
| 32.022 | Me | Cl | H | H | Me |
| 32.023 | Me | Cl | H | H | Ph |
| 32.024 | Me | Cl | H | H | SMe |
| 32.025 | Et | H | H | H | H |
| 32.026 | Et | H | H | H | Me |
| 32.027 | Et | H | H | H | Ph |
| 32.028 | Et | H | H | H | SMe |
| 32.029 | Et | F | H | H | H |
| 32.030 | Et | F | H | H | Me |
| 32.031 | Et | F | H | H | Ph |
| 32.032 | Et | F | H | H | SMe |
| 32.033 | Et | Cl | H | H | H |
| 32.034 | Et | Cl | H | H | Me |
| 32.035 | Et | Cl | H | H | Ph |
| 32.036 | Et | Cl | H | H | SMe |
| 32.037 | H | F | F | H | H |
| 32.038 | H | F | H | F | H |

TABLE 33

Compounds according to the invention of the formula (I) in which X represents N, A represents A10, $R^3$ and $R^4$ each represent hydrogen and $R^2$ represents chlorine:

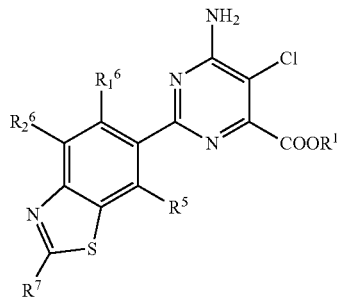

| Ex. No. | $R^1$ | $R^5$ | $R_1^6$ | $R_2^6$ | $R^7$ |
|---|---|---|---|---|---|
| 33.001 | H | H | H | H | H |
| 33.002 | H | H | H | H | Me |
| 33.003 | H | H | H | H | Ph |
| 33.004 | H | H | H | H | SMe |
| 33.005 | H | F | H | H | H |
| 33.006 | H | F | H | H | Me |
| 33.007 | H | F | H | H | Ph |
| 33.008 | H | F | H | H | SMe |
| 33.009 | H | Cl | H | H | H |
| 33.010 | H | Cl | H | H | Me |
| 33.011 | H | Cl | H | H | Ph |
| 33.012 | H | Cl | H | H | SMe |
| 33.013 | Me | H | H | H | H |
| 33.014 | Me | H | H | H | Me |
| 33.015 | Me | H | H | H | Ph |
| 33.016 | Me | H | H | H | SMe |
| 33.017 | Me | F | H | H | H |
| 33.018 | Me | F | H | H | Me |
| 33.019 | Me | F | H | H | Ph |
| 33.020 | Me | F | H | H | SMe |
| 33.021 | Me | Cl | H | H | H |
| 33.022 | Et | H | H | H | H |
| 33.023 | Et | H | H | H | Me |
| 33.024 | Et | H | H | H | Ph |
| 33.025 | Et | H | H | H | SMe |
| 33.026 | Et | F | H | H | H |
| 33.027 | Et | F | H | H | Me |
| 33.028 | Et | F | H | H | Ph |
| 33.029 | Et | F | H | H | SMe |
| 33.030 | Et | Cl | H | H | H |
| 33.031 | Et | Cl | H | H | Me |
| 33.032 | Et | Cl | H | H | Ph |
| 33.033 | Et | Cl | H | H | SMe |
| 33.034 | H | F | F | H | H |
| 33.035 | H | F | H | F | H |

TABLE 34

Compounds according to the invention of the formula (I) in which X represents N, A represents A11, $R^3$ and $R^4$ each represent hydrogen and $R^2$ represents chlorine:

| Ex. No. | $R^1$ | $R^5$ | $R_1^6$ | $R_2^6$ | $R^7$ | $R^8$ |
|---|---|---|---|---|---|---|
| 34.001 | H | H | H | H | H | H |
| 34.002 | H | F | H | H | H | H |
| 34.003 | H | F | H | H | H | Me |
| 34.004 | H | F | H | H | Me | H |
| 34.005 | H | F | H | H | Me | Me |
| 34.006 | H | Cl | H | H | H | H |
| 34.007 | H | Cl | H | H | H | Me |
| 34.008 | H | Cl | H | H | Me | H |
| 34.009 | H | Cl | H | H | Me | Me |
| 34.010 | H | H | H | H | Ph | H |
| 34.011 | H | H | H | H | Ph | Me |
| 34.012 | H | F | H | H | Ph | H |
| 34.013 | H | F | H | H | Ph | Me |
| 34.014 | H | Cl | H | H | Ph | H |
| 34.015 | H | Cl | H | H | Ph | Me |
| 34.016 | H | H | H | H | Me | H |
| 34.017 | H | H | H | H | H | Me |
| 34.018 | H | H | H | H | Me | Me |
| 34.019 | Me | H | H | H | H | H |
| 34.020 | Me | F | H | H | H | H |
| 34.021 | Me | F | H | H | H | Me |
| 34.022 | Me | F | H | H | Me | H |
| 34.023 | Me | F | H | H | Me | Me |
| 34.024 | Me | Cl | H | H | H | H |
| 34.025 | Me | Cl | H | H | H | Me |
| 34.026 | Me | Cl | H | H | Me | H |
| 34.027 | Me | Cl | H | H | Me | Me |
| 34.028 | Me | H | H | H | Ph | H |
| 34.029 | Me | H | H | H | Ph | Me |
| 34.030 | Me | F | H | H | Ph | H |
| 34.031 | Me | F | H | H | Ph | Me |
| 34.032 | Me | Cl | H | H | Ph | H |
| 34.033 | Me | Cl | H | H | Ph | Me |
| 34.034 | Me | H | H | H | Me | H |
| 34.035 | Me | H | H | H | H | Me |
| 34.036 | Me | H | H | H | Me | Me |
| 34.037 | Et | H | H | H | H | H |
| 34.038 | Et | F | H | H | H | H |
| 34.039 | Et | F | H | H | H | Me |
| 34.040 | Et | F | H | H | Me | H |
| 34.041 | Et | F | H | H | Me | Me |
| 34.042 | Et | Cl | H | H | H | H |
| 34.043 | Et | Cl | H | H | H | Me |
| 34.044 | Et | Cl | H | H | Me | H |
| 34.045 | Et | H | H | H | Ph | H |
| 34.046 | Et | H | H | H | Ph | Me |
| 34.047 | Et | F | H | H | Ph | H |
| 34.048 | Et | F | H | H | Ph | Me |
| 34.049 | Et | Cl | H | H | Ph | H |
| 34.050 | Et | Cl | H | H | Me | Me |
| 34.051 | Et | H | H | H | Me | H |
| 34.052 | Et | H | H | H | H | Me |
| 34.053 | Et | H | H | H | Me | Me |
| 34.054 | H | F | F | H | H | H |
| 34.055 | H | F | H | F | H | H |

TABLE 35

Compounds according to the invention of the formula (I) in which X represents N, A represents A12, $R^3$ and $R^4$ each represent hydrogen and $R^2$ represents chlorine:

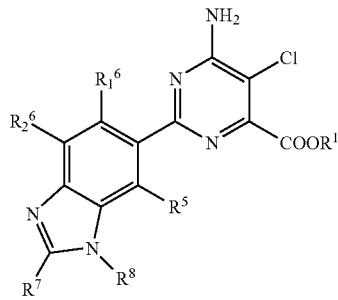

| Ex. No. | $R^1$ | $R^5$ | $R_1^6$ | $R_2^6$ | $R^7$ | $R^8$ |
|---|---|---|---|---|---|---|
| 35.001 | H | H | H | H | H | Me |
| 35.002 | H | F | H | H | H | Me |
| 35.003 | H | F | H | H | Me | Me |
| 35.004 | H | Cl | H | H | H | Me |
| 35.005 | H | Cl | H | H | Me | Me |
| 35.006 | H | H | H | H | Ph | Me |
| 35.007 | H | F | H | H | Ph | Me |
| 35.008 | H | Cl | H | H | Ph | Me |
| 35.009 | H | H | H | H | H | Me |
| 35.010 | Me | H | H | H | H | Me |
| 35.011 | Me | F | H | H | H | Me |
| 35.012 | Me | H | H | H | Me | Me |
| 35.013 | Me | F | H | H | Me | Me |
| 35.014 | Me | Cl | H | H | H | Me |
| 35.015 | Me | Cl | H | H | Me | Me |
| 35.016 | Me | H | H | H | Ph | Me |
| 35.017 | Me | F | H | H | Ph | Me |
| 35.018 | Me | Cl | H | H | Ph | Me |
| 35.019 | Et | F | H | H | H | Me |
| 35.020 | Et | F | H | H | Me | Me |
| 35.021 | Et | Cl | H | H | H | Me |
| 35.022 | Et | H | H | H | Ph | Me |
| 35.023 | Et | F | H | H | Ph | Me |
| 35.024 | Et | Cl | H | H | Ph | Me |
| 35.025 | Et | H | H | H | H | Me |
| 35.026 | Et | H | H | H | Me | Me |
| 35.027 | Et | Cl | H | H | Me | Me |
| 35.028 | H | F | F | H | H | H |
| 35.029 | H | F | H | F | H | H |

TABLE 36

Compounds according to the invention of the formula (I) in which X represents N, A represents A13, $R^3$ and $R^4$ each represent hydrogen and $R^2$ represents chlorine:

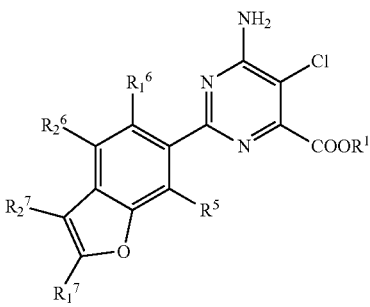

| Ex. No. | $R^1$ | $R^5$ | $R_1^6$ | $R_2^6$ | $R_1^7$ | $R_2^7$ |
|---|---|---|---|---|---|---|
| 36.001 | H | H | H | H | H | H |
| 36.002 | H | H | H | H | H | Cl |
| 36.003 | H | H | H | H | H | F |
| 36.004 | H | H | H | H | H | Me |
| 36.005 | H | H | H | H | F | H |
| 36.006 | H | H | H | H | F | Cl |
| 36.007 | H | H | H | H | F | F |
| 36.008 | H | H | H | H | F | Me |
| 36.009 | H | H | H | H | Cl | H |
| 36.010 | H | H | H | H | Cl | F |
| 36.011 | H | H | H | H | Cl | Cl |
| 36.012 | H | H | H | H | Cl | Me |
| 36.013 | H | H | H | H | Me | H |
| 36.014 | H | H | H | H | Me | Cl |
| 36.015 | H | H | H | H | Me | F |
| 36.016 | H | H | H | H | Me | Me |
| 36.017 | H | H | H | H | Ph | H |
| 36.018 | H | H | H | H | Ph | Cl |
| 36.019 | H | H | H | H | Ph | F |
| 36.020 | H | H | H | H | Ph | Me |
| 36.021 | H | F | H | H | H | H |
| 36.022 | H | F | H | H | H | Cl |
| 36.023 | H | F | H | H | H | F |
| 36.024 | H | F | H | H | H | Me |
| 36.025 | H | F | H | H | F | H |
| 36.026 | H | F | H | H | F | Cl |
| 36.027 | H | F | H | H | F | F |
| 36.028 | H | F | H | H | F | Me |
| 36.029 | H | F | H | H | Cl | H |
| 36.030 | H | F | H | H | Cl | F |
| 36.031 | H | F | H | H | Cl | Cl |
| 36.032 | H | F | H | H | Cl | Me |
| 36.033 | H | F | H | H | Me | H |
| 36.034 | H | F | H | H | Me | Cl |
| 36.035 | H | F | H | H | Me | F |
| 36.036 | H | F | H | H | Me | Me |
| 36.037 | H | F | H | H | Ph | H |
| 36.038 | H | F | H | H | Ph | Cl |
| 36.039 | H | F | H | H | Ph | F |
| 36.040 | H | F | H | H | Ph | Me |
| 36.041 | H | Cl | H | H | H | H |
| 36.042 | H | Cl | H | H | H | Cl |
| 36.043 | H | Cl | H | H | H | F |
| 36.044 | H | Cl | H | H | H | Me |
| 36.045 | H | Cl | H | H | F | H |
| 36.046 | H | Cl | H | H | F | Cl |
| 36.047 | H | Cl | H | H | F | F |
| 36.048 | H | Cl | H | H | F | Me |
| 36.049 | H | Cl | H | H | Cl | H |
| 36.050 | H | Cl | H | H | Cl | F |
| 36.051 | H | Cl | H | H | Cl | Cl |
| 36.052 | H | Cl | H | H | Cl | Me |
| 36.053 | H | Cl | H | H | Me | H |
| 36.054 | H | Cl | H | H | Me | Cl |
| 36.055 | H | Cl | H | H | Me | F |
| 36.056 | H | Cl | H | H | Me | Me |
| 36.057 | H | Cl | H | H | Ph | H |
| 36.058 | H | Cl | H | H | Ph | Cl |
| 36.059 | H | Cl | H | H | Ph | F |
| 36.060 | H | Cl | H | H | Ph | Me |
| 36.061 | Me | H | H | H | H | H |
| 36.062 | Me | H | H | H | H | Cl |
| 36.063 | Me | H | H | H | H | F |

TABLE 36-continued

Compounds according to the invention of the formula (I) in which X represents N, A represents A13, $R^3$ and $R^4$ each represent hydrogen and $R^2$ represents chlorine:

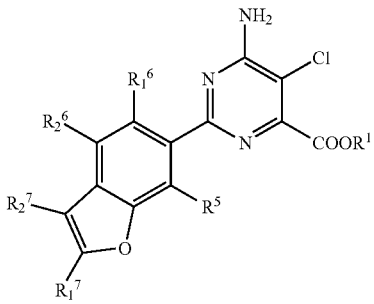
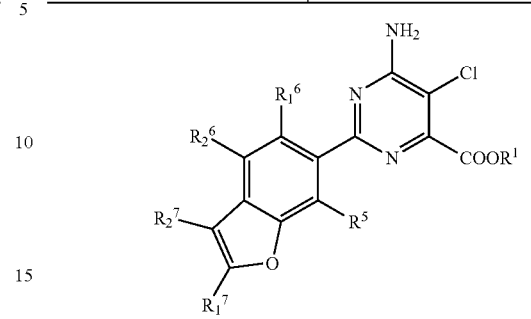

| Ex. No. | $R^1$ | $R^5$ | $R_1^6$ | $R_2^6$ | $R_1^7$ | $R_2^7$ |
|---|---|---|---|---|---|---|
| 36.064 | Me | H | H | H | H | Me |
| 36.065 | Me | H | H | H | F | H |
| 36.066 | Me | H | H | H | F | Cl |
| 36.067 | Me | H | H | H | F | F |
| 36.068 | Me | H | H | H | F | Me |
| 36.069 | Me | H | H | H | Cl | H |
| 36.070 | Me | H | H | H | Cl | F |
| 36.071 | Me | H | H | H | Cl | Cl |
| 36.072 | Me | H | H | H | Cl | Me |
| 36.073 | Me | H | H | H | Me | H |
| 36.074 | Me | H | H | H | Me | Cl |
| 36.075 | Me | H | H | H | Me | F |
| 36.076 | Me | H | H | H | Me | Me |
| 36.077 | Me | H | H | H | Ph | H |
| 36.078 | Me | H | H | H | Ph | Cl |
| 36.079 | Me | H | H | H | Ph | F |
| 36.080 | Me | H | H | H | Ph | Me |
| 36.081 | Me | F | H | H | H | H |
| 36.082 | Me | F | H | H | H | Cl |
| 36.083 | Me | F | H | H | H | F |
| 36.084 | Me | F | H | H | H | Me |
| 36.085 | Me | F | H | H | F | H |
| 36.086 | Me | F | H | H | F | Cl |
| 36.087 | Me | F | H | H | F | F |
| 36.088 | Me | F | H | H | F | Me |
| 36.089 | Me | F | H | H | Cl | H |
| 36.090 | Me | F | H | H | Cl | F |
| 36.091 | Me | F | H | H | Cl | Cl |
| 36.092 | Me | F | H | H | Cl | Me |
| 36.093 | Me | F | H | H | Me | H |
| 36.094 | Me | F | H | H | Me | Cl |
| 36.095 | Me | F | H | H | Me | F |
| 36.096 | Me | F | H | H | Me | Me |
| 36.097 | Me | F | H | H | Ph | H |
| 36.098 | Me | F | H | H | Ph | Cl |
| 36.099 | Me | F | H | H | Ph | F |
| 36.100 | Me | F | H | H | Ph | Me |
| 36.101 | Me | Cl | H | H | H | H |
| 36.102 | Me | Cl | H | H | H | Cl |
| 36.103 | Me | Cl | H | H | H | F |
| 36.104 | Me | Cl | H | H | H | Me |
| 36.105 | Me | Cl | H | H | F | H |
| 36.106 | Me | Cl | H | H | F | Cl |
| 36.107 | Me | Cl | H | H | F | F |
| 36.108 | Me | Cl | H | H | F | Me |
| 36.109 | Me | Cl | H | H | Cl | H |
| 36.110 | Me | Cl | H | H | Cl | F |
| 36.111 | Me | Cl | H | H | Cl | Cl |
| 36.112 | Me | Cl | H | H | Cl | Me |
| 36.113 | Me | Cl | H | H | Me | H |
| 36.114 | Me | Cl | H | H | Me | Cl |
| 36.115 | Me | Cl | H | H | Me | F |
| 36.116 | Me | Cl | H | H | Me | Me |
| 36.117 | Me | Cl | H | H | Ph | H |
| 36.118 | Me | Cl | H | H | Ph | Cl |
| 36.119 | Me | Cl | H | H | Ph | F |
| 36.120 | Me | Cl | H | H | Ph | Me |
| 36.121 | Et | H | H | H | H | H |
| 36.122 | Et | H | H | H | H | Cl |
| 36.123 | Et | H | H | H | H | F |
| 36.124 | Et | H | H | H | H | Me |
| 36.125 | Et | H | H | H | F | H |
| 36.126 | Et | H | H | H | F | Cl |
| 36.127 | Et | H | H | H | F | F |
| 36.128 | Et | H | H | H | F | Me |
| 36.129 | Et | H | H | H | Cl | H |
| 36.130 | Et | H | H | H | Cl | F |
| 36.131 | Et | H | H | H | Cl | Cl |
| 36.132 | Et | H | H | H | Cl | Me |
| 36.133 | Et | H | H | H | Me | H |
| 36.134 | Et | H | H | H | Me | Cl |
| 36.135 | Et | H | H | H | Me | F |
| 36.136 | Et | H | H | H | Me | Me |
| 36.137 | Et | H | H | H | Ph | H |
| 36.138 | Et | H | H | H | Ph | Cl |
| 36.139 | Et | H | H | H | Ph | F |
| 36.140 | Et | H | H | H | Ph | Me |
| 36.141 | Et | F | H | H | H | H |
| 36.142 | Et | F | H | H | H | Cl |
| 36.143 | Et | F | H | H | H | F |
| 36.144 | Et | F | H | H | H | Me |
| 36.145 | Et | F | H | H | F | H |
| 36.146 | Et | F | H | H | F | Cl |
| 36.147 | Et | F | H | H | F | F |
| 36.148 | Et | F | H | H | F | Me |
| 36.149 | Et | F | H | H | Cl | H |
| 36.150 | Et | F | H | H | Cl | F |
| 36.151 | Et | F | H | H | Cl | Cl |
| 36.152 | Et | F | H | H | Cl | Me |
| 36.153 | Et | F | H | H | Me | H |
| 36.154 | Et | F | H | H | Me | Cl |
| 36.155 | Et | F | H | H | Me | F |
| 36.156 | Et | F | H | H | Me | Me |
| 36.157 | Et | F | H | H | Ph | H |
| 36.158 | Et | F | H | H | Ph | Cl |
| 36.159 | Et | F | H | H | Ph | F |
| 36.160 | Et | F | H | H | Ph | Me |
| 36.161 | Et | Cl | H | H | H | H |
| 36.162 | Et | Cl | H | H | H | Cl |
| 36.163 | Et | Cl | H | H | H | F |
| 36.164 | Et | Cl | H | H | H | Me |
| 36.165 | Et | Cl | H | H | F | H |
| 36.166 | Et | Cl | H | H | F | Cl |
| 36.167 | Et | Cl | H | H | F | F |
| 36.168 | Et | Cl | H | H | F | Me |
| 36.169 | Et | Cl | H | H | Cl | H |
| 36.170 | Et | Cl | H | H | Cl | F |
| 36.171 | Et | Cl | H | H | Cl | Cl |
| 36.172 | Et | Cl | H | H | Cl | Me |
| 36.173 | Et | Cl | H | H | Me | H |
| 36.174 | Et | Cl | H | H | Me | Cl |
| 36.175 | Et | Cl | H | H | Me | F |
| 36.176 | Et | Cl | H | H | Me | Me |
| 36.177 | Et | Cl | H | H | Ph | H |
| 36.178 | Et | Cl | H | H | Ph | Cl |
| 36.179 | Et | Cl | H | H | Ph | F |
| 36.180 | Et | Cl | H | H | Ph | Me |
| 36.181 | H | F | F | H | H | H |

TABLE 36-continued

Compounds according to the invention of the formula (I) in which X represents N, A represents A13, $R^3$ and $R^4$ each represent hydrogen and $R^2$ represents chlorine:

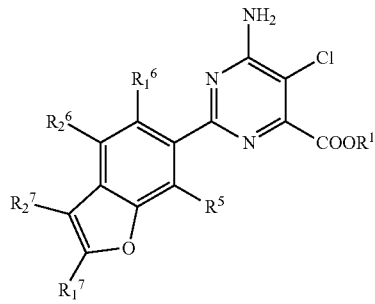

| Ex. No. | $R^1$ | $R^5$ | $R_1^6$ | $R_2^6$ | $R_1^7$ | $R_2^7$ |
|---|---|---|---|---|---|---|
| 36.182 | H | F | H | F | H | H |

TABLE 37

Compounds according to the invention of the formula (I) in which X represents N, A represents A14, $R^3$ and $R^4$ each represent hydrogen and $R^2$ represents chlorine:

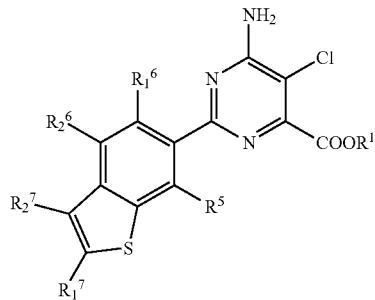

| Ex. No. | $R^1$ | $R^5$ | $R_1^6$ | $R_2^6$ | $R_1^7$ | $R_2^7$ |
|---|---|---|---|---|---|---|
| 37.001 | H | H | H | H | H | H |
| 37.002 | H | H | H | H | H | Cl |
| 37.003 | H | H | H | H | H | F |
| 37.004 | H | H | H | H | H | Me |
| 37.005 | H | H | H | H | F | H |
| 37.006 | H | H | H | H | F | Cl |
| 37.007 | H | H | H | H | F | F |
| 37.008 | H | H | H | H | F | Me |
| 37.009 | H | H | H | H | Cl | H |
| 37.010 | H | H | H | H | Cl | F |
| 37.011 | H | H | H | H | Cl | Cl |
| 37.012 | H | H | H | H | Cl | Me |
| 37.013 | H | H | H | H | Me | H |
| 37.014 | H | H | H | H | Me | Cl |
| 37.015 | H | H | H | H | Me | F |
| 37.016 | H | H | H | H | Me | Me |
| 37.017 | H | H | H | H | Ph | H |
| 37.018 | H | H | H | H | Ph | Cl |
| 37.019 | H | H | H | H | Ph | F |
| 37.020 | H | H | H | H | Ph | Me |
| 37.021 | H | F | H | H | H | H |
| 37.022 | H | F | H | H | H | Cl |
| 37.023 | H | F | H | H | H | F |
| 37.024 | H | F | H | H | H | Me |
| 37.025 | H | F | H | H | F | H |
| 37.026 | H | F | H | H | F | Cl |
| 37.027 | H | F | H | H | F | F |
| 37.028 | H | F | H | H | F | Me |
| 37.029 | H | F | H | H | Cl | H |
| 37.030 | H | F | H | H | Cl | F |
| 37.031 | H | F | H | H | Cl | Cl |

TABLE 37-continued

Compounds according to the invention of the formula (I) in which X represents N, A represents A14, $R^3$ and $R^4$ each represent hydrogen and $R^2$ represents chlorine:

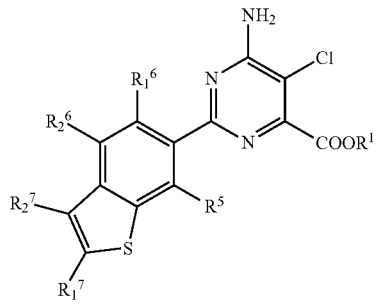

| Ex. No. | $R^1$ | $R^5$ | $R_1^6$ | $R_2^6$ | $R_1^7$ | $R_2^7$ |
|---|---|---|---|---|---|---|
| 37.032 | H | F | H | H | Cl | Me |
| 37.033 | H | F | H | H | Me | H |
| 37.034 | H | F | H | H | Me | Cl |
| 37.035 | H | F | H | H | Me | F |
| 37.036 | H | F | H | H | Me | Me |
| 37.037 | H | F | H | H | Ph | H |
| 37.038 | H | F | H | H | Ph | Cl |
| 37.039 | H | F | H | H | Ph | F |
| 37.040 | H | F | H | H | Ph | Me |
| 37.041 | H | Cl | H | H | H | H |
| 37.042 | H | Cl | H | H | H | Cl |
| 37.043 | H | Cl | H | H | H | F |
| 37.044 | H | Cl | H | H | H | Me |
| 37.045 | H | Cl | H | H | F | H |
| 37.046 | H | Cl | H | H | F | Cl |
| 37.047 | H | Cl | H | H | F | F |
| 37.048 | H | Cl | H | H | F | Me |
| 37.049 | H | Cl | H | H | Cl | H |
| 37.050 | H | Cl | H | H | Cl | F |
| 37.051 | H | Cl | H | H | Cl | Cl |
| 37.052 | H | Cl | H | H | Cl | Me |
| 37.053 | H | Cl | H | H | Me | H |
| 37.054 | H | Cl | H | H | Me | Cl |
| 37.055 | H | Cl | H | H | Me | F |
| 37.056 | H | Cl | H | H | Me | Me |
| 37.057 | H | Cl | H | H | Ph | H |
| 37.058 | H | Cl | H | H | Ph | Cl |
| 37.059 | H | Cl | H | H | Ph | F |
| 37.060 | H | Cl | H | H | Ph | Me |
| 37.061 | Me | H | H | H | H | H |
| 37.062 | Me | H | H | H | H | Cl |
| 37.063 | Me | H | H | H | H | F |
| 37.064 | Me | H | H | H | H | Me |
| 37.065 | Me | H | H | H | F | H |
| 37.066 | Me | H | H | H | F | Cl |
| 37.067 | Me | H | H | H | F | F |
| 37.068 | Me | H | H | H | F | Me |
| 37.069 | Me | H | H | H | Cl | H |
| 37.070 | Me | H | H | H | Cl | F |
| 37.071 | Me | H | H | H | Cl | Cl |
| 37.072 | Me | H | H | H | Cl | Me |
| 37.073 | Me | H | H | H | Me | H |
| 37.074 | Me | H | H | H | Me | Cl |
| 37.075 | Me | H | H | H | Me | F |
| 37.076 | Me | H | H | H | Me | Me |
| 37.077 | Me | H | H | H | Ph | H |
| 37.078 | Me | H | H | H | Ph | Cl |
| 37.079 | Me | H | H | H | Ph | F |
| 37.080 | Me | H | H | H | Ph | Me |
| 37.081 | Me | F | H | H | H | H |
| 37.082 | Me | F | H | H | H | Cl |
| 37.083 | Me | F | H | H | H | F |
| 37.084 | Me | F | H | H | H | Me |
| 37.085 | Me | F | H | H | F | H |
| 37.086 | Me | F | H | H | F | Cl |
| 37.087 | Me | F | H | H | F | F |
| 37.088 | Me | F | H | H | F | Me |
| 37.089 | Me | F | H | H | Cl | H |
| 37.090 | Me | F | H | H | Cl | F |

TABLE 37-continued

Compounds according to the invention of the formula (I) in which X represents N, A represents A14, $R^3$ and $R^4$ each represent hydrogen and $R^2$ represents chlorine:

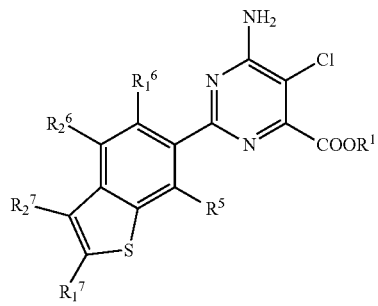

| Ex. No. | $R^1$ | $R^5$ | $R_1^6$ | $R_2^6$ | $R_1^7$ | $R_2^7$ |
|---|---|---|---|---|---|---|
| 37.091 | Me | F | H | H | Cl | Cl |
| 37.092 | Me | F | H | H | Cl | Me |
| 37.093 | Me | F | H | H | Me | H |
| 37.094 | Me | F | H | H | Me | Cl |
| 37.095 | Me | F | H | H | Me | F |
| 37.096 | Me | F | H | H | Me | Me |
| 37.097 | Me | F | H | H | Ph | H |
| 37.098 | Me | F | H | H | Ph | Cl |
| 37.099 | Me | F | H | H | Ph | F |
| 37.100 | Me | F | H | H | Ph | Me |
| 37.101 | Me | Cl | H | H | H | H |
| 37.102 | Me | Cl | H | H | H | Cl |
| 37.103 | Me | Cl | H | H | H | F |
| 37.104 | Me | Cl | H | H | H | Me |
| 37.105 | Me | Cl | H | H | F | H |
| 37.106 | Me | Cl | H | H | F | Cl |
| 37.107 | Me | Cl | H | H | F | F |
| 37.108 | Me | Cl | H | H | F | Me |
| 37.109 | Me | Cl | H | H | Cl | H |
| 37.110 | Me | Cl | H | H | Cl | F |
| 37.111 | Me | Cl | H | H | Cl | Cl |
| 37.112 | Me | Cl | H | H | Cl | Me |
| 37.113 | Me | Cl | H | H | Me | H |
| 37.114 | Me | Cl | H | H | Me | Cl |
| 37.115 | Me | Cl | H | H | Me | F |
| 37.116 | Me | Cl | H | H | Me | Me |
| 37.117 | Me | Cl | H | H | Ph | H |
| 37.118 | Me | Cl | H | H | Ph | Cl |
| 37.119 | Me | Cl | H | H | Ph | F |
| 37.120 | Me | Cl | H | H | Ph | Me |
| 37.121 | Et | H | H | H | H | H |
| 37.122 | Et | H | H | H | H | Cl |
| 37.123 | Et | H | H | H | H | F |
| 37.124 | Et | H | H | H | H | Me |
| 37.125 | Et | H | H | H | F | H |
| 37.126 | Et | H | H | H | F | Cl |
| 37.127 | Et | H | H | H | F | F |
| 37.128 | Et | H | H | H | F | Me |
| 37.129 | Et | H | H | H | Cl | H |
| 37.130 | Et | H | H | H | Cl | F |
| 37.131 | Et | H | H | H | Cl | Cl |
| 37.132 | Et | H | H | H | Cl | Me |
| 37.133 | Et | H | H | H | Me | H |
| 37.134 | Et | H | H | H | Me | Cl |
| 37.135 | Et | H | H | H | Me | F |
| 37.136 | Et | H | H | H | Me | Me |
| 37.137 | Et | H | H | H | Ph | H |
| 37.138 | Et | H | H | H | Ph | Cl |
| 37.139 | Et | H | H | H | Ph | F |
| 37.140 | Et | H | H | H | Ph | Me |
| 37.141 | Et | F | H | H | H | H |
| 37.142 | Et | F | H | H | H | Cl |
| 37.143 | Et | F | H | H | H | F |
| 37.144 | Et | F | H | H | H | Me |
| 37.145 | Et | F | H | H | F | H |

TABLE 37-continued

Compounds according to the invention of the formula (I) in which X represents N, A represents A14, $R^3$ and $R^4$ each represent hydrogen and $R^2$ represents chlorine:

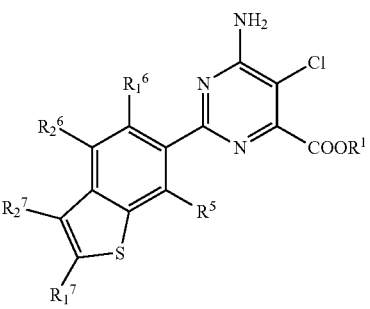

| Ex. No. | $R^1$ | $R^5$ | $R_1^6$ | $R_2^6$ | $R_1^7$ | $R_2^7$ |
|---|---|---|---|---|---|---|
| 37.146 | Et | F | H | H | F | Cl |
| 37.147 | Et | F | H | H | F | F |
| 37.148 | Et | F | H | H | F | Me |
| 37.149 | Et | F | H | H | Cl | H |
| 37.150 | Et | F | H | H | Cl | F |
| 37.151 | Et | F | H | H | Cl | Cl |
| 37.152 | Et | F | H | H | Cl | Me |
| 37.153 | Et | F | H | H | Me | H |
| 37.154 | Et | F | H | H | Me | Cl |
| 37.155 | Et | F | H | H | Me | F |
| 37.156 | Et | F | H | H | Me | Me |
| 37.157 | Et | F | H | H | Ph | H |
| 37.158 | Et | F | H | H | Ph | Cl |
| 37.159 | Et | F | H | H | Ph | F |
| 37.160 | Et | F | H | H | Ph | Me |
| 37.161 | Et | Cl | H | H | H | H |
| 37.162 | Et | Cl | H | H | H | Cl |
| 37.163 | Et | Cl | H | H | H | F |
| 37.164 | Et | Cl | H | H | H | Me |
| 37.165 | Et | Cl | H | H | F | H |
| 37.166 | Et | Cl | H | H | F | Cl |
| 37.167 | Et | Cl | H | H | F | F |
| 37.168 | Et | Cl | H | H | F | Me |
| 37.169 | Et | Cl | H | H | Cl | H |
| 37.170 | Et | Cl | H | H | Cl | F |
| 37.171 | Et | Cl | H | H | Cl | Cl |
| 37.172 | Et | Cl | H | H | Cl | Me |
| 37.173 | Et | Cl | H | H | Me | H |
| 37.174 | Et | Cl | H | H | Me | Cl |
| 37.175 | Et | Cl | H | H | Me | F |
| 37.176 | Et | Cl | H | H | Me | Me |
| 37.177 | Et | Cl | H | H | Ph | H |
| 37.178 | Et | Cl | H | H | Ph | Cl |
| 37.179 | Et | Cl | H | H | Ph | F |
| 37.180 | Et | Cl | H | H | Ph | Me |
| 37.181 | H | F | F | H | H | H |
| 37.182 | H | F | H | F | H | H |

TABLE 38

Compounds according to the invention of the formula (I) in which X represents N, A represents A15, $R^8$, $R^3$ and $R^4$ each represent hydrogen and $R^2$ represents chlorine:

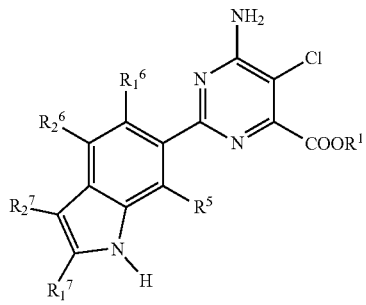

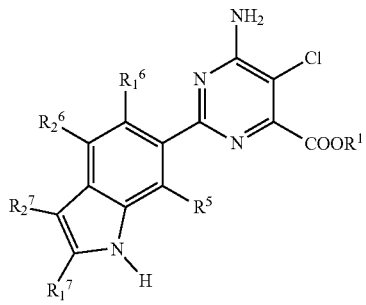

| Ex. No. | $R^1$ | $R^5$ | $R_1^6$ | $R_2^6$ | $R_1^7$ | $R_2^7$ |
|---|---|---|---|---|---|---|
| 38.001 | H | H | H | H | H | H |
| 38.002 | H | H | H | H | H | Cl |
| 38.003 | H | H | H | H | H | F |
| 38.004 | H | H | H | H | H | Me |
| 38.005 | H | H | H | H | F | H |
| 38.006 | H | H | H | H | F | Cl |
| 38.007 | H | H | H | H | F | F |
| 38.008 | H | H | H | H | F | Me |
| 38.009 | H | H | H | H | Cl | H |
| 38.010 | H | H | H | H | Cl | F |
| 38.011 | H | H | H | H | Cl | Cl |
| 38.012 | H | H | H | H | Cl | Me |
| 38.013 | H | H | H | H | Me | H |
| 38.014 | H | H | H | H | Me | Cl |
| 38.015 | H | H | H | H | Me | F |
| 38.016 | H | H | H | H | Me | Me |
| 38.017 | H | H | H | H | Ph | H |
| 38.018 | H | H | H | H | Ph | Cl |
| 38.019 | H | H | H | H | Ph | F |
| 38.020 | H | H | H | H | Ph | Me |
| 38.021 | H | F | H | H | H | H |
| 38.022 | H | F | H | H | H | Cl |
| 38.023 | H | F | H | H | H | F |
| 38.024 | H | F | H | H | H | Me |
| 38.025 | H | F | H | H | F | H |
| 38.026 | H | F | H | H | F | Cl |
| 38.027 | H | F | H | H | F | F |
| 38.028 | H | F | H | H | F | Me |
| 38.029 | H | F | H | H | Cl | H |
| 38.030 | H | F | H | H | Cl | F |
| 38.031 | H | F | H | H | Cl | Cl |
| 38.032 | H | F | H | H | Cl | Me |
| 38.033 | H | F | H | H | Me | H |
| 38.034 | H | F | H | H | Me | Cl |
| 38.035 | H | F | H | H | Me | F |
| 38.036 | H | F | H | H | Me | Me |
| 38.037 | H | F | H | H | Ph | H |
| 38.038 | H | F | H | H | Ph | Cl |
| 38.039 | H | F | H | H | Ph | F |
| 38.040 | H | F | H | H | Ph | Me |
| 38.041 | H | Cl | H | H | H | H |
| 38.042 | H | Cl | H | H | H | Cl |
| 38.043 | H | Cl | H | H | H | F |
| 38.044 | H | Cl | H | H | H | Me |
| 38.045 | H | Cl | H | H | F | H |
| 38.046 | H | Cl | H | H | F | Cl |
| 38.047 | H | Cl | H | H | F | F |
| 38.048 | H | Cl | H | H | F | Me |
| 38.049 | H | Cl | H | H | Cl | H |
| 38.050 | H | Cl | H | H | Cl | F |
| 38.051 | H | Cl | H | H | Cl | Cl |
| 38.052 | H | Cl | H | H | Cl | Me |
| 38.053 | H | Cl | H | H | Me | H |
| 38.054 | H | Cl | H | H | Me | Cl |
| 38.055 | H | Cl | H | H | Me | F |
| 38.056 | H | Cl | H | H | Me | Me |
| 38.057 | H | Cl | H | H | Ph | H |
| 38.058 | H | Cl | H | H | Ph | Cl |
| 38.059 | H | Cl | H | H | Ph | F |
| 38.060 | H | Cl | H | H | Ph | Me |
| 38.061 | Me | H | H | H | H | H |
| 38.062 | Me | H | H | H | H | Cl |
| 38.063 | Me | H | H | H | H | F |
| 38.064 | Me | H | H | H | H | Me |
| 38.065 | Me | H | H | H | F | H |
| 38.066 | Me | H | H | H | F | Cl |
| 38.067 | Me | H | H | H | F | F |
| 38.068 | Me | H | H | H | F | Me |
| 38.069 | Me | H | H | H | Cl | H |
| 38.070 | Me | H | H | H | Cl | F |
| 38.071 | Me | H | H | H | Cl | Cl |
| 38.072 | Me | H | H | H | Cl | Me |
| 38.073 | Me | H | H | H | Me | H |
| 38.074 | Me | H | H | H | Me | Cl |
| 38.075 | Me | H | H | H | Me | F |
| 38.076 | Me | H | H | H | Me | Me |
| 38.077 | Me | H | H | H | Ph | H |
| 38.078 | Me | H | H | H | Ph | Cl |
| 38.079 | Me | H | H | H | Ph | F |
| 38.080 | Me | H | H | H | Ph | Me |
| 38.081 | Me | F | H | H | H | H |
| 38.082 | Me | F | H | H | H | Cl |
| 38.083 | Me | F | H | H | H | F |
| 38.084 | Me | F | H | H | H | Me |
| 38.085 | Me | F | H | H | F | H |
| 38.086 | Me | F | H | H | F | Cl |
| 38.087 | Me | F | H | H | F | F |
| 38.088 | Me | F | H | H | F | Me |
| 38.089 | Me | F | H | H | Cl | H |
| 38.090 | Me | F | H | H | Cl | F |
| 38.091 | Me | F | H | H | Cl | Cl |
| 38.092 | Me | F | H | H | Cl | Me |
| 38.093 | Me | F | H | H | Me | H |
| 38.094 | Me | F | H | H | Me | Cl |
| 38.095 | Me | F | H | H | Me | F |
| 38.096 | Me | F | H | H | Me | Me |
| 38.097 | Me | F | H | H | Ph | H |
| 38.098 | Me | F | H | H | Ph | Cl |
| 38.099 | Me | F | H | H | Ph | F |
| 38.100 | Me | F | H | H | Ph | Me |
| 38.101 | Me | Cl | H | H | H | H |
| 38.102 | Me | Cl | H | H | H | Cl |
| 38.103 | Me | Cl | H | H | H | F |
| 38.104 | Me | Cl | H | H | H | Me |
| 38.105 | Me | Cl | H | H | F | H |
| 38.106 | Me | Cl | H | H | F | Cl |
| 38.107 | Me | Cl | H | H | F | F |
| 38.108 | Me | Cl | H | H | F | Me |
| 38.109 | Me | Cl | H | H | Cl | H |
| 38.110 | Me | Cl | H | H | Cl | F |
| 38.111 | Me | Cl | H | H | Cl | Cl |
| 38.112 | Me | Cl | H | H | Cl | Me |
| 38.113 | Me | Cl | H | H | Me | H |
| 38.114 | Me | Cl | H | H | Me | Cl |
| 38.115 | Me | Cl | H | H | Me | F |
| 38.116 | Me | Cl | H | H | Me | Me |
| 38.117 | Me | Cl | H | H | Ph | H |
| 38.118 | Me | Cl | H | H | Ph | Cl |

TABLE 38-continued

Compounds according to the invention of the formula (I) in which X represents N, A represents A15, $R^8$, $R^3$ and $R^4$ each represent hydrogen and $R^2$ represents chlorine:

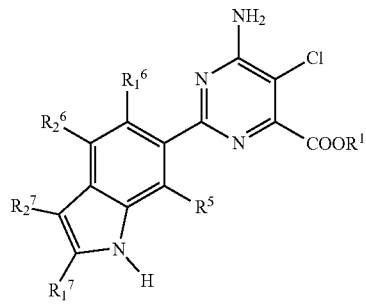

| Ex. No. | $R^1$ | $R^5$ | $R_1^6$ | $R_2^6$ | $R_1^7$ | $R_2^7$ |
|---|---|---|---|---|---|---|
| 38.119 | Me | Cl | H | H | Ph | F |
| 38.120 | Me | Cl | H | H | Ph | Me |
| 38.121 | Et | H | H | H | H | H |
| 38.122 | Et | H | H | H | H | Cl |
| 38.123 | Et | H | H | H | H | F |
| 38.124 | Et | H | H | H | H | Me |
| 38.125 | Et | H | H | H | F | H |
| 38.126 | Et | H | H | H | F | Cl |
| 38.127 | Et | H | H | H | F | F |
| 38.128 | Et | H | H | H | F | Me |
| 38.129 | Et | H | H | H | Cl | H |
| 38.130 | Et | H | H | H | Cl | F |
| 38.131 | Et | H | H | H | Cl | Cl |
| 38.132 | Et | H | H | H | Cl | Me |
| 38.133 | Et | H | H | H | Me | H |
| 38.134 | Et | H | H | H | Me | Cl |
| 38.135 | Et | H | H | H | Me | F |
| 38.136 | Et | H | H | H | Me | Me |
| 38.137 | Et | H | H | H | Ph | H |
| 38.138 | Et | H | H | H | Ph | Cl |
| 38.139 | Et | H | H | H | Ph | F |
| 38.140 | Et | H | H | H | Ph | Me |
| 38.141 | Et | F | H | H | H | H |
| 38.142 | Et | F | H | H | H | Cl |
| 38.143 | Et | F | H | H | H | F |
| 38.144 | Et | F | H | H | H | Me |
| 38.145 | Et | F | H | H | F | H |
| 38.146 | Et | F | H | H | F | Cl |
| 38.147 | Et | F | H | H | F | F |
| 38.148 | Et | F | H | H | F | Me |
| 38.149 | Et | F | H | H | Cl | H |
| 38.150 | Et | F | H | H | Cl | F |
| 38.151 | Et | F | H | H | Cl | Cl |
| 38.152 | Et | F | H | H | Cl | Me |
| 38.153 | Et | F | H | H | Me | H |
| 38.154 | Et | F | H | H | Me | Cl |
| 38.155 | Et | F | H | H | Me | F |
| 38.156 | Et | F | H | H | Me | Me |
| 38.157 | Et | F | H | H | Ph | H |
| 38.158 | Et | F | H | H | Ph | Cl |
| 38.159 | Et | F | H | H | Ph | F |
| 38.160 | Et | F | H | H | Ph | Me |
| 38.161 | Et | Cl | H | H | H | H |
| 38.162 | Et | Cl | H | H | H | Cl |
| 38.163 | Et | Cl | H | H | H | F |
| 38.164 | Et | Cl | H | H | H | Me |
| 38.165 | Et | Cl | H | H | F | H |
| 38.166 | Et | Cl | H | H | F | Cl |
| 38.167 | Et | Cl | H | H | F | F |
| 38.168 | Et | Cl | H | H | F | Me |
| 38.169 | Et | Cl | H | H | Cl | H |
| 38.170 | Et | Cl | H | H | Cl | F |
| 38.171 | Et | Cl | H | H | Cl | Cl |
| 38.172 | Et | Cl | H | H | Cl | Me |
| 38.173 | Et | Cl | H | H | Me | H |
| 38.174 | Et | Cl | H | H | Me | Cl |
| 38.175 | Et | Cl | H | H | Me | F |
| 38.176 | Et | Cl | H | H | Me | Me |
| 38.177 | Et | Cl | H | H | Ph | H |

TABLE 38-continued

Compounds according to the invention of the formula (I) in which X represents N, A represents A15, $R^8$, $R^3$ and $R^4$ each represent hydrogen and $R^2$ represents chlorine:

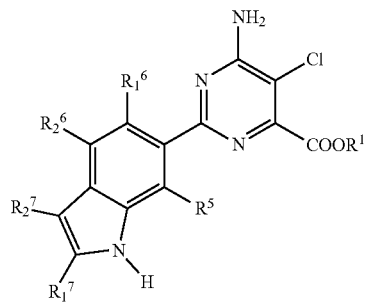

| Ex. No. | $R^1$ | $R^5$ | $R_1^6$ | $R_2^6$ | $R_1^7$ | $R_2^7$ |
|---|---|---|---|---|---|---|
| 38.178 | Et | Cl | H | H | Ph | Cl |
| 38.179 | Et | Cl | H | H | Ph | F |
| 38.180 | Et | Cl | H | H | Ph | Me |
| 38.181 | H | F | F | H | H | H |
| 38.182 | H | F | H | F | H | H |

TABLE 39

Compounds according to the invention of the formula (I) in which X represents N, A represents A15, $R^8$ represents methyl, $R^3$ and $R^4$ each represent hydrogen and $R^2$ represents chlorine:

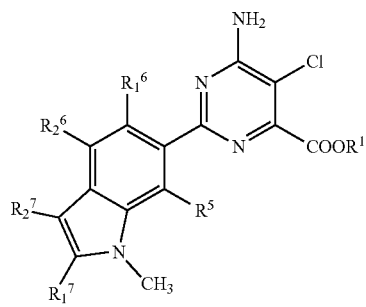

| Ex. No. | $R^1$ | $R^5$ | $R_1^6$ | $R_2^6$ | $R_1^7$ | $R_2^7$ |
|---|---|---|---|---|---|---|
| 39.001 | H | H | H | H | H | H |
| 39.002 | H | H | H | H | H | Cl |
| 39.003 | H | H | H | H | H | F |
| 39.004 | H | H | H | H | H | Me |
| 39.005 | H | H | H | H | F | H |
| 39.006 | H | H | H | H | F | Cl |
| 39.007 | H | H | H | H | F | F |
| 39.008 | H | H | H | H | F | Me |
| 39.009 | H | H | H | H | Cl | H |
| 39.010 | H | H | H | H | Cl | F |
| 39.011 | H | H | H | H | Cl | Cl |
| 39.012 | H | H | H | H | Cl | Me |
| 39.013 | H | H | H | H | Me | H |
| 39.014 | H | H | H | H | Me | Cl |
| 39.015 | H | H | H | H | Me | F |
| 39.016 | H | H | H | H | Me | Me |
| 39.017 | H | H | H | H | Ph | H |
| 39.018 | H | H | H | H | Ph | Cl |
| 39.019 | H | H | H | H | Ph | F |
| 39.020 | H | H | H | H | Ph | Me |
| 39.021 | H | F | H | H | H | H |
| 39.022 | H | F | H | H | H | Cl |
| 39.023 | H | F | H | H | H | F |
| 39.024 | H | F | H | H | H | Me |
| 39.025 | H | F | H | H | F | H |
| 39.026 | H | F | H | H | F | Cl |
| 39.027 | H | F | H | H | F | F |

TABLE 39-continued

Compounds according to the invention of the formula (I) in which X represents N, A represents A15, $R^8$ represents methyl, $R^3$ and $R^4$ each represent hydrogen and $R^2$ represents chlorine:

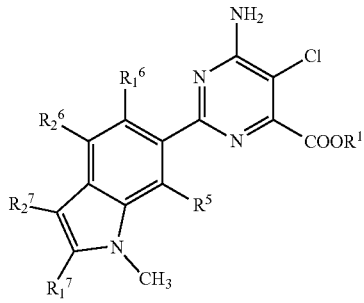

| Ex. No. | $R^1$ | $R^5$ | $R_1^6$ | $R_2^6$ | $R_1^7$ | $R_2^7$ |
|---|---|---|---|---|---|---|
| 39.028 | H | F | H | H | F | Me |
| 39.029 | H | F | H | H | Cl | H |
| 39.030 | H | F | H | H | Cl | F |
| 39.031 | H | F | H | H | Cl | Cl |
| 39.032 | H | F | H | H | Cl | Me |
| 39.033 | H | F | H | H | Me | H |
| 39.034 | H | F | H | H | Me | Cl |
| 39.035 | H | F | H | H | Me | F |
| 39.036 | H | F | H | H | Me | Me |
| 39.037 | H | F | H | H | Ph | H |
| 39.038 | H | F | H | H | Ph | Cl |
| 39.039 | H | F | H | H | Ph | F |
| 39.040 | H | F | H | H | Ph | Me |
| 39.041 | H | Cl | H | H | H | H |
| 39.042 | H | Cl | H | H | H | Cl |
| 39.043 | H | Cl | H | H | H | F |
| 39.044 | H | Cl | H | H | H | Me |
| 39.045 | H | Cl | H | H | F | H |
| 39.046 | H | Cl | H | H | F | Cl |
| 39.047 | H | Cl | H | H | F | F |
| 39.048 | H | Cl | H | H | F | Me |
| 39.049 | H | Cl | H | H | Cl | H |
| 39.050 | H | Cl | H | H | Cl | F |
| 39.051 | H | Cl | H | H | Cl | Cl |
| 39.052 | H | Cl | H | H | Cl | Me |
| 39.053 | H | Cl | H | H | Me | H |
| 39.054 | H | Cl | H | H | Me | Cl |
| 39.055 | H | Cl | H | H | Me | F |
| 39.056 | H | Cl | H | H | Me | Me |
| 39.057 | H | Cl | H | H | Ph | H |
| 39.058 | H | Cl | H | H | Ph | Cl |
| 39.059 | H | Cl | H | H | Ph | F |
| 39.060 | H | Cl | H | H | Ph | Me |
| 39.061 | Me | H | H | H | H | H |
| 39.062 | Me | H | H | H | H | Cl |
| 39.063 | Me | H | H | H | H | F |
| 39.064 | Me | H | H | H | H | Me |
| 39.065 | Me | H | H | H | F | H |
| 39.066 | Me | H | H | H | F | Cl |
| 39.067 | Me | H | H | H | F | F |
| 39.068 | Me | H | H | H | F | Me |
| 39.069 | Me | H | H | H | Cl | H |
| 39.070 | Me | H | H | H | Cl | F |
| 39.071 | Me | H | H | H | Cl | Cl |
| 39.072 | Me | H | H | H | Cl | Me |
| 39.073 | Me | H | H | H | Me | H |
| 39.074 | Me | H | H | H | Me | Cl |
| 39.075 | Me | H | H | H | Me | F |
| 39.076 | Me | H | H | H | Me | Me |
| 39.077 | Me | H | H | H | Ph | H |
| 39.078 | Me | H | H | H | Ph | Cl |
| 39.079 | Me | H | H | H | Ph | F |
| 39.080 | Me | H | H | H | Ph | Me |
| 39.081 | Me | F | H | H | H | H |
| 39.082 | Me | F | H | H | H | Cl |
| 39.083 | Me | F | H | H | H | F |
| 39.084 | Me | F | H | H | H | Me |
| 39.085 | Me | F | H | H | F | H |
| 39.086 | Me | F | H | H | F | Cl |
| 39.087 | Me | F | H | H | F | F |
| 39.088 | Me | F | H | H | F | Me |
| 39.089 | Me | F | H | H | Cl | H |
| 39.090 | Me | F | H | H | Cl | F |
| 39.091 | Me | F | H | H | Cl | Cl |
| 39.092 | Me | F | H | H | Cl | Me |
| 39.093 | Me | F | H | H | Me | H |
| 39.094 | Me | F | H | H | Me | Cl |
| 39.095 | Me | F | H | H | Me | F |
| 39.096 | Me | F | H | H | Me | Me |
| 39.097 | Me | F | H | H | Ph | H |
| 39.098 | Me | F | H | H | Ph | Cl |
| 39.099 | Me | F | H | H | Ph | F |
| 39.100 | Me | F | H | H | Ph | Me |
| 39.101 | Me | Cl | H | H | H | H |
| 39.102 | Me | Cl | H | H | H | Cl |
| 39.103 | Me | Cl | H | H | H | F |
| 39.104 | Me | Cl | H | H | H | Me |
| 39.105 | Me | Cl | H | H | F | H |
| 39.106 | Me | Cl | H | H | F | Cl |
| 39.107 | Me | Cl | H | H | F | F |
| 39.108 | Me | Cl | H | H | F | Me |
| 39.109 | Me | Cl | H | H | Cl | H |
| 39.110 | Me | Cl | H | H | Cl | F |
| 39.111 | Me | Cl | H | H | Cl | Cl |
| 39.112 | Me | Cl | H | H | Cl | Me |
| 39.113 | Me | Cl | H | H | Me | H |
| 39.114 | Me | Cl | H | H | Me | Cl |
| 39.115 | Me | Cl | H | H | Me | F |
| 39.116 | Me | Cl | H | H | Me | Me |
| 39.117 | Me | Cl | H | H | Ph | H |
| 39.118 | Me | Cl | H | H | Ph | Cl |
| 39.119 | Me | Cl | H | H | Ph | F |
| 39.120 | Me | Cl | H | H | Ph | Me |
| 39.121 | Et | H | H | H | H | H |
| 39.122 | Et | H | H | H | H | Cl |
| 39.123 | Et | H | H | H | H | F |
| 39.124 | Et | H | H | H | H | Me |
| 39.125 | Et | H | H | H | F | H |
| 39.126 | Et | H | H | H | F | Cl |
| 39.127 | Et | H | H | H | F | F |
| 39.128 | Et | H | H | H | F | Me |
| 39.129 | Et | H | H | H | Cl | H |
| 39.130 | Et | H | H | H | Cl | F |
| 39.131 | Et | H | H | H | Cl | Cl |
| 39.132 | Et | H | H | H | Cl | Me |
| 39.133 | Et | H | H | H | Me | H |
| 39.134 | Et | H | H | H | Me | Cl |
| 39.135 | Et | H | H | H | Me | F |
| 39.136 | Et | H | H | H | Me | Me |
| 39.137 | Et | H | H | H | Ph | H |
| 39.138 | Et | H | H | H | Ph | Cl |
| 39.139 | Et | H | H | H | Ph | F |
| 39.140 | Et | H | H | H | Ph | Me |
| 39.141 | Et | F | H | H | H | H |
| 39.142 | Et | F | H | H | H | Cl |
| 39.143 | Et | F | H | H | H | F |
| 39.144 | Et | F | H | H | H | Me |
| 39.145 | Et | F | H | H | F | H |

TABLE 39-continued

Compounds according to the invention of the formula (I) in which X represents N, A represents A15, $R^8$ represents methyl, $R^3$ and $R^4$ each represent hydrogen and $R^2$ represents chlorine:

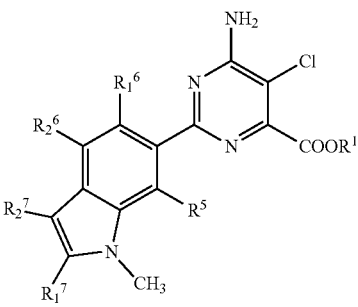

| Ex. No. | $R^1$ | $R^5$ | $R_1^6$ | $R_2^6$ | $R_1^7$ | $R_2^7$ |
|---|---|---|---|---|---|---|
| 39.146 | Et | F | H | H | F | Cl |
| 39.147 | Et | F | H | H | F | F |
| 39.148 | Et | F | H | H | F | Me |
| 39.149 | Et | F | H | H | Cl | H |
| 39.150 | Et | F | H | H | Cl | F |
| 39.151 | Et | F | H | H | Cl | Cl |
| 39.152 | Et | F | H | H | Cl | Me |
| 39.153 | Et | F | H | H | Me | H |
| 39.154 | Et | F | H | H | Me | Cl |
| 39.155 | Et | F | H | H | Me | F |
| 39.156 | Et | F | H | H | Me | Me |
| 39.157 | Et | F | H | H | Ph | H |
| 39.158 | Et | F | H | H | Ph | Cl |
| 39.159 | Et | F | H | H | Ph | F |
| 39.160 | Et | F | H | H | Ph | Me |
| 39.161 | Et | Cl | H | H | H | H |
| 39.162 | Et | Cl | H | H | H | Cl |
| 39.163 | Et | Cl | H | H | H | F |
| 39.164 | Et | Cl | H | H | H | Me |
| 39.165 | Et | Cl | H | H | F | H |
| 39.166 | Et | Cl | H | H | F | Cl |
| 39.167 | Et | Cl | H | H | F | F |
| 39.168 | Et | Cl | H | H | F | Me |
| 39.169 | Et | Cl | H | H | Cl | H |
| 39.170 | Et | Cl | H | H | Cl | F |
| 39.171 | Et | Cl | H | H | Cl | Cl |
| 39.172 | Et | Cl | H | H | Cl | Me |
| 39.173 | Et | Cl | H | H | Me | H |
| 39.174 | Et | Cl | H | H | Me | Cl |
| 39.175 | Et | Cl | H | H | Me | F |
| 39.176 | Et | Cl | H | H | Me | Me |
| 39.177 | Et | Cl | H | H | Ph | H |
| 39.178 | Et | Cl | H | H | Ph | Cl |
| 39.179 | Et | Cl | H | H | Ph | F |
| 39.180 | Et | Cl | H | H | Ph | Me |
| 39.181 | H | F | F | H | H | H |
| 39.182 | H | F | H | F | H | H |

TABLE 40

Compounds according to the invention of the formula (I) in which X represents N, A represents A16, $R^3$ and $R^4$ each represent hydrogen and $R^2$ represents chlorine:

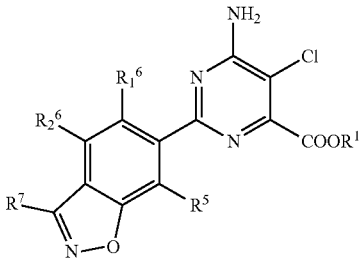

| Ex. No. | $R^1$ | $R^5$ | $R_1^6$ | $R_2^6$ | $R^7$ |
|---|---|---|---|---|---|
| 40.001 | H | H | H | H | H |
| 40.002 | H | H | H | H | Me |
| 40.003 | H | H | H | H | Ph |
| 40.004 | H | H | H | H | F |
| 40.005 | H | H | H | H | Cl |
| 40.006 | H | Cl | H | H | H |
| 40.007 | H | Cl | H | H | Me |
| 40.008 | H | Cl | H | H | Ph |
| 40.009 | H | Cl | H | H | F |
| 40.010 | H | Cl | H | H | Cl |
| 40.011 | H | F | H | H | H |
| 40.012 | H | F | H | H | Me |
| 40.013 | H | F | H | H | Ph |
| 40.014 | H | F | H | H | F |
| 40.015 | H | F | H | H | Cl |
| 40.016 | Me | H | H | H | H |
| 40.017 | Me | H | H | H | Me |
| 40.018 | Me | H | H | H | Ph |
| 40.019 | Me | H | H | H | F |
| 40.020 | Me | H | H | H | Cl |
| 40.021 | Me | Cl | H | H | H |
| 40.022 | Me | Cl | H | H | Me |
| 40.023 | Me | Cl | H | H | Ph |
| 40.024 | Me | Cl | H | H | F |
| 40.025 | Me | Cl | H | H | Cl |
| 40.026 | Et | H | H | H | H |
| 40.027 | Et | H | H | H | Me |
| 40.028 | Et | H | H | H | Ph |
| 40.029 | Et | H | H | H | F |
| 40.030 | Et | H | H | H | Cl |
| 40.031 | Et | F | H | H | H |
| 40.032 | Et | F | H | H | Me |
| 40.033 | Et | F | H | H | Ph |
| 40.034 | Et | F | H | H | F |
| 40.035 | Et | F | H | H | Cl |
| 40.036 | Et | Cl | H | H | H |
| 40.037 | Et | Cl | H | H | Me |
| 40.038 | Et | Cl | H | H | Ph |
| 40.039 | Et | Cl | H | H | F |
| 40.040 | Et | Cl | H | H | Cl |
| 40.041 | H | F | F | H | H |
| 40.042 | H | F | H | F | H |

TABLE 41

Compounds according to the invention of the formula (I) in which X represents N, A represents A17, $R^3$ and $R^4$ each represent hydrogen and $R^2$ represents chlorine:

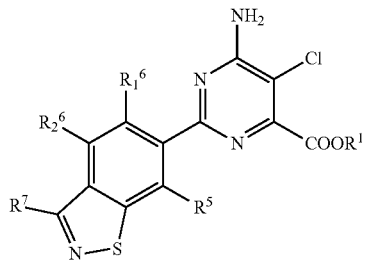

| Ex. No. | $R^1$ | $R^5$ | $R_1^6$ | $R_2^6$ | $R^7$ |
|---|---|---|---|---|---|
| 41.001 | H | H | H | H | H |
| 41.002 | H | H | H | H | Me |
| 41.003 | H | H | H | H | Ph |
| 41.004 | H | H | H | H | F |
| 41.005 | H | H | H | H | Cl |
| 41.006 | H | Cl | H | H | H |
| 41.007 | H | Cl | H | H | Me |
| 41.008 | H | Cl | H | H | Ph |
| 41.009 | H | Cl | H | H | F |
| 41.010 | H | Cl | H | H | Cl |
| 41.011 | H | F | H | H | H |
| 41.012 | H | F | H | H | Me |
| 41.013 | H | F | H | H | Ph |
| 41.014 | H | F | H | H | F |
| 41.015 | H | F | H | H | Cl |
| 41.016 | Me | H | H | H | H |
| 41.017 | Me | H | H | H | Me |
| 41.018 | Me | H | H | H | Ph |
| 41.019 | Me | H | H | H | F |
| 41.020 | Me | H | H | H | Cl |
| 41.021 | Me | Cl | H | H | H |
| 41.022 | Me | Cl | H | H | Me |
| 41.023 | Me | Cl | H | H | Ph |
| 41.024 | Me | Cl | H | H | F |
| 41.025 | Me | Cl | H | H | Cl |
| 41.026 | Et | H | H | H | H |
| 41.027 | Et | H | H | H | Me |
| 41.028 | Et | H | H | H | Ph |
| 41.029 | Et | H | H | H | F |
| 41.030 | Et | H | H | H | Cl |
| 41.031 | Et | F | H | H | H |
| 41.032 | Et | F | H | H | Me |
| 41.033 | Et | F | H | H | Ph |
| 41.034 | Et | F | H | H | F |
| 41.035 | Et | F | H | H | Cl |
| 41.036 | Et | Cl | H | H | H |
| 41.037 | Et | Cl | H | H | Me |
| 41.038 | Et | Cl | H | H | Ph |
| 41.039 | Et | Cl | H | H | F |
| 41.040 | Et | Cl | H | H | Cl |
| 41.041 | H | F | F | H | H |
| 41.042 | H | F | H | F | H |

TABLE 42

Compounds according to the invention of the formula (I) in which X represents N, A represents A18, $R^3$ and $R^4$ each represent hydrogen and $R^2$ represents chlorine:

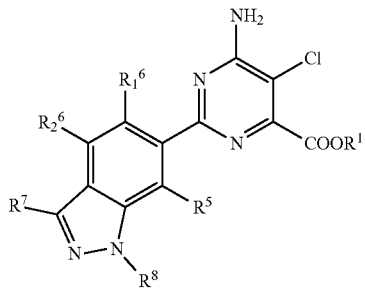

| Ex. No. | $R^1$ | $R^5$ | $R_1^6$ | $R_2^6$ | $R^7$ | $R^8$ |
|---|---|---|---|---|---|---|
| 42.001 | H | H | H | H | H | H |
| 42.002 | H | H | H | H | Me | H |
| 42.003 | H | H | H | H | Ph | H |
| 42.004 | H | H | H | H | F | Me |
| 42.005 | H | H | H | H | Cl | H |
| 42.006 | H | Cl | H | H | H | Me |
| 42.007 | H | Cl | H | H | Me | Me |
| 42.008 | H | Cl | H | H | Ph | Me |
| 42.009 | H | Cl | H | H | F | H |
| 42.010 | H | Cl | H | H | Cl | H |
| 42.011 | H | F | H | H | H | Me |
| 42.012 | H | F | H | H | Me | H |
| 42.013 | H | F | H | H | Ph | H |
| 42.014 | H | F | H | H | F | Me |
| 42.015 | H | F | H | H | Cl | Me |
| 42.016 | Me | H | H | H | H | Et |
| 42.017 | Me | H | H | H | Me | Et |
| 42.018 | Me | H | H | H | Ph | Et |
| 42.019 | Me | H | H | H | F | Et |
| 42.020 | Me | H | H | H | Cl | Et |
| 42.021 | Me | Cl | H | H | H | Me |
| 42.022 | Me | Cl | H | H | Me | H |
| 42.023 | Me | Cl | H | H | Ph | H |
| 42.024 | Me | Cl | H | H | F | H |
| 42.025 | Me | Cl | H | H | Cl | Et |
| 42.026 | Et | H | H | H | H | Me |
| 42.027 | Et | H | H | H | Me | Me |
| 42.028 | Et | H | H | H | Ph | Me |
| 42.029 | Et | H | H | H | F | H |
| 42.030 | Et | H | H | H | Cl | H |
| 42.031 | Et | F | H | H | H | Me |
| 42.032 | Et | F | H | H | Me | Me |
| 42.033 | Et | F | H | H | Ph | H |
| 42.034 | Et | F | H | H | F | Et |
| 42.035 | Et | F | H | H | Cl | Et |
| 42.036 | Et | Cl | H | H | H | H |
| 42.037 | Et | Cl | H | H | Me | H |
| 42.038 | Et | Cl | H | H | Ph | H |
| 42.039 | Et | Cl | H | H | F | Me |
| 42.040 | Et | Cl | H | H | Cl | H |
| 42.041 | H | F | F | H | H | H |
| 42.042 | H | F | H | F | H | H |

TABLE 43

Compounds according to the invention of the formula (I) in which X represents N, A represents A19, $R^3$ and $R^4$ each represent hydrogen and $R^2$ represents chlorine:

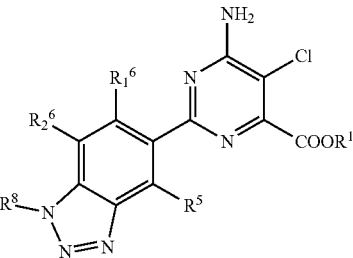

| Ex. No. | $R^1$ | $R^5$ | $R_1^6$ | $R_2^6$ | $R^8$ |
|---|---|---|---|---|---|
| 43.001 | H | H | H | H | H |
| 43.002 | H | H | H | H | Me |
| 43.003 | H | H | H | H | Et |
| 43.004 | H | F | H | H | H |
| 43.005 | H | F | H | H | Me |
| 43.006 | H | F | H | H | Et |
| 43.007 | H | Cl | H | H | H |
| 43.008 | H | Cl | H | H | Me |
| 43.009 | H | Cl | H | H | Et |
| 43.010 | Me | H | H | H | H |
| 43.011 | Me | H | H | H | Me |
| 43.012 | Me | H | H | H | Et |
| 43.013 | Me | F | H | H | H |
| 43.014 | Me | F | H | H | Me |
| 43.015 | Me | F | H | H | Et |
| 43.016 | Me | Cl | H | H | H |
| 43.017 | Me | Cl | H | H | Me |
| 43.018 | Me | Cl | H | H | Et |
| 43.019 | Et | H | H | H | H |
| 43.020 | Et | H | H | H | Me |
| 43.021 | Et | H | H | H | Et |
| 43.022 | Et | F | H | H | H |
| 43.023 | Et | F | H | H | Me |
| 43.024 | Et | F | H | H | Et |
| 43.025 | Et | Cl | H | H | H |
| 43.026 | Et | Cl | H | H | Me |
| 43.027 | Et | Cl | H | H | Et |
| 43.028 | H | F | F | H | H |
| 43.029 | H | F | H | F | H |

TABLE 44

Compounds according to the invention of the formula (I) in which X represents N, A represents A20, $R^3$ and $R^4$ each represent hydrogen and $R^2$ represents chlorine:

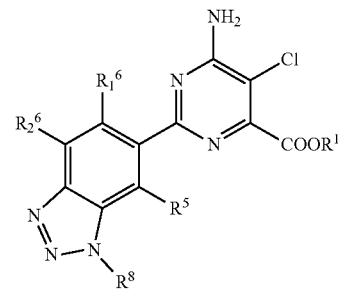

| Ex. No. | $R^1$ | $R^5$ | $R_1^6$ | $R_2^6$ | $R^8$ |
|---|---|---|---|---|---|
| 44.001 | H | H | H | H | Me |
| 44.002 | H | H | H | H | Et |
| 44.003 | H | F | H | H | Me |
| 44.004 | H | F | H | H | Et |
| 44.005 | H | Cl | H | H | Me |
| 44.006 | H | Cl | H | H | Et |
| 44.007 | Me | H | H | H | Me |
| 44.008 | Me | H | H | H | Et |
| 44.009 | Me | F | H | H | Me |
| 44.010 | Me | F | H | H | Et |
| 44.011 | Me | Cl | H | H | Me |
| 44.012 | Me | Cl | H | H | Et |
| 44.013 | Et | H | H | H | Me |
| 44.014 | Et | H | H | H | Et |
| 44.015 | Et | F | H | H | Me |
| 44.016 | Et | F | H | H | Et |
| 44.017 | Et | Cl | H | H | Me |
| 44.018 | Et | Cl | H | H | Et |
| 44.019 | H | F | F | H | Me |
| 44.020 | H | F | H | F | Me |

Collections of compounds of the formula (I) and/or salts thereof which can be synthesized by the aforementioned reactions can also be prepared in a parallel manner, it being possible for this to take place in a manual, partly automated or completely automated manner. In this connection, it is, for example, possible to automate the reaction procedure, the work-up or the purification of the products and/or intermediates. Overall, this is understood as meaning a procedure as described, for example, by D. Tiebes in Combinatorial Chemistry—Synthesis, Analysis, Screening (editor Günther Jung), Verlag Wiley 1999, on pages 1 to 34.

For the parallel reaction procedure and work-up, it is possible to use a series of commercially available instruments, for example Calpyso reaction blocks from Barnstead International, Dubuque, Iowa 52004-0797, USA or reaction stations from Radleys, Shirehill, Saffron Walden, Essex, CB 11 3AZ, England or MultiPROBE Automated Workstations from Perkin Elmer, Waltham, Mass. 02451, USA. For the parallel purification of compounds of the formula (I) and salts thereof or of intermediates produced during the preparation, there are available, inter alia, chromatography apparatuses, for example from ISCO, Inc., 4700 Superior Street, Lincoln, Nebr. 68504, USA.

The apparatuses listed lead to a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Caliper, Hopkinton, Mass. 01748, USA.

The implementation of single or several synthesis steps can be supported through the use of polymer-supported reagents/ scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described here, the preparation of compounds of the formula (I) and salts thereof can take place completely or partially by solid-phase-supported methods. For this purpose, individual intermediates or all intermediates in the synthesis or a synthesis adapted for the corresponding procedure are bonded to a synthesis resin. Solid-phase-supported synthesis methods are sufficiently described in the specialist literature, for example Barry A. Bunin in "The Combinatorial Index", Academic Press, 1998 and Combinatorial Chemistry—Synthesis, Analysis, Screening (editor Gunther Jung), Wiley, 1999. The use of solid-phase-supported synthesis methods permits a series of protocols known in the literature, which again can be carried out manually or in an automated manner. The reactions can be carried out, for example, by means of IRORI technology in microreactors from Nexus Biosystems, 12140 Community Road, Poway, Calif. 92064, USA.

Both on a solid phase and in liquid phase can the procedure of individual or several synthesis steps be supported through the use of microwave technology. The specialist literature describes a series of experimental protocols, for example in Microwaves in Organic and Medicinal Chemistry (editor C. O. Kappe and A. Stadler), Wiley, 2005.

The preparation according to the processes described here produces compounds of the formula (I) and their salts in the form of substance collections which are called libraries. The present invention also provides libraries which comprise at least two compounds of the formula (I) and their salts.

The compounds of the formula (I) according to the invention (and/or their salts), hereinbelow also referred to together as "compounds according to the invention", have excellent herbicidal efficacy against a broad spectrum of economically important monocotyledonous and dicotyledonous annual harmful plants. The active compounds act efficiently even on perennial harmful plants which produce shoots from rhizomes, root stocks and other perennial organs and which are difficult to control.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seed (for example grains, seeds or vegetative propagules such as tubers or shoot parts with buds) or to the area on which the plants grow (for example the area under cultivation). In this context, the compounds according to the invention can be applied for example pre-sowing (if appropriate also by incorporation into the soil), pre-emergence or post-emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant's metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and plant-growth-regulatory properties, the active compounds can also be employed for controlling harmful plants in crops of known genetically modified plants or genetically modified plants still to be developed. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other particular properties relate, for example, to the harvested material with regard to quantity, quality, storability, composition and specific constituents. Thus, transgenic plants are known whose starch content is increased, or whose starch quality is altered, or those where the harvested material has a different fatty acid composition. Other particular properties may be tolerant or resistant to abiotic stressors, for example heat, low temperatures, drought, salinity and ultraviolet radiation.

It is preferred to use the compounds of the formula (I) according to the invention or salts thereof in economically important transgenic crops of useful plants and ornamental plants, for example of cereals such as wheat, barley, rye, oats, sorghum and millet, rice, cassava and corn or else crops of sugar beet, cotton, soybean, oilseed rape, potato, tomato, peas and other vegetables.

It is preferred to employ the compounds of the formula (I) as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP 0221044, EP 0131624). For example, the following have been described in several cases:

genetic modifications of crop plants for the purposes of modifying the starch synthesized in the plants (for example WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377 A) or of the sulfonylurea type (EP 0257993 A, U.S. Pat. No. 5,013,659) or to combinations or mixtures of these herbicides through "gene stacking", such as transgenic crop plants e.g. corn or soybean with the tradename or the name Optimum™ GAT™ (glyphosate ALS tolerant), transgenic crop plants, for example cotton, which is capable of producing *Bacillus thuringiensis* toxins (Bt toxins), which make the plants resistant to certain pests (EP 0142924 A, EP 0193259 A), transgenic crop plants with a modified fatty acid composition (WO 91/013972 A), genetically modified crop plants with novel constituents or secondary metabolites, for example novel phytoalexins, which bring about an increased disease resistance (EP 0309862 A, EP 0464461 A), genetically modified plants with reduced photorespiration which feature higher yields and higher stress tolerance (EP 0305398 A), transgenic crop plants which produce pharmaceutically or diagnostically important proteins ("molecular pharming"), transgenic crop plants which are distinguished by higher yields or better quality, transgenic crop plants which are distinguished by a combination for example, of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, nucleic acid molecules which allow mutagenesis or a sequence change by recombination of DNA sequences can be introduced into plasmids. For example, standard methods allow base exchanges to be carried out, subsequences to be removed, or natural or synthetic sequences to be added. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone", VCH Weinheim 2nd edition 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds (I) according to the invention in transgenic crops which are resistant to growth regulators such as, for example, 2,4 D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, glyphosate, glufosinate or benzoylisoxazoles and analogous active compounds, or to any combinations of these active compounds.

Particularly preferably, the compounds according to the invention can be used in transgenic crop plants which are resistant to a combination of glyphosates and glufosinates, glyphosates and sulfonylureas or imidazolinones. Very particularly preferably, the compounds according to the invention can be used in transgenic crop plants such as e.g. corn or soybean with the tradename or the name Optimum™ GAT™ (glyphosate ALS tolerant).

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant-growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes. These individual types of formulation are known in principle and are described, for example, in: Winnacker-Küchler, "Chemische Technologie" [Chemical technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963, McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie", volume 7, C. Hanser Verlag Munich, 4th ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'dinaphthylmethane-6,6'-disulfonate, sodium dibutylnaphthalenesulfonate or else sodium oleoylmethyltaurinate. To prepare the wettable powders, the herbicidally active compounds are ground finely, for example in customary apparatuses such as hammer mills, blower mills and air-jet mills, and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be prepared either by spraying the active compound onto granulated inert material capable of adsorption or by applying active compound concentrates to the surface of carrier substances, such as sand, kaolinites or granulated inert material, by means of adhesives, for example polyvinyl alcohol, sodium polyacrylate or mineral oils. Suitable active compounds can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally from 0.1 to 99% by weight, in particular from 0.1 to 95% by weight, of compounds according to the invention. In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Formulations in the form of dusts comprise from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respectively customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2009 and the literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers. Here, by way of example, one and in some cases a plurality of use forms are mentioned:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulphamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ephephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl(2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

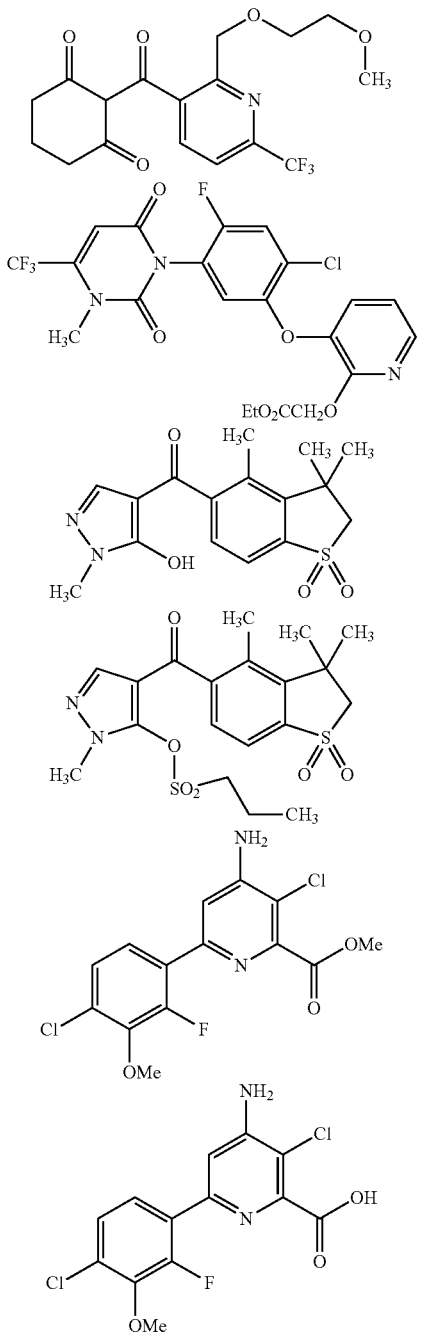

For application, the formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted further with other inert substances prior to application.

The required application rate of the compounds of the formula (I) varies according to the external conditions such as, inter alia, temperature, humidity and the type of herbicide used. It may vary within wide limits, for example between 0.001 and 1.0 kg/ha or more of active substance; however, preferably it is between 0.005 and 750 g/ha.

The examples below illustrate the invention:

A. CHEMICAL EXAMPLES

1. Preparation of methyl 4-amino-3-chloro-6-(7-fluoro-2-phenyl-1,3-benzoxazol-6-yl)pyridine-2-carboxylate (Example No. 8.019)

0.024 g (0.03 mmol) of $(PPh_3)_2PdCl_2$ is added to a solution of 0.3 g (1.13 mmol) of methyl 4-amino-6-bromo-3-chloropyridine-2-carboxylate in 20 ml of dioxane, and this mixture is stirred at room temperature (RT) for 30 min. In succession, 0.35 g (1.35 mmol) of (7-fluoro-2-phenyl-1,3-benzoxazol-6-yl)boronic acid, 0.47 g (3.4 mmol) of $K_2CO_3$ and 2 g (111 mmol) of $H_2O$ are then added to this mixture, which is then stirred under reflux for 6 h. The mixture is allowed to stand at RT for a further 12 h and then added to 40 ml of $H_2O$. This mixture is extracted repeatedly with $CH_2Cl_2$, and the combined organic phase is dried over $Na_2SO_4$ and then concentrated. Purification by chromatography on silica gel using the mobile phase heptane/ethyl acetate (3/7) gives 0.16 g (36%) of product. $^1$H-NMR (CDCl$_3$): δ 8.30, 8.00, 7.55 (3m, 5H, $C_6H_5$), 7.60, 7.55 (2d, 2H, benzoxazole ring), 7.30 (s, 1H, pyridine) 4.85 (bs, 2H, $NH_2$), 4.00 (S, 3H, $COOCH_3$).

2. Preparation of methyl 4-amino-3-chloro-6-(1,3-benzoxazol-6-yl)pyridine-2-carboxylate (Example No. 8.013)

0.024 g (0.03 mmol) of $(PPh_3)_2PdCl_2$ is added to a solution of 0.3 g (1.13 mmol) of methyl 4-amino-6-bromo-3-chloropyridine-2-carboxylate in 20 ml of dioxane, and this mixture is stirred at RT for 30 min. In succession, 0.28 g (1.13 mmol) of 6-(4,4,5,5-tetramethyl-1,3,2-dioxaborolan-2-yl)-1,3-benzoxazole, 0.47 g (3.4 mmol) of $K_2CO_3$ and 2 g (111 mmol) of $H_2O$ are then added to this mixture, which is then stirred under reflux for 6 h. The mixture is allowed to stand at RT for a further 12 h and then added to 40 ml of $H_2O$. This mixture is extracted repeatedly with $CH_2Cl_2$, and the combined organic phase is dried over $Na_2SO_4$ and then concentrated. Purification by chromatography on silica gel using the mobile phase heptane/ethyl acetate (3/7) gives 0.1 g (29%) of product. $^1$H-NMR (CDCl$_3$): δ 8.25 (s, 1H, benzoxazole), 8.15 (s, 1H, benzoxazole), 7.90, 7.80 (2d, 2H, benzoxazole), 7.20 (s, 1H, pyridine), 4.80 (bs, 2H, $NH_2$), 4.00 (s, 3H, $COOCH_3$).

3. Preparation of methyl 6-amino-5-chloro-2-(2-methyl-1,3-benzoxazol-5-yl)pyrimidine-4-carboxylate (Example No. 30.014)

0.024 g (0.03 mmol) of $(PPh_3)_2PdCl_2$ is added to a solution of 0.3 g (1.13 mmol) of methyl 6-amino-2-bromo-5-chloropyridine-4-carboxylate in 20 ml of dioxane, and this mixture is stirred at RT for 30 min. 0.29 g (1.13 mmol) of 2-methyl-5-(4,4,5,5-tetramethyl-1,3,2-dioxaborolan-2-yl)-1,3-benzoxazole, 0.47 g (3.4 mmol) of $K_2CO_3$ and 2 g (111 mmol) of $H_2O$ are then added, and the mixture is then stirred under reflux for 6 h. The reaction mixture is allowed to stand at RT for a further 12 h and then added to 40 ml of $H_2O$. This mixture is extracted repeatedly with $CH_2Cl_2$, and the combined organic phase is dried over $Na_2SO_4$ and then concentrated. Purification by chromatography on silica gel using the mobile phase heptane/ethyl acetate (3/7) gives 0.06 g (17%) of product. $^1$H-NMR (CDCl$_3$): δ 8.65 (d, 1H, benzoxazole), 8.40 (dd, 1H, benzoxazole), 7.50 (d, 1H, benzoxazole), 5.55 (bs, 2H, $NH_2$), 4.05 (s, 3H, $COOCH_3$) 2.70 (s, 3H, —$CH_3$).

In the table below, the NMR data of some compounds according to the invention are listed for characterization.

| Ex. No. | $^1$H-NMR δ (ppm) |
|---|---|
| 1.012 | CDCl3: 8.40d, 1H; 7.83d, 1H; 7.65, 1H; 7.53d, 1H; 7.12s, 1H; 4.80bs, 2H, NH2; 4.05s, 3H, COOMe |
| 1.038 | CDCl3: 8.40d, 1H; 7.62d, 1H; 7.57d, 1H; 7.20s, 1H; 6.70d, 1H; 4.80bs, 2H, NH2; 4.00s, 3H, COOMe |
| 2.012 | CDCl$_3$: 8.40d, 1H; 7.92d, 1H; 7.88dd, 1H; 7.46d, 1H; 7.39d, 1H; 7.18s, 1H; 4.8bs, NH$_2$; 4.02s, 3H, COOMe |
| 2.038 | CDCl3: 8.40d, 1H; 7.60d, 1H; 7.40d, 1H; 7.35d, 1H; 7.25s, 1H; 4.85bs, 2H, NH2; 4.00s, 3H, COOMe |
| 8.007 | DMSO-d$_6$: 8.45d, 2H; 8.20m, 1H; 7.80s, 1H; 7.70m, 3H; 7.40m; 1H |
| 8.013 | CDCl$_3$: 8.30s, 1H; 8.13s, 1H; 8.05d, 2H; 7.62d, 1H; 7.13s, 1H; 4.82bs, NH$_2$; 4.0s, 3H, COOMe |
| 8.014 | CDCl$_3$: 8.10s, 1H; 7.90d, 1H; 7.50d, 1H; 7.10s, 1H; 4.70bs, 2H, NH$_2$; 4.00s, 3H, COOMe; 2.65s, 3H, CH$_3$ |
| 8.019 | CDCl$_3$: 8.30m, 2H; 8.15m, 1H; 7.59m, 4H; 7.18m, 1H; 4.95bs, 2H, NH$_2$; 4.05s, 3H, COOMe |
| 8.039 | CDCl$_3$: 7.85s, 1H; 7.70d, 1H; 7.30d, 1H; 7.10s, 1H; 4.95bs, 2H, NH$_2$; 4.80bs, 2H, NH$_2$; 4.00s, 3H, COOMe |
| 9.013 | CDCl$_3$: 9.00s, 1H; 8.60s, 1H; 8.12d, 1H; 8.00d, 1H; 7.20s, 1H; 4.85bs, 2H, NH$_2$; 4.00s, 3H, COOMe |
| 9.014 | CDCl$_3$: 8.40s, 1H; 8.00d, 1H; 7.85d, 1H; 7.18s, 1H; 4.80bs, 2H, NH$_2$; 4.00s, 3H, COOMe |
| 10.013 | CDCl$_3$: 8.25s, 1H; 8.15s, 1H; 8.92d, 1H; 8.82d, 1H; 7.18s, 1H; 4.80bs, 2H, NH$_2$; 4.00s, 3H, COOMe |
| 10.014 | CDCl$_3$: 8.10s, 1H; 7.82d, 1H; 7.68d, 1H; 7.14s, 1H; 4.80bs, 2H, NH$_2$; 4.00s, 3H, COOMe; 2.68s, 3H, CH$_3$ |
| 10.019 | CDCl$_3$: 8.30m, 2H; 8.00dd, 1H; 7.60d, 1H; 7.57m, 3H; 7.30s, 1H; 4.85bs, 2H, NH$_2$; 4.00s 3H, COOMe |
| 10.023 | CDCl$_3$: 8.30m, 2H; 7.73d, 1H; 7.67s, 1H; 7.60m, 3H; 7.14s, 1H; 4.90bs, 2H, NH$_2$; 4.00s, 3H, COOMe |
| 11.014 | CDCl$_3$: 8.50s, 1H; 7.98d, 1H; 7.90d, 1H; 7.15s, 1H; 4.85bs, 2H, NH$_2$; 4.00s, 3H, COOMe; 2.85s, 3H, CH$_3$ |
| 14.061 | CDCl3: 8.20s, 1H; 7.80d, 1H; 7.65d, 1H; 7.60d, 1H; 7.15s, 1H; 6.78d, 1H; 4.80bs, 2H, NH2; 4.02s, 3H, COOMe |

-continued

| Ex. No. | ¹H-NMR δ (ppm) |
|---|---|
| 14.081 | CDCl3: 7.85dd, 1H; 7.70d, 2H; 7.40d, 2H; 7.30s, 1H; 6.70d, 1H; 4.80bs, 2H, NH2; 4.00s, 3H, COOMe |
| 15.061 | CDCl3: 8.50s, 1H; 7.89d, 1H; 7.85d, 1H; 7.50d, 1H; 7.35d, 1H; 7.20s, 1H; 4.80bs, 2H, NH2; 4.03s, 3H, COOMe |
| 16.064 | CDCl$_3$: 8.10s, 1H; 8.00bs, 1H, NH; 7.60m, 2H; 7.20s, 1H; 7.00s, 1H; 4.70bs, 2H, NH$_2$; 4.00s, 3H, COOMe; 2.35s, 3H, CH$_3$ |
| 16.073 | CDCl$_3$: 8.10bs, 1H, NH; 7.95s, 1H; 7.50m, 2H; 7.10s, 1H; 6.20s, 1H; 4.75bs, 2H; NH$_2$; 4.00s, 3H, COOMe; 2.45s, 3H, CH$_3$ |
| 24.012 | CDCl$_3$: 8.84s, 1H; 8.35d, 1H; 7.93d, 1H; 7.48d, 1H; 7.42d, 1H; 5.60bs, 2H, NH$_2$; 4.00s, 3H; COOMe |
| 30.014 | CDCl$_3$: 8.65s, 1H; 8.40d, 1H; 7.50d, 1H; 5.60bs, 2H, NH$_2$; 4.05s, 3H, COOMe; 2.70s, 3H, CH$_3$ |
| 31.013 | CDCl$_3$: 9.15s, 1H; 9.05s, 1H; 8.50d, 1H; 8.00d, 1H; 5.60bs, 2H, NH$_2$; 4.05s, 3H, COOMe |
| 32.013 | CDCl$_3$: 8.60s, 1H; 8.45d, 1H; 8.18s, 1H; 7.70d, 1H; 5.60bs, 2H, NH$_2$; 4.05s, 3H, COOMe |
| 33.014 | CDCl$_3$: 8.85s, 1H; 8.45d, 1H; 7.95s, 1H; 5.60bs, 2H, NH$_2$; 4.00s, 3H; COOMe; 2.85s, 3H, CH$_3$ |
| 38.061 | CDCl$_3$: 8.48s, 1H; 8.30bs, NH; 8.15d, 1H; 7.70d, 1H; 7.30d, 1H; 6.60d, 1H; 5.50bs, 2H, NH$_2$; 4.00s, 3H, COOMe |

B. FORMULATION EXAMPLES

1. Dusts

A dust is obtained by mixing 10 parts by weight of a compound of the general formula (I) and 90 parts by weight of talc as inert substance and comminuting the mixture in a hammer mill.

2. Dispersible Powder

A wettable powder which is readily dispersible in water is obtained by mixing 25 parts by weight of a compound of the general formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

3. Dispersion Concentrate

A readily water-dispersible dispersion concentrate is obtained by mixing 20 parts by weight of a compound of the general formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

4. Emusifiable Concentrate

An emulsifiable concentrate is obtained from 15 parts by weight of a compound of the general formula (I), 75 parts by weight of cyclohexanone as solvent and 10 parts by weight of oxethylated nonylphenol as emulsifier.

5. Water-Dispersible Granules

Water-dispersible granules are obtained by mixing 75 parts by weight of a compound of the general formula (I),
10" of calcium lignosulfonate,
5" of sodium laurylsulfate,
3" of polyvinyl alcohol and
7" of kaolin,
grinding the mixture in a pinned-disk mill, and granulating the powder in a fluidized bed by spraying on water as granulating liquid.

Water-dispersible granules are also obtained by homogenizing and precomminuting, in a colloid mill,
25 parts by weight of a compound of the general formula (I),
5" of sodium 2,2'-dinaphthylmethane-6,6'-disulfonate,
2" of sodium oleoylmethyltaurinate,
1" of polyvinyl alcohol,
17" of calcium carbonate and
50" of water,
subsequently grinding the mixture in a bead mill and atomizing and drying the resulting suspension in a spray tower by means of a single-substance nozzle.

C. BIOLOGICAL EXAMPLES

1. Pre-Emergence Herbicidal Action Against Harmful Plants

Seeds or rhizome pieces of mono- and dicotyledonous harmful plants are placed in sandy loam soil in pots having a diameter of 9 to 13 cm and covered with soil. The herbicides, formulated as emulsifiable concentrates or dusts, are then applied in various dosages as aqueous dispersions or suspensions or emulsions at an application rate of 300 to 800 l of water/ha (converted) to the surface of the covering soil. For further cultivation of the plants, the pots are then kept under optimum conditions in a greenhouse. After the test plants were left to stand in the greenhouse for 3 to 4 weeks under optimum growth conditions, the activity of the compounds according to the invention is scored visually. Thus, for example, the compounds of nos. 1.012, 1.038, 14.061 and 15.061 each show, at an application rate of 320 grams per hectare, an activity of at least 90% against *Echinocloa crus galli*, *Abutilon theophrasti*, *Amaranthus retroflexus*, *Matricaria inodora*, *Stellaria media* and *Veronica persica*.

2. Post-Emergence Herbicidal Action Against Harmful Plants

Seeds of monocotyledonous and dicotyledonous harmful plants are placed in sandy loam soil in cardboard pots, covered with soil and cultivated in a greenhouse under good growth conditions. Two to three weeks after sowing, the test plants are treated at the three-leaf stage. The compounds according to the invention, formulated as wettable powders or as emulsion concentrates, are sprayed onto the surface of the green parts of the plants at an application rate of 600 to 800 l of water/ha (converted). After the test plants were left to stand in the greenhouse for 3 to 4 weeks under optimum growth conditions, the effect of the compounds according to the invention is scored visually. Thus, for example, the compounds of nos. 1.012, 14.061 and 15.061 each show, at an application rate of 80 grams per hectare, an activity of at least 90% against Echinocloa crus galli, Abutilon theophrasti, Amaranthus retroflexus and Matricaria inodora.

The invention claimed is:

1. A compound of formula (I), comprising an N-oxide and/or a salt thereof

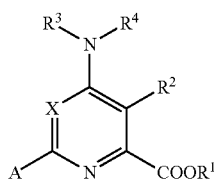

wherein
A represents a radical selected from the group consisting of A1, A2, A13, and A14

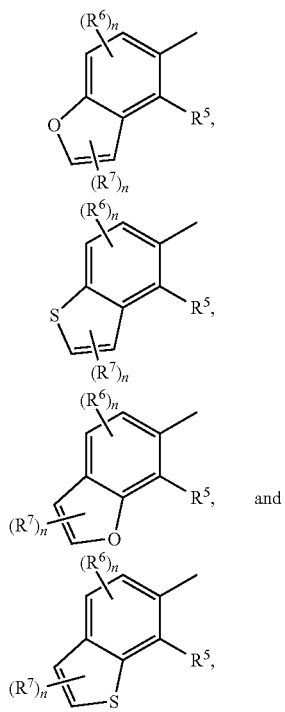

$R^1$ represents hydrogen or $(C_1-C_4)$-alkyl,
$R^2$ represents chlorine,
$R^3$ represents hydrogen,
$R^4$ represents hydrogen,
$R^5$ represents hydrogen, halogen, OH, $NH_2$, CN, $(C_1-C_3)$-alkyl, $(C_1-C_3)$-alkoxy, $(C_1-C_3)$-alkylamino or cyclopropyl,
$R^6$ represents hydrogen, halogen, OH, $NH_2$, CN, $(C_1-C_3)$-alkyl, $(C_1-C_3)$-alkoxy, cyclopropyl or vinyl,
$R^7$ represents hydrogen, halogen, $(C_1-C_3)$-alkyl, $(C_1-C_3)$-alkoxy, $(C_1-C_3)$-alkylthio, cyclopropyl, $(C_1-C_3)$-alkylamino or phenyl,
$R^8$ represents hydrogen, $(C_1-C_3)$-alkyl, phenyl or $(C_1-C_3)$-alkylcarbonyl,
X represents N, CH, CCl, CF or CBr, and
n represents 0, 1 or 2.

2. A herbicidal composition, comprising a herbicidally effective amount of at least one compound as claimed in claim 1.

3. The herbicidal composition as claimed in claim 2, in a mixture with at least one formulation auxiliary.

4. The herbicidal composition as claimed in claim 2, comprising at least one further pesticidally active compound selected from the group consisting of insecticides, acaricides, herbicides, fungicides, safeners and growth regulators.

5. The herbicidal composition as claimed in claim 4, comprising a safener.

6. The herbicidal composition as claimed in claim 5, comprising a further herbicide.

7. A method for controlling an unwanted plant, comprising applying an effective amount of at least one compound as claimed in claim 1, to a plant and/or on a site of unwanted plant growth.

8. A compound as claimed in claim 1, wherein said compound is capable of being used for controlling an unwanted plant in a plant crop.

9. A compound as claimed in claim 8, wherein the plant crop is a transgenic plant crop.

10. A method for controlling an unwanted plant, comprising applying an effective amount of a herbicidal composition as claimed in claim 2, to a plant and/or on a site of unwanted plant growth.

11. A compound as claimed in claim 1, wherein
A represents a radical

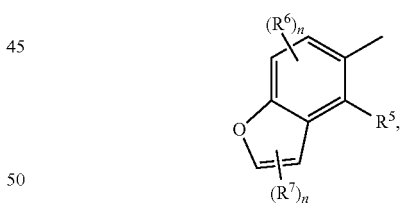

$R^1$ represents hydrogen or $(C_1-C_4)$-alkyl,
$R^2$ represents chlorine,
$R^3$ represents hydrogen,
$R^4$ represents hydrogen,
$R^5$ represents hydrogen, halogen, OH, $NH_2$, CN, $(C_1-C_3)$-alkyl, $(C_1-C_3)$-alkoxy, $(C_1-C_3)$-alkylamino or cyclopropyl,
$R^6$ represents hydrogen, halogen, OH, $NH_2$, CN, $(C_1-C_3)$-alkyl, $(C_1-C_3)$-alkoxy, cyclopropyl or vinyl,
$R^7$ represents hydrogen, halogen, $(C_1-C_3)$-alkyl, $(C_1-C_3)$-alkoxy, $(C_1-C_3)$-alkylthio, cyclopropyl, $(C_1-C_3)$-alkylamino or phenyl, and
n represents 0, 1 or 2.

12. A compound as claimed in claim 11 having the formula

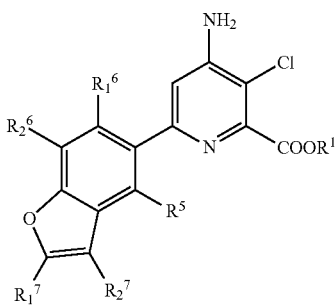

wherein
R¹ represents hydrogen or $(C_1-C_4)$-alkyl,
R⁵ represents hydrogen,
$R_1^6$ represents hydrogen or halogen,
$R_2^6$ represent hydrogen,
$R_1^7$ represents hydrogen, and
$R_2^7$ represent hydrogen.

13. A compound as claimed in claim 1, wherein
A represents a radical

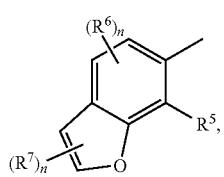

A13

R¹ represents hydrogen or $(C_1-C_4)$-alkyl,
R² represents chlorine,
R³ represents hydrogen,
R⁴ represents hydrogen,
R⁵ represents hydrogen, halogen, OH, NH₂, CN, $(C_1-C_3)$-alkyl, $(C_1-C_3)$-alkoxy, $(C_1-C_3)$-alkylamino or cyclopropyl,
R⁶ represents hydrogen, halogen, OH, NH₂, CN, $(C_1-C_3)$-alkyl, $(C_1-C_3)$-alkoxy, cyclopropyl or vinyl,
R⁷ represents hydrogen, halogen, $(C_1-C_3)$-alkyl, $(C_1-C_3)$-alkoxy, $(C_1-C_3)$-alkylthio, cyclopropyl, $(C_1-C_3)$-alkylamino or phenyl, and
n represents 0, 1 or 2.

14. A compound as claimed in claim 13 having the formula

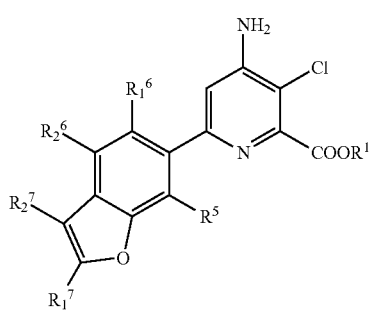

wherein
R¹ represents hydrogen or $(C_1-C_4)$-alkyl,
R⁵ represents hydrogen,
$R_1^6$ represents hydrogen,
$R_2^6$ represent hydrogen,
$R_1^7$ represents hydrogen, and
$R_2^7$ represent hydrogen.

15. A compound as claimed in claim 13 having the formula

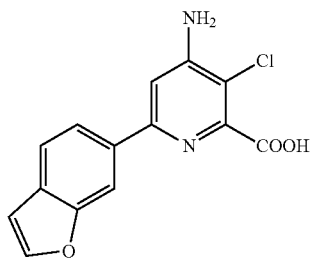

or the methyl ester thereof.

16. A compound as claimed in claim 1, wherein
A represents a radical

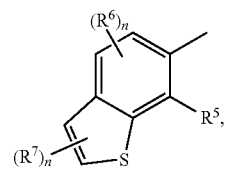

A14

R¹ represents hydrogen or $(C_1-C_4)$-alkyl,
R² represents chlorine,
R³ represents hydrogen,
R⁴ represents hydrogen,
R⁵ represents hydrogen, halogen, OH, NH₂, CN, $(C_1-C_3)$-alkyl, $(C_1-C_3)$-alkoxy, $(C_1-C_3)$-alkylamino or cyclopropyl,
R⁶ represents hydrogen, halogen, OH, NH₂, CN, $(C_1-C_3)$-alkyl, $(C_1-C_3)$-alkoxy, cyclopropyl or vinyl,
R⁷ represents hydrogen, halogen, $(C_1-C_3)$-alkyl, $(C_1-C_3)$-alkoxy, $(C_1-C_3)$-alkylthio, cyclopropyl, $(C_1-C_3)$-alkylamino or phenyl, and
n represents 0, 1 or 2.

17. A compound as claimed in claim 16 having the formula

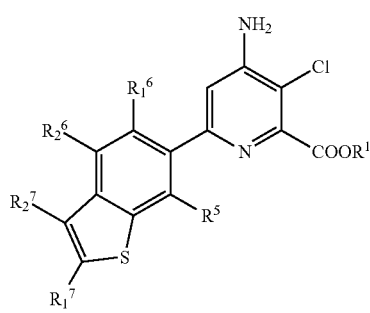

wherein
- $R^1$ represents hydrogen or $(C_1-C_4)$-alkyl,
- $R^5$ represents hydrogen,
- $R_1^6$ represents hydrogen,
- $R_2^6$ represent hydrogen,
- $R_1^7$ represents hydrogen, and
- $R_2^7$ represent hydrogen.

18. A compound as claimed in claim 16 having the formula

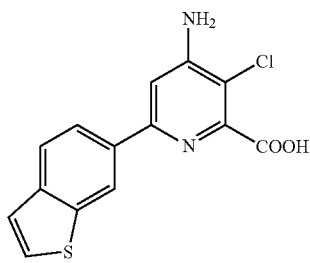

or the methyl ester thereof.

19. A compound as claimed in claim 1, wherein A represents a radical

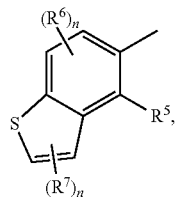 A2

- $R^1$ represents hydrogen or $(C_1-C_4)$-alkyl,
- $R^2$ represents chlorine,
- $R^3$ represents hydrogen,
- $R^4$ represents hydrogen,
- $R^5$ represents hydrogen, halogen, OH, $NH_2$, CN, $(C_1-C_3)$-alkyl, $(C_1-C_3)$-alkoxy, $(C_1-C_3)$-alkylamino or cyclopropyl,
- $R^6$ represents hydrogen, halogen, OH, $NH_2$, CN, $(C_1-C_3)$-alkyl, $(C_1-C_3)$-alkoxy, cyclopropyl or vinyl,
- $R^7$ represents hydrogen, halogen, $(C_1-C_3)$-alkyl, $(C_1-C_3)$-alkoxy, $(C_1-C_3)$-alkylthio, cyclopropyl, $(C_1-C_3)$-alkylamino or phenyl, and
- n represents 0, 1 or 2.

20. A compound as claimed in claim 19 having the formula

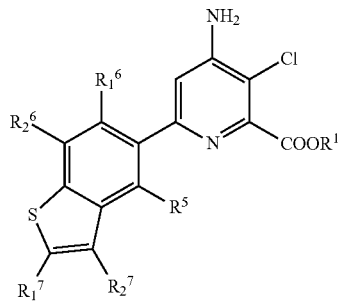

wherein
- $R^1$ represents hydrogen or $(C_1-C_4)$-alkyl,
- $R^5$ represents hydrogen,
- $R_1^6$ represents hydrogen or halogen,
- $R_2^6$ represent hydrogen,
- $R_1^7$ represents hydrogen, and
- $R_2^7$ represent hydrogen.

21. A compound as claimed in claim 19 having the formula

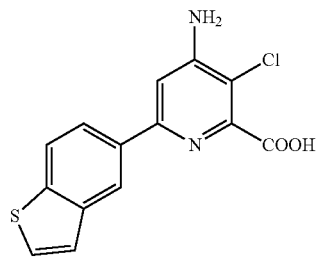

or the methyl ester thereof.

22. A compound as claimed in claim 19 having the formula

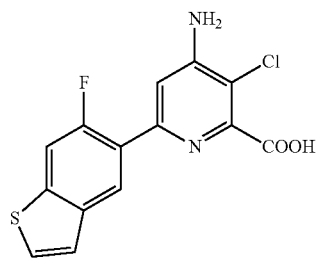

or the methyl ester thereof.

* * * * *